(12) United States Patent
Tycko et al.

(10) Patent No.: US 12,286,727 B2
(45) Date of Patent: Apr. 29, 2025

(54) ASSESSING NUCLEASE CLEAVAGE

(71) Applicant: Editas Medicine, Inc., Cambridge, MA (US)

(72) Inventors: Joshua C. Tycko, Redwood City, CA (US); Barrett Ethan Steinberg, Cambridge, MA (US); Nick Huston, New Haven, CT (US); Hariharan Jayaram, San Mateo, CA (US)

(73) Assignee: Editas Medicine, Inc., Cambridge, MA (US)

( * ) Notice: Subject to any disclaimer, the term of this patent is extended or adjusted under 35 U.S.C. 154(b) by 743 days.

(21) Appl. No.: 16/470,870

(22) PCT Filed: Dec. 19, 2017

(86) PCT No.: PCT/US2017/067444
§ 371 (c)(1),
(2) Date: Jun. 18, 2019

(87) PCT Pub. No.: WO2018/119010
PCT Pub. Date: Jun. 28, 2018

(65) Prior Publication Data
US 2020/0190699 A1 Jun. 18, 2020

Related U.S. Application Data

(60) Provisional application No. 62/436,239, filed on Dec. 19, 2016.

(51) Int. Cl.
*C12Q 1/68* (2018.01)
*C12N 9/22* (2006.01)
*C12N 15/63* (2006.01)
*C12Q 1/44* (2006.01)
*C12Q 1/6869* (2018.01)
*C40B 40/06* (2006.01)

(52) U.S. Cl.
CPC ............. *C40B 40/06* (2013.01); *C12N 9/22* (2013.01); *C12N 15/63* (2013.01); *C12Q 1/44* (2013.01); *C12Q 1/6869* (2013.01)

(58) Field of Classification Search
USPC ......... 435/6.1, 6.11, 91.1, 183; 436/94, 501; 536/23.1, 24.3, 24.33
See application file for complete search history.

(56) References Cited

U.S. PATENT DOCUMENTS 8,546,553 B2   10/2013   Terns et al.
8,697,359 B1    4/2014   Zhang
(Continued)

FOREIGN PATENT DOCUMENTS

WO   WO-2007/025097 A2   3/2007
WO   WO-2010/011961 A2   1/2010
(Continued)

OTHER PUBLICATIONS

US 10,077,445 B2, 09/2018, Dounda et al. (withdrawn)
(Continued)

*Primary Examiner* — Frank W Lu
(74) *Attorney, Agent, or Firm* — Choate, Hall & Stewart LLP; Rolando Medina; Meaghan E. Bychowski

(57) ABSTRACT

The present disclosure relates to systems and methods of analyzing cleavage profiles of nucleases.

18 Claims, 24 Drawing Sheets

Specification includes a Sequence Listing.

(56) References Cited

U.S. PATENT DOCUMENTS

| | | |
|---|---|---|
| 8,771,945 B1 | 7/2014 | Zhang |
| 8,795,965 B2 | 8/2014 | Zhang |
| 8,865,406 B2 | 10/2014 | Zhang et al. |
| 8,871,445 B2 | 10/2014 | Cong et al. |
| 8,889,356 B2 | 11/2014 | Zhang |
| 8,889,418 B2 | 11/2014 | Zhang et al. |
| 8,895,308 B1 | 11/2014 | Zhang et al. |
| 8,906,616 B2 | 12/2014 | Zhang et al. |
| 8,932,814 B2 | 1/2015 | Cong et al. |
| 8,945,839 B2 | 2/2015 | Zhang |
| 8,993,233 B2 | 3/2015 | Zhang et al. |
| 8,999,641 B2 | 4/2015 | Zhang et al. |
| 9,023,649 B2 | 5/2015 | Mali et al. |
| 9,074,199 B1 | 7/2015 | Chavez et al. |
| 9,234,213 B2 | 1/2016 | Wu |
| 9,260,723 B2 | 2/2016 | Mali et al. |
| 9,260,752 B1 | 2/2016 | May et al. |
| 9,267,135 B2 | 2/2016 | Church et al. |
| 9,322,037 B2 | 4/2016 | Liu et al. |
| 9,388,430 B2 | 7/2016 | Liu et al. |
| 9,404,098 B2 | 8/2016 | Terns et al. |
| 9,410,198 B2 | 8/2016 | May et al. |
| 9,422,553 B2 | 8/2016 | Terns et al. |
| 9,512,446 B1 | 12/2016 | Joung et al. |
| 9,567,603 B2 | 2/2017 | Joung et al. |
| 9,567,604 B2 | 2/2017 | Joung et al. |
| 9,587,252 B2 | 3/2017 | Church et al. |
| 9,637,739 B2 | 5/2017 | Siksnys et al. |
| 9,663,782 B2 | 5/2017 | Yu et al. |
| 9,688,971 B2 | 6/2017 | Doudna et al. |
| 9,725,714 B2 | 8/2017 | May et al. |
| 9,738,908 B2 | 8/2017 | Wu |
| 9,752,132 B2 | 9/2017 | Joung et al. |
| 9,790,490 B2 | 10/2017 | Zhang et al. |
| 9,803,194 B2 | 10/2017 | May et al. |
| 9,809,814 B1 | 11/2017 | May et al. |
| 9,822,370 B2 | 11/2017 | Musunuru et al. |
| 9,822,372 B2 | 11/2017 | Zhang et al. |
| 9,840,713 B2 | 12/2017 | Zhang |
| 9,873,894 B2 | 1/2018 | Conway et al. |
| 9,879,269 B2 | 1/2018 | Barrangou et al. |
| 9,885,026 B2 | 2/2018 | Brouns et al. |
| 9,902,974 B2 | 2/2018 | Conway et al. |
| 9,909,122 B2 | 3/2018 | May et al. |
| 9,926,545 B2 | 3/2018 | Joung et al. |
| 9,926,546 B2 | 3/2018 | Joung et al. |
| 9,944,912 B2 | 4/2018 | Joung et al. |
| 9,963,689 B2 | 5/2018 | Doudna et al. |
| 9,970,001 B2 | 5/2018 | Miller |
| 9,970,024 B2 | 5/2018 | Church et al. |
| 10,066,233 B2 | 9/2018 | Barrangou et al. |
| 10,077,453 B2 | 9/2018 | Liu et al. |
| 10,093,910 B2 | 10/2018 | Joung et al. |
| 10,100,291 B2 | 10/2018 | Chavez et al. |
| 10,113,167 B2 | 10/2018 | Doudna et al. |
| 10,113,179 B2 | 10/2018 | Begemann et al. |
| 10,113,207 B2 | 10/2018 | Wang |
| 10,119,133 B2 | 11/2018 | Joung et al. |
| 10,125,361 B2 | 11/2018 | May et al. |
| 10,202,589 B2 | 2/2019 | Joung et al. |
| 10,202,619 B2 | 2/2019 | Wu |
| 10,227,611 B2 | 3/2019 | Doudna et al. |
| 10,266,850 B2 | 4/2019 | Doudna et al. |
| 10,301,651 B2 | 5/2019 | Doudna et al. |
| 10,308,961 B2 | 6/2019 | Doudna et al. |
| 10,329,587 B2 | 6/2019 | Church et al. |
| 10,351,878 B2 | 7/2019 | Doudna et al. |
| 10,358,658 B2 | 7/2019 | Doudna et al. |
| 10,358,659 B2 | 7/2019 | Doudna et al. |
| 10,377,998 B2 | 8/2019 | Zhang et al. |
| 10,378,027 B2 | 8/2019 | Joung et al. |
| 10,385,360 B2 | 8/2019 | Doudna et al. |
| 10,392,607 B2 | 8/2019 | Sternberg et al. |
| 10,400,253 B2 | 9/2019 | Doudna et al. |
| 10,407,697 B2 | 9/2019 | Doudna et al. |
| 10,415,059 B2 | 9/2019 | Joung et al. |
| 10,415,061 B2 | 9/2019 | Doudna et al. |
| 10,421,980 B2 | 9/2019 | Doudna et al. |
| 10,428,319 B2 | 10/2019 | Steinberg et al. |
| 10,428,352 B2 | 10/2019 | Doudna et al. |
| 10,435,679 B2 | 10/2019 | Chavez et al. |
| 10,435,708 B2 | 10/2019 | Mali et al. |
| 10,443,076 B2 | 10/2019 | Doudna et al. |
| 2010/0076057 A1 | 3/2010 | Sontheimer et al. |
| 2010/0093617 A1 | 4/2010 | Barrangou et al. |
| 2013/0011828 A1 | 1/2013 | Barrangou et al. |
| 2014/0068797 A1 | 3/2014 | Doudna et al. |
| 2014/0093941 A1 | 4/2014 | Terns et al. |
| 2014/0179770 A1 | 6/2014 | Zhang et al. |
| 2014/0186843 A1 | 7/2014 | Zhang et al. |
| 2014/0186919 A1 | 7/2014 | Zhang et al. |
| 2014/0186958 A1 | 7/2014 | Zhang et al. |
| 2014/0189896 A1 | 7/2014 | Zhang et al. |
| 2014/0199767 A1 | 7/2014 | Barrangou et al. |
| 2014/0242664 A1 | 8/2014 | Zhang et al. |
| 2014/0242699 A1 | 8/2014 | Zhang |
| 2014/0256046 A1 | 9/2014 | Zhang et al. |
| 2014/0273037 A1 | 9/2014 | Wu |
| 2014/0273226 A1 | 9/2014 | Wu |
| 2014/0273230 A1 | 9/2014 | Chen et al. |
| 2014/0273233 A1 | 9/2014 | Chen et al. |
| 2014/0287938 A1 | 9/2014 | Zhang et al. |
| 2014/0294773 A1 | 10/2014 | Brouns et al. |
| 2014/0302563 A1 | 10/2014 | Doudna et al. |
| 2014/0310830 A1 | 10/2014 | Zhang et al. |
| 2014/0315985 A1 | 10/2014 | May et al. |
| 2014/0342456 A1 | 11/2014 | Mali et al. |
| 2014/0342457 A1 | 11/2014 | Mali et al. |
| 2014/0342458 A1 | 11/2014 | Mali et al. |
| 2014/0356956 A1 | 12/2014 | Church et al. |
| 2014/0357523 A1 | 12/2014 | Zeiner et al. |
| 2014/0357530 A1 | 12/2014 | Zhang et al. |
| 2014/0377868 A1 | 12/2014 | Joung et al. |
| 2015/0020223 A1 | 1/2015 | Zhang et al. |
| 2015/0024499 A1 | 1/2015 | Brouns et al. |
| 2015/0024500 A1 | 1/2015 | Yu et al. |
| 2015/0031132 A1 | 1/2015 | Church et al. |
| 2015/0031133 A1 | 1/2015 | Church et al. |
| 2015/0031134 A1 | 1/2015 | Zhang et al. |
| 2015/0044772 A1 | 2/2015 | Zhao |
| 2015/0045546 A1 | 2/2015 | Siksnys et al. |
| 2015/0050699 A1 | 2/2015 | Siksnys et al. |
| 2015/0056705 A1 | 2/2015 | Conway et al. |
| 2015/0071889 A1 | 3/2015 | Musunuru et al. |
| 2015/0071898 A1 | 3/2015 | Liu et al. |
| 2015/0071899 A1 | 3/2015 | Liu et al. |
| 2015/0079681 A1 | 3/2015 | Zhang |
| 2015/0176013 A1 | 6/2015 | Musunuru et al. |
| 2015/0184139 A1 | 7/2015 | Zhang et al. |
| 2015/0203872 A1 | 7/2015 | Zhang |
| 2015/0232833 A1 | 8/2015 | Mali et al. |
| 2015/0232882 A1 | 8/2015 | Zhang et al. |
| 2015/0240261 A1 | 8/2015 | Siksnys et al. |
| 2015/0247150 A1 | 9/2015 | Zhang et al. |
| 2015/0259684 A1 | 9/2015 | Church et al. |
| 2015/0259704 A1 | 9/2015 | Church et al. |
| 2015/0284727 A1 | 10/2015 | Kim et al. |
| 2015/0291961 A1 | 10/2015 | Siksnys et al. |
| 2015/0291965 A1 | 10/2015 | Zhang et al. |
| 2015/0291966 A1 | 10/2015 | Zhang et al. |
| 2015/0322457 A1 | 11/2015 | Kim et al. |
| 2015/0344912 A1 | 12/2015 | Kim et al. |
| 2015/0353905 A1 | 12/2015 | Weiss et al. |
| 2015/0353917 A1 | 12/2015 | Miller |
| 2015/0356239 A1 | 12/2015 | Zhang et al. |
| 2016/0002670 A1 | 1/2016 | Church et al. |
| 2016/0010076 A1 | 1/2016 | Joung et al. |
| 2016/0010154 A1 | 1/2016 | Laganiere et al. |
| 2016/0017366 A1 | 1/2016 | Chen et al. |
| 2016/0024523 A1 | 1/2016 | Joung et al. |
| 2016/0024524 A1 | 1/2016 | Joung et al. |
| 2016/0032274 A1 | 2/2016 | Church et al. |
| 2016/0046949 A1 | 2/2016 | May et al. |
| 2016/0046961 A1 | 2/2016 | Jinek et al. |

(56) References Cited

U.S. PATENT DOCUMENTS

| | | |
|---|---|---|
| 2016/0046962 A1 | 2/2016 | May et al. |
| 2016/0046963 A1 | 2/2016 | May et al. |
| 2016/0046978 A1 | 2/2016 | May et al. |
| 2016/0060653 A1 | 3/2016 | Doudna et al. |
| 2016/0060654 A1 | 3/2016 | Doudna et al. |
| 2016/0068864 A1 | 3/2016 | Doudna et al. |
| 2016/0068887 A1 | 3/2016 | May et al. |
| 2016/0076020 A1 | 3/2016 | May et al. |
| 2016/0090607 A1 | 3/2016 | Conway et al. |
| 2016/0102324 A1 | 4/2016 | Duchateau et al. |
| 2016/0108470 A1 | 4/2016 | May et al. |
| 2016/0115488 A1 | 4/2016 | Zhang et al. |
| 2016/0115489 A1 | 4/2016 | Zhang et al. |
| 2016/0122774 A1 | 5/2016 | Duchateau et al. |
| 2016/0130608 A1 | 5/2016 | Doudna et al. |
| 2016/0130609 A1 | 5/2016 | Doudna et al. |
| 2016/0138008 A1 | 5/2016 | Doudna et al. |
| 2016/0138046 A1 | 5/2016 | Wu |
| 2016/0145646 A1 | 5/2016 | Frendewey et al. |
| 2016/0153003 A1 | 6/2016 | Joung et al. |
| 2016/0153004 A1 | 6/2016 | Zhang et al. |
| 2016/0153006 A1 | 6/2016 | Zhang et al. |
| 2016/0160210 A1 | 6/2016 | Mali et al. |
| 2016/0168592 A1 | 6/2016 | Church et al. |
| 2016/0175462 A1 | 6/2016 | Zhang et al. |
| 2016/0184362 A1 | 6/2016 | Duchateau et al. |
| 2016/0186152 A1 | 6/2016 | Brouns et al. |
| 2016/0186213 A1 | 6/2016 | Zhang et al. |
| 2016/0186214 A1 | 6/2016 | Brouns et al. |
| 2016/0201089 A1 | 7/2016 | Gersbach et al. |
| 2016/0208243 A1 | 7/2016 | Zhang et al. |
| 2016/0215276 A1 | 7/2016 | Liu et al. |
| 2016/0222416 A1 | 8/2016 | Church et al. |
| 2016/0237455 A1 | 8/2016 | Glucksmann et al. |
| 2016/0237456 A1 | 8/2016 | Church et al. |
| 2016/0251640 A1 | 9/2016 | May et al. |
| 2016/0272965 A1 | 9/2016 | Zhang et al. |
| 2016/0281072 A1 | 9/2016 | Zhang |
| 2016/0298097 A1 | 10/2016 | Chavez et al. |
| 2016/0298125 A1 | 10/2016 | Chen et al. |
| 2016/0298132 A1 | 10/2016 | Chen et al. |
| 2016/0298133 A1 | 10/2016 | Chen et al. |
| 2016/0298134 A1 | 10/2016 | Chen et al. |
| 2016/0298135 A1 | 10/2016 | Chen et al. |
| 2016/0298136 A1 | 10/2016 | Chen et al. |
| 2016/0298137 A1 | 10/2016 | Chen et al. |
| 2016/0298138 A1 | 10/2016 | Chen et al. |
| 2016/0304907 A1 | 10/2016 | Mali et al. |
| 2016/0312198 A1 | 10/2016 | Joung et al. |
| 2016/0312199 A1 | 10/2016 | Joung et al. |
| 2016/0312280 A1 | 10/2016 | May et al. |
| 2016/0319260 A1 | 11/2016 | Joung et al. |
| 2016/0319261 A1 | 11/2016 | Joung et al. |
| 2016/0319281 A1 | 11/2016 | Tsai et al. |
| 2016/0319349 A1 | 11/2016 | May et al. |
| 2016/0340662 A1 | 11/2016 | Zhang et al. |
| 2016/0355796 A1 | 12/2016 | Davidson et al. |
| 2016/0355797 A1 | 12/2016 | Konermann et al. |
| 2016/0355816 A1 | 12/2016 | Terns et al. |
| 2017/0037416 A1 | 2/2017 | Barrangou et al. |
| 2017/0044569 A9 | 2/2017 | Church et al. |
| 2017/0051276 A1 | 2/2017 | May et al. |
| 2017/0051310 A1 | 2/2017 | Doudna et al. |
| 2017/0051312 A1 | 2/2017 | Jinek et al. |
| 2017/0058271 A1 | 3/2017 | Joung et al. |
| 2017/0073705 A1 | 3/2017 | Chen et al. |
| 2017/0081650 A1 | 3/2017 | Joung et al. |
| 2017/0107536 A1 | 4/2017 | Zhang et al. |
| 2017/0114369 A1 | 4/2017 | Donohoue et al. |
| 2017/0152508 A1 | 6/2017 | Joung et al. |
| 2017/0152528 A1 | 6/2017 | Zhang |
| 2017/0166893 A1 | 6/2017 | Doudna et al. |
| 2017/0166903 A1 | 6/2017 | Zhang et al. |
| 2017/0175142 A1 | 6/2017 | Zhang et al. |
| 2017/0175144 A1 | 6/2017 | Zhang et al. |
| 2017/0191078 A1 | 7/2017 | Zhang et al. |
| 2017/0191082 A1 | 7/2017 | Chen et al. |
| 2017/0198269 A1 | 7/2017 | Zhang et al. |
| 2017/0211142 A1 | 7/2017 | Smargon et al. |
| 2017/0233703 A1 | 8/2017 | Xie et al. |
| 2017/0268022 A1 | 9/2017 | Liu et al. |
| 2017/0298330 A1 | 10/2017 | Sato et al. |
| 2017/0306307 A1 | 10/2017 | Zhang et al. |
| 2017/0306335 A1 | 10/2017 | Zhang et al. |
| 2017/0327805 A1 | 11/2017 | Joung et al. |
| 2017/0327806 A1 | 11/2017 | Joung et al. |
| 2017/0327820 A1 | 11/2017 | May et al. |
| 2017/0349915 A1 | 12/2017 | May et al. |
| 2018/0002682 A1 | 1/2018 | Sternberg et al. |
| 2018/0030425 A1 | 2/2018 | Joung et al. |
| 2018/0066242 A1 | 3/2018 | Zhang et al. |
| 2018/0073002 A1 | 3/2018 | Deiters et al. |
| 2018/0080051 A1 | 3/2018 | Sheikh et al. |
| 2018/0100147 A1 | 4/2018 | Yates et al. |
| 2018/0100148 A1 | 4/2018 | Vakulskas et al. |
| 2018/0119121 A1 | 5/2018 | Brouns et al. |
| 2018/0119175 A1 | 5/2018 | Conway et al. |
| 2018/0127780 A1 | 5/2018 | Liu et al. |
| 2018/0135073 A1 | 5/2018 | Chen et al. |
| 2018/0148735 A1 | 5/2018 | Begemann et al. |
| 2018/0155708 A1 | 6/2018 | Church et al. |
| 2018/0155716 A1 | 6/2018 | Zhang et al. |
| 2018/0163188 A1 | 6/2018 | Xie et al. |
| 2018/0163213 A1 | 6/2018 | Aneja et al. |
| 2018/0187176 A1 | 7/2018 | Behlke et al. |
| 2018/0187195 A1 | 7/2018 | Siksnys et al. |
| 2018/0208931 A1 | 7/2018 | Doudna et al. |
| 2018/0216088 A1 | 8/2018 | Joung et al. |
| 2018/0230495 A1 | 8/2018 | Doudna et al. |
| 2018/0230496 A1 | 8/2018 | Doudna et al. |
| 2018/0230497 A1 | 8/2018 | Doudna et al. |
| 2018/0237801 A1 | 8/2018 | Doudna et al. |
| 2018/0245071 A1* | 8/2018 | Joung ............... C12N 15/1093 |
| 2018/0245100 A1 | 8/2018 | Doudna et al. |
| 2018/0245101 A1 | 8/2018 | Doudna et al. |
| 2018/0251788 A1 | 9/2018 | Donohoue et al. |
| 2018/0251791 A1 | 9/2018 | Doudna et al. |
| 2018/0251793 A1 | 9/2018 | Doudna et al. |
| 2018/0251794 A1 | 9/2018 | Doudna et al. |
| 2018/0251795 A1 | 9/2018 | Charpentier et al. |
| 2018/0265864 A1 | 9/2018 | Li et al. |
| 2018/0273981 A1 | 9/2018 | Doudna et al. |
| 2018/0282713 A1 | 10/2018 | Van Der Oost |
| 2018/0282714 A1 | 10/2018 | Joung et al. |
| 2018/0282764 A1 | 10/2018 | Jinek et al. |
| 2018/0291383 A1 | 10/2018 | Musunuru et al. |
| 2018/0298360 A1 | 10/2018 | Sternberg et al. |
| 2018/0298406 A1 | 10/2018 | Doudna et al. |
| 2018/0298407 A1 | 10/2018 | Doudna et al. |
| 2018/0312824 A1 | 11/2018 | Zhang et al. |
| 2018/0312874 A1 | 11/2018 | Doudna et al. |
| 2018/0312875 A1 | 11/2018 | Doudna et al. |
| 2018/0312876 A1 | 11/2018 | Doudna et al. |
| 2018/0319850 A1 | 11/2018 | Payne et al. |
| 2018/0320163 A1 | 11/2018 | Koonin et al. |
| 2018/0320197 A1 | 11/2018 | Gersbach et al. |
| 2018/0320201 A1 | 11/2018 | Vakulskas et al. |
| 2018/0327761 A1 | 11/2018 | Duchateau et al. |
| 2018/0346927 A1 | 12/2018 | Doudna et al. |
| 2018/0355332 A1 | 12/2018 | Steinberg et al. |
| 2019/0002889 A1 | 1/2019 | Cheng et al. |
| 2019/0002921 A1 | 1/2019 | Doudna et al. |
| 2019/0002922 A1 | 1/2019 | Doudna et al. |
| 2019/0002923 A1 | 1/2019 | Doudna et al. |
| 2019/0010471 A1 | 1/2019 | Zhang et al. |
| 2019/0010481 A1 | 1/2019 | Joung et al. |
| 2019/0010520 A1 | 1/2019 | Doudna et al. |
| 2019/0048340 A1 | 2/2019 | Charpentier et al. |
| 2019/0062790 A1 | 2/2019 | Doudna et al. |
| 2019/0071688 A1 | 3/2019 | Begemann et al. |
| 2019/0083656 A1 | 3/2019 | Khalili et al. |
| 2019/0085329 A1 | 3/2019 | Siksnys et al. |
| 2019/0093129 A1 | 3/2019 | Doudna et al. |
| 2019/0106687 A1 | 4/2019 | Joung et al. |

(56) References Cited

U.S. PATENT DOCUMENTS

| | | |
|---|---|---|
| 2019/0106711 A1 | 4/2019 | Doudna et al. |
| 2019/0106712 A1 | 4/2019 | Doudna et al. |
| 2019/0106713 A1 | 4/2019 | Doudna et al. |
| 2019/0106714 A1 | 4/2019 | Doudna et al. |
| 2019/0106715 A1 | 4/2019 | Doudna et al. |
| 2019/0161743 A1 | 5/2019 | Church et al. |
| 2019/0218602 A1 | 7/2019 | Zhang et al. |
| 2019/0264186 A1 | 8/2019 | Yamano et al. |
| 2019/0284583 A1 | 9/2019 | Doudna et al. |

FOREIGN PATENT DOCUMENTS

| | | |
|---|---|---|
| WO | WO-2013/098244 A1 | 7/2013 |
| WO | WO-2013/141680 A1 | 9/2013 |
| WO | WO-2013/142578 A1 | 9/2013 |
| WO | WO-2013/169398 A2 | 11/2013 |
| WO | WO-2013/176772 A1 | 11/2013 |
| WO | WO-2014/018423 A2 | 1/2014 |
| WO | WO-2014/065596 A1 | 5/2014 |
| WO | WO-2014/089290 A1 | 6/2014 |
| WO | WO-2014/093479 A1 | 6/2014 |
| WO | WO-2014/093595 A1 | 6/2014 |
| WO | WO-2014/093622 A2 | 6/2014 |
| WO | WO-2014/093635 A1 | 6/2014 |
| WO | WO-2014/093655 A2 | 6/2014 |
| WO | WO-2014/093661 A2 | 6/2014 |
| WO | WO-2014/093694 A1 | 6/2014 |
| WO | WO-2014/093701 A1 | 6/2014 |
| WO | WO-2014/093709 A1 | 6/2014 |
| WO | WO-2014/093712 A1 | 6/2014 |
| WO | WO-2014/093718 A1 | 6/2014 |
| WO | WO-2014/099744 A1 | 6/2014 |
| WO | WO-2014/099750 A2 | 6/2014 |
| WO | WO-2014/113493 A1 | 7/2014 |
| WO | WO-2014/144288 A1 | 9/2014 |
| WO | WO-2014/144592 A2 | 9/2014 |
| WO | WO-2014/144761 A2 | 9/2014 |
| WO | WO-2014/145599 A2 | 9/2014 |
| WO | WO-2014/150624 A1 | 9/2014 |
| WO | WO-2014/152432 A2 | 9/2014 |
| WO | WO-2014/165825 A2 | 10/2014 |
| WO | WO-2014/186585 A2 | 11/2014 |
| WO | WO-2014/191518 A1 | 12/2014 |
| WO | WO-2014/191521 A2 | 12/2014 |
| WO | WO-2014/197568 A2 | 12/2014 |
| WO | WO-2014/197748 A2 | 12/2014 |
| WO | WO-2014/204578 A1 | 12/2014 |
| WO | WO-2014/204724 A1 | 12/2014 |
| WO | WO-2014/204725 A1 | 12/2014 |
| WO | WO-2014/204727 A1 | 12/2014 |
| WO | WO-2014/204728 A1 | 12/2014 |
| WO | WO-2014/204729 A1 | 12/2014 |
| WO | WO-2015/006290 A1 | 1/2015 |
| WO | WO-2015/006294 A2 | 1/2015 |
| WO | WO-2015/010114 A1 | 1/2015 |
| WO | WO-2015/013583 A2 | 1/2015 |
| WO | WO-2015/021353 A1 | 2/2015 |
| WO | WO-2015/021426 A1 | 2/2015 |
| WO | WO-2015/035162 A2 | 3/2015 |
| WO | WO-2015/048577 A2 | 4/2015 |
| WO | WO-2015/077318 A1 | 5/2015 |
| WO | WO-2015/089351 A1 | 6/2015 |
| WO | WO-2015/089354 A1 | 6/2015 |
| WO | WO-2015/089427 A1 | 6/2015 |
| WO | WO-2015/089486 A2 | 6/2015 |
| WO | WO-2015/188056 A1 | 12/2015 |
| WO | WO-2015/188065 A1 | 12/2015 |
| WO | WO-2016/022363 A2 | 2/2016 |
| WO | WO-2016/028682 A1 | 2/2016 |
| WO | WO-2016/057821 A2 | 4/2016 |
| WO | WO-2016/073990 A2 | 5/2016 |
| WO | WO-2016/081923 A2 | 5/2016 |
| WO | WO-2016/106236 A1 | 6/2016 |
| WO | WO-2016/106244 A1 | 6/2016 |
| WO | WO-2016/112242 A1 | 7/2016 |
| WO | WO-2016/114972 A1 | 7/2016 |
| WO | WO-2016/141224 A1 | 9/2016 |
| WO | WO-2016/161207 A1 | 10/2016 |
| WO | WO-2016/164797 A1 | 10/2016 |
| WO | WO-2016/166340 A1 | 10/2016 |
| WO | WO-2016/167300 A1 | 10/2016 |
| WO | WO-2016/196655 A1 | 12/2016 |
| WO | WO-2016/205613 A1 | 12/2016 |
| WO | WO-2016/205711 A1 | 12/2016 |
| WO | WO-2016/205749 A1 | 12/2016 |
| WO | WO-2016/205759 A1 | 12/2016 |
| WO | WO-2017/015015 A1 | 1/2017 |
| WO | WO-2017/040348 A1 | 3/2017 |
| WO | WO-2017/048969 A1 | 3/2017 |
| WO | WO-2017/064546 A1 | 4/2017 |
| WO | WO-2017/066588 A2 | 4/2017 |
| WO | WO-2017/070633 A2 | 4/2017 |
| WO | WO-2017/081288 A1 | 5/2017 |
| WO | WO-2017/099494 A1 | 6/2017 |
| WO | WO-2017/127807 A1 | 7/2017 |
| WO | WO-2017/136335 A1 | 8/2017 |
| WO | WO-2017/161068 A1 | 9/2017 |
| WO | WO-2017/181107 A2 | 10/2017 |
| WO | WO-2017/184768 A1 | 10/2017 |
| WO | WO-2017/189308 A1 | 11/2017 |
| WO | WO-2017/197238 A1 | 11/2017 |
| WO | WO-2017/219027 A1 | 12/2017 |
| WO | WO-2017/219033 A1 | 12/2017 |
| WO | WO-2017/222773 A1 | 12/2017 |
| WO | WO-2018/022634 A1 | 2/2018 |
| WO | WO-2018/035250 A1 | 2/2018 |
| WO | WO-2018/035387 A1 | 2/2018 |
| WO | WO-2018/035388 A1 | 2/2018 |
| WO | WO-2018/038772 A1 | 3/2018 |
| WO | WO-2018/049073 A1 | 3/2018 |
| WO | WO-2018/049077 A1 | 3/2018 |
| WO | WO-2018/049079 A1 | 3/2018 |
| WO | WO-2018/051347 A1 | 3/2018 |
| WO | WO-2018/052247 A1 | 3/2018 |
| WO | WO-2018/053053 A1 | 3/2018 |
| WO | WO-2018/064352 A1 | 4/2018 |
| WO | WO-2018/064371 A1 | 4/2018 |
| WO | WO-2018/068053 A2 | 4/2018 |
| WO | WO-2018/069474 A1 | 4/2018 |
| WO | WO-2018/071868 A1 | 4/2018 |
| WO | WO-2018/071892 A1 | 4/2018 |
| WO | WO-2018/074979 A1 | 4/2018 |
| WO | WO-2018/089664 A1 | 5/2018 |
| WO | WO-2018/098383 A1 | 5/2018 |
| WO | WO-2018/108272 A1 | 6/2018 |
| WO | WO-2018/108338 A1 | 6/2018 |
| WO | WO-2018/108339 A1 | 6/2018 |
| WO | WO-2018/109101 A1 | 6/2018 |
| WO | WO-2018/112451 A1 | 6/2018 |
| WO | WO-2018/118968 A1 | 6/2018 |
| WO | WO-2018/119010 A1 | 6/2018 |
| WO | WO-2018/129368 A2 | 7/2018 |
| WO | WO-2018/149888 A1 | 8/2018 |
| WO | WO-2018/170015 A1 | 9/2018 |
| WO | WO-2018/172556 A1 | 9/2018 |
| WO | WO-2018/183766 A1 | 10/2018 |
| WO | WO-2018/188571 A1 | 10/2018 |
| WO | WO-2018/191715 A2 | 10/2018 |
| WO | WO-2018/195540 A1 | 10/2018 |
| WO | WO-2018/195545 A2 | 10/2018 |
| WO | WO-2018/197495 A1 | 11/2018 |
| WO | WO-2018/201086 A1 | 11/2018 |
| WO | WO-2018/209712 A1 | 11/2018 |
| WO | WO-2018/213351 A1 | 11/2018 |
| WO | WO-2018/221685 A1 | 12/2018 |
| WO | WO-2018/226855 A1 | 12/2018 |
| WO | WO-2018/227114 A1 | 12/2018 |
| WO | WO-2019/006471 A2 | 1/2019 |
| WO | WO-2019/009682 A2 | 1/2019 |
| WO | WO-2019/018041 A1 | 1/2019 |
| WO | WO-2019/036513 A1 | 2/2019 |
| WO | WO-2019/040650 A1 | 2/2019 |
| WO | WO-2019/046540 A1 | 3/2019 |
| WO | WO-2019/049913 A1 | 3/2019 |

(56) References Cited

FOREIGN PATENT DOCUMENTS

| | | |
|---|---|---|
| WO | WO-2019/051419 A1 | 3/2019 |
| WO | WO-2019/060469 A2 | 3/2019 |
| WO | WO-2019/067322 A1 | 4/2019 |
| WO | WO-2019/072596 A1 | 4/2019 |
| WO | WO-2019/074542 A1 | 4/2019 |
| WO | WO-2019/083532 A1 | 5/2019 |
| WO | WO-2019/089796 A1 | 5/2019 |
| WO | WO-2019/089804 A1 | 5/2019 |
| WO | WO-2019/089808 A1 | 5/2019 |
| WO | WO-2019/089820 A1 | 5/2019 |
| WO | WO-2019/090173 A1 | 5/2019 |
| WO | WO-2019/090174 A1 | 5/2019 |
| WO | WO-2019/090175 A1 | 5/2019 |
| WO | WO-2019/092042 A1 | 5/2019 |
| WO | WO-2019/092505 A1 | 5/2019 |
| WO | WO-2019/099943 A1 | 5/2019 |
| WO | WO-2019/126709 A1 | 6/2019 |
| WO | WO-2019/126716 A1 | 6/2019 |
| WO | WO-2019/126762 A2 | 6/2019 |
| WO | WO-2019/126774 A1 | 6/2019 |
| WO | WO-2019/168953 A1 | 9/2019 |
| WO | WO-2019/178427 A1 | 9/2019 |
| WO | WO-2019/178428 A1 | 9/2019 |
| WO | WO-2019/183150 A1 | 9/2019 |

OTHER PUBLICATIONS

"Cas 9" from Wikipedia. Printed on Jun. 10, 2022.*

What is the PAM sequence for CRISPR and where is it?. Printed on Jun. 10, 2022.*

"Restriction enzyme", "CRISPR", and "Guide RNA" from Wikipedia. Printed on Nov. 9, 2022.*

Anders, C. et al., Structural basis of PAM-dependent target DNA recognition by the Cas9 endonuclease, Nature, 513(7519):569-73 (2014).

Bolivar, F. et al, Construction and Characterization of New Cloning Vehicles I. Ampicillin-Resistant Derivatives of the Plasmid pMB9, Gene, 2: 75-93 (1977).

Briner, A. E. et al. Guide RNA functional modules direct Cas9 activity and orthogonality Molecular Cell, 56(2), 333-339 (2014).

Cong, L. et al., Multiplex genome engineering using CRISPR/Cas systems, Science, 339(6121):819-23 (2013).

Esvelt, K. M. and Wang, H.H., Genome-scale engineering for systems and synthetic biology, Molecular Systems Biology, 9:641 (2013).

Guilinger, J. P. et al, Broad specificity profiling of TALENs results in engineered nucleases with improved DNA-cleavage specificity, Nature Methods, 11(4): 429-435 (2014).

Hsu, P. et al, DNA targeting specificity of RNA-guided Cas9 nuclease, Nature Biotechnology, 31(9): 827-832 (2013).

International Search Report for PCT/US2017/067444 (Assessing Nuclease Cleavage, filed Dec. 19, 2017), issued by ISA/EPO, 7 pages (Apr. 10, 2018).

Jacobs, T. B. et al, Targeted genome modifications in soybean with CRISPR/Cas9, BMC Biotechnology, 15(16): 1-10 (2015).

Jiang, W. et al., RNA-guided editing of bacterial genomes using CRISPR-Cas systems [Manuscript title: CRISPR-assisted editing of bacterial genomes], Nat Biotechnology., 31(3): 233-9 (2013).

Jinek, M. et al., A programmable dual-RNA-guided DNA endonuclease in adaptive, bacterial immunity, Science, 337(6096): 816-821 (2012).

Jinek, M. et al., Structures of Cas9 endonucleases reveal RNA-mediated conformational activation, Science, 343(6176), 1247997 (2014).

Mali, P. et al., RNA-guided human genome engineering via Cas9, Science, 339(6121): 823-826 (2013).

Nishimasu, H. et al., Crystal structure of Cas9 in complex with guide RNA and target DNA. Cell, 156: 935-949 (2014).

Nishimasu, H. et al., Crystal Structure of *Staphylococcus aureus* Cas9, Cell, 162:1113-1126 (2015).

Pattanayak, V. et al, High-throughput profiling of off-target DNA cleavage reveals RNA-programmed Cas9 nuclease specificity, Nature Biotechnology, 31(9): 839-843 (2013).

Ran, F.A. et al., Double nicking by RNA-guided CRISPR Cas9 for enhanced genome editing specificity, Cell, 154(6), 1380-1389 (2013).

Shmakov et al., Discovery and Functional Characterization of Diverse Class 2 CRISPR-Cas Systems, Molecular Cell, 60(3):385-397 (2015).

Sternberg, S.H. et al., DNA interrogation by the CRISPR RNA-guided endonuclease Cas9, Nature, 507:62-67 (2014).

Wang, J.-W. et al, CRISPR/Cas9 nuclease cleavage combined with Gibson assembly for seamless cloning, BioTechniques, 58(4): 161-170 (2015).

Wang, L. et al., A Novel Genetic System Based on Zinc Finger Nucleases for the Identification of Interactions between Proteins In Vivo, PLoS One, 8(12):e85650 (2013).

Written Opinion for PCT/US2017/067444 (Assessing Nuclease Cleavage, filed Dec. 19, 2017), issued by ISA/EPO, 8 pages (Apr. 10, 2018).

Yamano, T. et al. Crystal Structure of Cpf1 in Complex with Guide RNA and Target DNA, Cell, 165(4): 949-962 (2016).

Zetsche, B. et al., Cpf1 is a single RNA-guided endonuclease of a class 2 CRISPR-Cas system, Cell, 163:759-771 (2015).

* cited by examiner

All targets with up to six mismatches

Top 5% predicted off-targets

ASSESSING NUCLEASE CLEAVAGE

CROSS REFERENCE TO RELATED APPLICATIONS

This application is the National Stage of International Application No. PCT/US17/67444, filed Dec. 19, 2017, which claims the benefit of U.S. Provisional Application No. 62/436,239, filed Dec. 19, 2016, the contents of both of which are hereby incorporated herein in their entirety.

SEQUENCE LISTING

The instant application contains a Sequence Listing which has been submitted electronically in ASCII format and is hereby incorporated by reference in its entirety. Said ASCII copy, created on Mar. 14, 2018, is named 2011271-0064_SL.txt and is 12,006 bytes in size.

BACKGROUND

Nucleases such as zinc finger nucleases (ZFNs), transcription activator-like effector nucleases (TALENs), and clustered regularly-interspersed short palindromic repeat (CRISPR)-associated nucleases have become increasingly used because of their ability to be targeted to particular DNA sequences. The value of nucleases such as these as a tool for the treatment of inherited diseases is widely recognized. For example, the U.S. Food and Drug Administration (FDA) held a Science Board Meeting on Nov. 15, 2016 addressing the use of such systems and potential regulatory considerations raised by them. In that meeting, the FDA noted that while Cas9/guide RNA (gRNA) ribonucleoprotein (RNP) complexes may be customized to generate precise edits at a locus of interest, the complexes may also interact with, and cut at, other "off-target" loci. The potential for off-target cuts ("off-targets"), in turn, raises at least a potential regulatory consideration with respect to the approval of therapeutics utilizing these nucleases.

SUMMARY

The present disclosure addresses these potential regulatory considerations by providing new systems and methods for quantitative and/or qualitative characterization of the cleavage profiles of nucleases and/or guide RNAs. Also provided are compositions, nucleic acids and libraries of variant nucleic acid templates that can be used with some of the presently disclosed systems and methods.

In one aspect, the present disclosure provides methods comprising the steps of: (a) incubating a plurality of nucleic acid templates with a first nuclease to obtain a first cleavage composition, (i) wherein the plurality of nucleic acid templates comprises a candidate target site for the first nuclease and a control target site for a control nuclease; (ii) wherein the plurality of nucleic acid templates are incubated with the first nuclease under conditions favorable for cleavage by the first nuclease, and (iii) wherein the first cleavage composition comprises one or both of: a first plurality of cleaved nucleic acid templates comprising a cleaved end and lacking the control target site and lacking at least a portion of the candidate target site, and a first plurality of uncleaved nucleic acid templates. In some embodiments, the method further comprises (b) incubating the first cleavage composition with the control nuclease under conditions to allow cleavage of the first plurality of uncleaved nucleic acid templates by the control nuclease, thereby obtaining a second cleavage composition comprising one or both of: (i) the first plurality of cleaved nucleic acid templates, and (ii) a second plurality of cleaved nucleic acid templates comprising a cleaved end and comprising the candidate target site but lacking the control target site. In some embodiments, the method further comprises (c) ligating the cleaved ends of the second cleavage composition with an oligonucleotide capture probe to obtain a first plurality of ligation products comprising the capture probe and lacking at least a portion of the candidate target site, and a second plurality of ligation products comprising the capture probe and the candidate target site. In some embodiments, the method further comprises a step of (d) determining the levels of the first and second pluralities of ligation products.

In some embodiments, the capture probe comprises a first detection sequence. In some embodiments, the nucleic acid templates further comprise a second detection sequence. In some embodiments, the candidate target site is situated between the control target site and the second detection sequence, the first plurality of ligation products further comprise the second detection sequence, and the second plurality of ligation products further comprise the second detection sequence. In some embodiments, the first detection sequence and/or the second detection sequence mediates capture by an oligonucleotide array and/or facilitates sequencing of the plurality of ligation products. In some embodiments, the method further comprises a step of determining a relative abundance of the first and/or second pluralities of ligation products.

In some embodiments, the first nuclease is an RNA-guided nuclease. In some embodiments, step (b) further comprises incubating the nucleic acid templates with a guide RNA. In some embodiments, the nucleic acid templates further comprise a protospacer adjacent motif (PAM) situated adjacent to the candidate target site. In some embodiments, the RNA-guided nuclease is Cas9.

In some embodiments, step (a) comprises contacting and/or incubating a library of variant nucleic acid templates with the first nuclease. In some embodiments, each variant nucleic acid template comprises a variant of the candidate target site and a unique molecular identifier associated with the variant. In some embodiments, each nucleic acid template further comprises a second detection sequence. In some embodiments, the unique molecular identifier is situated between the variant of the candidate target site and the second detection sequence. In some embodiments, the first plurality of ligation products further comprise the second detection sequence and a unique molecular identifier. In some embodiments, the second plurality of ligation products further comprise the second detection sequence and a unique molecular identifier.

In some embodiments, the library comprises nucleic acid templates comprising fully degenerate sequence variants of the candidate target site. In some embodiments, the library comprises nucleic acid templates comprising less than fully degenerate sequence variants of the candidate target site.

In some embodiments, the library comprises at least about $10^3$, $10^4$, $10^5$, $10^6$, or $10^7$ variant nucleic acid templates. In some embodiments, the library comprises about $10^3$, $10^4$, $10^5$, $10^6$, or $10^7$ variant nucleic acid templates. In some embodiments, the library comprises about $10^3$ to about $10^7$, or about $10^4$ to about $10^6$ variant nucleic acid templates.

In some embodiments, the method further comprising a step of detecting at least one unique molecular identifier associated with a first ligation product. In some embodiments, the method further comprises determining relative abundance of the first ligation product.

In some embodiments, the method further comprises a step of detecting at least one unique molecular identifier associated with a second ligation product. In some embodiments, the method further comprises a step of identifying at least one variant associated with at least one unique molecular identifier present in either or both of the first and second plurality of ligation products.

In some embodiments, step (a) comprises incubating a library of variant nucleic acid templates, each variant nucleic acid template comprising a fixed target site for the first nuclease and variant of the PAM adjacent to and 3' or 5' to the fixed target site. In some embodiments, each variant nucleic acid template further comprises a second detection sequence. In some embodiments, the first plurality of ligation products further comprise the second detection sequence. In some embodiments, the second plurality of ligation products further comprise the second detection sequence.

In some embodiments, the method further comprises a step of amplifying the first and/or second plurality of ligation products. In some embodiments, the nucleic acid templates further comprise a second detection sequence. In some embodiments, the step of amplifying comprises performing an amplification reaction using amplification primers that recognize the first and second detection sequences.

In some embodiments, the method further comprises a step of sequencing the first and/or second plurality of ligation products.

In some embodiments, the control nuclease is a restriction enzyme. In some embodiments, the control target site is a restriction site corresponding to the restriction enzyme.

In some embodiments, the first plurality of cleaved nucleic acid templates comprises a blunt cleaved end. In some embodiments, the blunt end comprises a 5' phosphate group.

In some embodiments, the second plurality of cleaved nucleic acid templates comprises a blunt cleaved end. In some embodiments, the blunt end comprises a 5' phosphate group.

In some embodiments, the control nuclease is a nuclease that produces a blunt end. In some embodiments, the first plurality of cleaved nucleic acid templates comprises a cohesive or sticky end. In some embodiments, the method further comprises a step of generating blunt ends from cohesive or sticky ends after step (a) and/or step (b). In some embodiments, the step of generating a blunt end comprises incubating the first cleavage composition from step (a) and/or the second cleavage composition from step (b) with a DNA polymerase. In some embodiments, the step of generating a blunt end comprises incubating the first cleavage composition from step (a) and/or the second cleavage composition from step (b) with an exonuclease.

In some embodiments, step (c) comprises ligating with a plurality of capture probes. In some embodiments, each capture probe comprises the same first detection sequence. In some embodiments, each capture probe further comprises a randomized barcode sequence.

In some embodiments, the method further comprises a step of analyzing, for the candidate target sequence, or for each variant of the candidate target sequence, the distribution of randomized barcode sequences present in the first and/or second plurality of ligation products. In some embodiments, the capture probe further comprises a Hamming code sequence.

In another aspect, the disclosure features methods comprising the steps of: (a) incubating a library of variant nucleic acid templates with a first nuclease to obtain a first cleavage composition, (i) wherein each nucleic acid template comprises, in order from 5' to 3' or 3' to 5': a control target site for a control nuclease; a variant target site for the first nuclease, a unique molecular identifier associated with the variant target site, and a first detection sequence, (ii) wherein the library is incubated with the first nuclease under conditions favorable for cleavage by the first nuclease, and (iii) wherein the first cleavage composition comprises one or both of: a first plurality of cleaved nucleic acid templates comprising a cleaved end, lacking the control target site, and lacking at least a portion of the candidate target site, and a first plurality of uncleaved nucleic acid templates. In some embodiments, the method further comprises (b) incubating the first cleavage composition with the control nuclease under conditions to allow cleavage of the first plurality of uncleaved nucleic acid templates by the control nuclease, thereby obtaining a second cleavage composition comprising one or both of: (i) the first plurality of cleaved nucleic acid templates, and (ii) a second plurality of cleaved nucleic acid templates comprising a cleaved end and comprising the candidate target site but lacking the control target site. In some embodiments, the method further comprises (c) ligating the cleaved ends of the second cleavage composition with an oligonucleotide capture probe comprising a second detection sequence to obtain: (i) a first plurality of ligation products comprising the capture probe and lacking at least a portion of the candidate target site, and (ii) a second plurality of ligation products comprising the capture probe and the candidate target site. In some embodiments, the method further comprises (d) determining relative abundance of at least one unique molecular identifier associated with a first ligation product and/or a second ligation product. In some embodiments, the method further comprises a step of identifying at least one variant associated with at least one unique molecular identifier present in either or both of the first and second plurality of ligation products.

In some embodiments, the first detection sequence and/or the second detection sequence mediates capture by an oligonucleotide array and/or facilitates sequencing of the plurality of ligation products.

In another aspect, the disclosure provides methods comprising the steps of: (a) incubating a library of variant nucleic acid templates with an RNA-guided endonuclease to obtain a first cleavage composition, (i) wherein each nucleic acid template comprises: a first target site for the RNA-guided endonuclease, a variant of a protospacer-adjacent motif (PAM) adjacent to and 3' to the first target site, and a first detection sequence (ii) wherein the library is incubated with the RNA-guided endonuclease under conditions favorable for cleavage by the RNA-guided endonuclease, (iii) wherein the first cleavage composition comprises a first plurality of cleaved nucleic acid templates, each cleaved nucleic acid template comprising a cleaved end, comprising a variant of a PAM, and lacking at least a portion of the first target site. In some embodiments, the method further comprises (b) ligating the cleaved ends of the first cleavage composition with an oligonucleotide capture probe comprising a second detection sequence to obtain a first plurality of ligation products comprising the capture probe, comprising a variant of the PAM, comprising the first detection sequence, and lacking at least a portion of the target site.

In another aspect, the disclosure provides methods comprising the steps of: (a) incubating a library of variant nucleic acid templates with an RNA-guided endonuclease to obtain a first cleavage composition, (i) wherein each nucleic acid template comprises, in order from 5' to 3' or 3' to 5': a control target site for a control nuclease, a first target site for the RNA-guided endonuclease and a variant of a protospacer-adjacent motif adjacent to and 3' to the first target site, and a first detection sequence (ii) wherein the library is incubated with the RNA-guided endonuclease under conditions favorable for cleavage by the RNA-guided endonuclease, (iii) wherein the first cleavage composition comprises a first plurality of cleaved nucleic acid templates, each cleaved nucleic acid template comprising a cleaved end, comprising a variant of a PAM, and lacking at least a portion of the first target site; and a first plurality of uncleaved nucleic acid templates. In some embodiments, the method further comprises (b) incubating the first cleavage composition with the control nuclease under conditions to allow cleavage of the first plurality of uncleaved nucleic acid templates by the control nuclease, thereby obtaining a second cleavage composition comprising one or both of: (i) the first plurality of cleaved nucleic acid templates, and (ii) a second plurality of cleaved nucleic acid templates comprising a cleaved end and comprising the target site but lacking the control target site. In some embodiments, the method further comprises (c) ligating the cleaved ends of the second cleavage composition with an oligonucleotide capture probe comprising a second detection sequence to obtain (i) a first plurality of ligation products comprising the capture probe, a variant of the PAM, the first detection sequence, and lacking at least a portion of the target site; and (ii) a second plurality of ligation products comprising the capture probe, a variant of the PAM, the first detection sequence, the target site, and lacking at least a portion of the control target site. In some embodiments, the method further comprises a step of (d) determining the levels of the first and second pluralities of ligation products.

In some embodiments, the first detection sequence and/or the second detection sequence mediates capture by an oligonucleotide array and/or facilitates sequencing of the plurality of ligation products.

In another, the present disclosure provides methods comprising the steps of: (a) incubating a plurality of nucleic acid templates with a first nuclease and a guide RNA to obtain a first cleavage composition, (i) wherein the plurality of nucleic acid templates comprises a candidate target site for the guide RNA and a control target site for a control nuclease; (ii) wherein the plurality of nucleic acid templates are incubated with the first nuclease and the guide RNA under conditions favorable for cleavage by the first nuclease, and (iii) wherein the first cleavage composition comprises one or both of: a first plurality of cleaved nucleic acid templates comprising a cleaved end and lacking the control target site and lacking at least a portion of the candidate target site, and a first plurality of uncleaved nucleic acid templates. In some embodiments, the method further comprises (b) incubating the first cleavage composition with the control nuclease under conditions to allow cleavage of the first plurality of uncleaved nucleic acid templates by the control nuclease, thereby obtaining a second cleavage composition comprising one or both of: (i) the first plurality of cleaved nucleic acid templates, and (ii) a second plurality of cleaved nucleic acid templates comprising a cleaved end and comprising the candidate target site but lacking the control target site. In some embodiments, the method further comprises (c) ligating the cleaved ends of the second cleavage composition with an oligonucleotide capture probe to obtain a first plurality of ligation products comprising the capture probe and lacking at least a portion of the candidate target site, and a second plurality of ligation products comprising the capture probe and the candidate target site. In some embodiments, the method further comprises a step of (d) determining the levels of the first and second pluralities of ligation products.

In some embodiments, the capture probe comprises a first detection sequence. In some embodiments, the nucleic acid templates further comprise a second detection sequence. In some embodiments, the candidate target site is situated between the control target site and the second detection sequence, the first plurality of ligation products further comprise the second detection sequence, and the second plurality of ligation products further comprise the second detection sequence. In some embodiments, the first detection sequence and/or the second detection sequence mediates capture by an oligonucleotide array and/or facilitates sequencing of the plurality of ligation products. In some embodiments, the method further comprises a step of determining a relative abundance of the first and/or second pluralities of ligation products.

In some embodiments, the nucleic acid templates further comprise a protospacer adjacent motif (PAM) situated adjacent to the candidate target site. In some embodiments, the RNA-guided nuclease is Cas9.

In some embodiments, step (a) comprises contacting and/or incubating a library of variant nucleic acid templates with the first nuclease and the guide RNA. In some embodiments, each variant nucleic acid template comprises a variant of the candidate target site and a unique molecular identifier associated with the variant. In some embodiments, each nucleic acid template further comprises a second detection sequence. In some embodiments, the unique molecular identifier is situated between the variant of the candidate target site and the second detection sequence. In some embodiments, the first plurality of ligation products further comprise the second detection sequence and a unique molecular identifier. In some embodiments, the second plurality of ligation products further comprise the second detection sequence and a unique molecular identifier.

In some embodiments, the library comprises nucleic acid templates comprising fully degenerate sequence variants of the candidate target site. In some embodiments, the library comprises nucleic acid templates comprising less than fully degenerate sequence variants of the candidate target site. In some embodiments, the library comprises at least about $10^3$, $10^4$, $10^5$, $10^6$, or $10^7$ variant nucleic acid templates. In some embodiments, the library comprises about $10^3$, $10^4$, $10^5$, $10^6$, or $10^7$ variant nucleic acid templates. In some embodiments, the library comprises about $10^3$ to about $10^7$, or about $10^4$ to about $10^6$ variant nucleic acid templates.

In some embodiments, the method further comprising a step of detecting at least one unique molecular identifier associated with a first ligation product. In some embodiments, the method further comprises determining relative abundance of the first ligation product. In some embodiments, the method further comprises a step of detecting at least one unique molecular identifier associated with a second ligation product. In some embodiments, the method further comprises a step of identifying at least one variant associated with at least one unique molecular identifier present in either or both of the first and second plurality of ligation products.

In some embodiments, the method further comprises a step of amplifying the first and/or second plurality of ligation products. In some embodiments, the nucleic acid templates further comprise a second detection sequence. In some embodiments, the step of amplifying comprises performing an amplification reaction using amplification primers that recognize the first and second detection sequences.

In some embodiments, the method further comprises a step of sequencing the first and/or second plurality of ligation products.

In some embodiments, the control nuclease is a restriction enzyme. In some embodiments, the control target site is a restriction site corresponding to the restriction enzyme.

In some embodiments, the first plurality of cleaved nucleic acid templates comprises a blunt cleaved end. In some embodiments, the blunt end comprises a 5' phosphate group. In some embodiments, the second plurality of cleaved nucleic acid templates comprises a blunt cleaved end. In some embodiments, the blunt end comprises a 5' phosphate group.

In some embodiments, the control nuclease is a nuclease that produces a blunt end. In some embodiments, the first plurality of cleaved nucleic acid templates comprises a cohesive or sticky end. In some embodiments, the method further comprises a step of generating blunt ends from cohesive or sticky ends after step (a) and/or step (b). In some embodiments, the step of generating a blunt end comprises incubating the first cleavage composition from step (a) and/or the second cleavage composition from step (b) with a DNA polymerase. In some embodiments, the step of generating a blunt end comprises incubating the first cleavage composition from step (a) and/or the second cleavage composition from step (b) with an exonuclease.

In some embodiments, step (c) comprises ligating with a plurality of capture probes. In some embodiments, each capture probe comprises the same first detection sequence. In some embodiments, each capture probe further comprises a randomized barcode sequence.

In some embodiments, the method further comprises a step of analyzing, for the candidate target sequence, or for each variant of the candidate target sequence, the distribution of randomized barcode sequences present in the first and/or second plurality of ligation products. In some embodiments, the capture probe further comprises a Hamming code sequence.

In another aspect, the disclosure provides nucleic acid templates described herein. In some embodiments, a nucleic acid comprises, in order from 5' to 3' or 3' to 5': (i) a control target site for a control nuclease, (ii) a candidate target site for a first nuclease, (iii) a unique molecular identifier, and (iv) a detection sequence.

In some embodiments, the first nuclease is an RNA-guided endonuclease and wherein the nucleic acid further comprises a protospacer-adjacent motif (PAM) situated between the candidate target site and the unique molecular identifier.

In another aspect, the disclosure features a library described herein. In some embodiments, a library comprises variant nucleic acid templates, each nucleic acid template comprising, in order from 5' to 3' or 3' to 5': (i) a control target site for a control nuclease, (ii) a variant of a candidate target site for a first nuclease, (iii) a unique molecular identifier associated with the variant, and (iv) a detection sequence.

In some embodiments, the library comprises fully degenerate sequence variants of a candidate target site. In some embodiments, the library comprises less than fully degenerate sequence variants of the candidate target site. In some embodiments, the library comprises at least about $10^3$, $10^4$, $10^5$, $10^6$, or $10^7$ variant nucleic acid templates. In some embodiments, the library comprises about $10^3$, $10^4$, $10^5$, $10^6$, or $10^7$ variant nucleic acid templates. In some embodiments, the library comprises about $10^3$ to about $10^7$, or about $10^4$ to about $10^6$ variant nucleic acid templates.

In another aspect, the disclosure provides systems, e.g., systems for quantitative and/or qualitative characterization of cleavage profiles of nucleases, e.g., systems for use in a method described herein. In some embodiments, a system comprises a library of variant nucleic acid templates described herein. In some embodiments, the system further comprises a nuclease and a control nuclease described herein. In some embodiments, the system further comprises an oligonucleotide capture probe described herein.

At least some of the processes, methods, systems, and techniques described herein (including, but not limited to, computer-implemented processes for predicting guide-specific cleavage specificity) may be implemented as a computer program product that includes instructions that are stored on one or more non-transitory machine-readable storage media, and that are executable on one or more processing devices. Examples of non-transitory machine-readable storage media include, e.g., read-only memory, an optical disk drive, memory disk drive, random access memory, and the like. At least some of the processes, methods, systems, and techniques described herein may be implemented as an apparatus, method, or system that includes one or more processing devices and memory storing instructions that are executable by the one or more processing devices to perform stated operations.

BRIEF DESCRIPTION OF THE DRAWING

In FIG. 4A, three representative doubly mismatched targets were subjected to increasing doses of Guide 2 Cas9 RNP (SEQ ID NOS 28-31, respectively, in order of appearance). Rank ordering of the cleavage efficiency in individual testing is consistent with BLT-measured results. Amax represents the maximum sigmoidal fitted cleavage efficiency. In FIG. 4B, representative doubly mismatched targets from Guide 1 off-target data were subjected to increasing doses of Cas9 RNP (SEQ ID NOS 32-35, respectively, in order of appearance).

In FIG. 6A, average cleavage efficiency is graphed for all single mismatches across various targets. FIG. 6B shows that guides have unique GIMP scores when challenged with randomized off-targets. FIG. 6C shows that cleavage efficiency of a guide to its perfectly matched target does not correlate with GIMP score. GIMP score is graphed as a function of cleavage efficiency of the on-target. ($R^2=0.086$).

DEFINITIONS

Figure 1A:
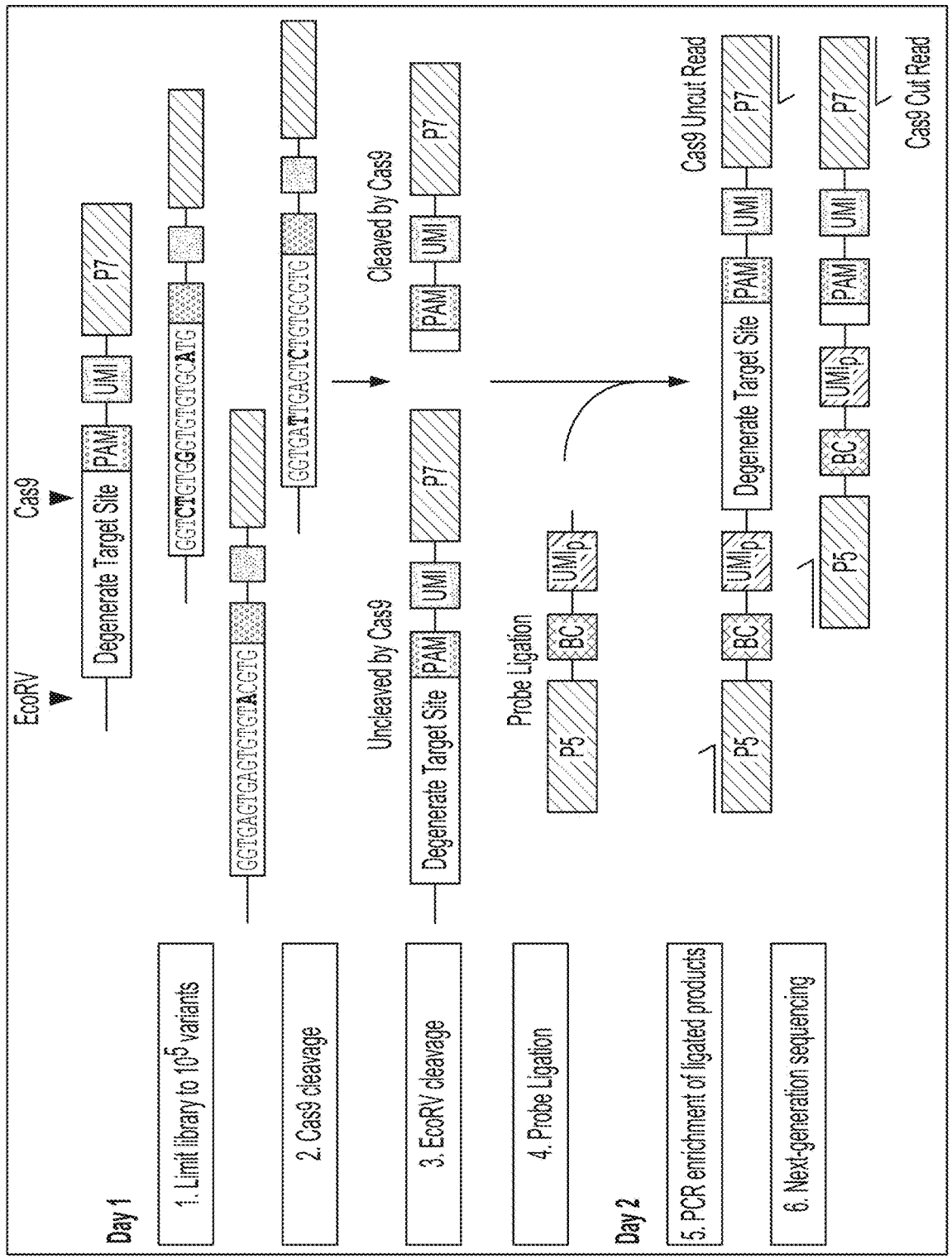
FIG. 1A depicts a schematic showing steps of an exemplary method of the present disclosure (SEQ ID NOS 25-27, respectively, in order of appearance).

Throughout the specification, several terms are employed that are defined in the following paragraphs. Other definitions may also found within the body of the specification. In this application, unless otherwise clear from context, (i) the term "a" may be understood to mean "at least one"; (ii) the term "or" may be understood to mean "and/or"; (iii) the terms "comprising" and "including" may be understood to encompass itemized components or steps whether presented by themselves or together with one or more additional components or steps; and (iv) the terms "about" and "approximately" may be understood to permit standard variation as would be understood by those of ordinary skill in the art; and (v) where ranges are provided, endpoints are included.

As used herein, the terms "about" and "approximately," in reference to a number, is used herein to include numbers that fall within a range of 20%, 10%, 5%, or 1% in either direction (greater than or less than) of the number unless otherwise stated or otherwise evident from the context (except where such number would exceed 100% of a possible value).

As used herein, the term "degenerate," when used to refer to an oligonucleotide or nucleotide sequence, refers to one or more positions which may contain any of a plurality of different bases. Degenerate residues within an oligonucleotide or nucleotide sequence are denoted by standard IUPAC nucleic acid notation, as shown below:

| Character | Degenerate Bases |
|---|---|
| K | G or T/U |
| M | A or C |
| R | A or G |
| Y | C or T/U |
| S | C or G |
| W | A or T/U |
| B | C, G or T/U |
| V | A, C or G |
| H | A, C or T/U |
| D | A, G or T/U |
| N | A, C, G or T/U |

Unless otherwise specified, a degenerate residue does not imply a random or equal distribution of possible bases, e.g., an "N" residue does not denote an equal distribution of A, C, G and/or T/U residues.

As used herein, the term "detecting" a nucleic acid molecule or fragment thereof refers to determining the presence of the nucleic acid molecule, typically when the nucleic acid molecule or fragment thereof has been fully or partially separated from other components of a sample or composition, and also can include determining the charge-to-mass ratio, the mass, the amount, the absorbance, the fluorescence, or other property of the nucleic acid molecule or fragment thereof.

As used herein, the term "heterologous," in reference to polypeptide domains, refers to the fact that the polypeptide domains do not naturally occur together (e.g., in the same polypeptide). For example, in fusion proteins generated by the hand of man, a polypeptide domain from one polypeptide may be fused to a polypeptide domain from a different polypeptide. The two polypeptide domains would be considered "heterologous" with respect to each other, as they do not naturally occur together.

The term "library", as used herein in the context of nucleic acids or proteins, refers to a population of two or more different nucleic acids or proteins, respectively. In some embodiments, a library comprises at least $10^1$, at least $10^2$, at least $10^3$, at least $10^4$, at least $10^5$, at least $10^6$, at least $10^7$, at least $10^8$, at least $10^9$, at least $10^{10}$, at least $10^{11}$, at least $10^{12}$, at least $10^{13}$, at least $10^{14}$, or at least $10^{15}$ different nucleic acid templates. In some embodiments, the members of the library may comprise randomized sequences, for example, fully or partially randomized sequences. In some embodiments, the library comprises nucleic acid molecules that are unrelated to each other, e.g., nucleic acids comprising fully randomized sequences. In other embodiments, at least some members of the library may be related, for example, they may be variants or derivatives of a particular sequence.

As used herein, the terms "ligation", "ligating", and grammatical equivalents thereof refer to forming a covalent bond or linkage between the termini of two or more nucleic acids, e.g., oligonucleotides and/or polynucleotides, typically in a template-driven reaction. The nature of the bond or linkage may vary widely and the ligation may be carried out enzymatically or chemically. As used herein, ligations are usually carried out enzymatically to form a phosphodiester linkage between a 5' carbon terminal nucleotide of one oligonucleotide with a 3' carbon of another nucleotide. The term "ligation" also encompasses non-enzymatic formation of phosphodiester bonds, as well as the formation of non-phosphodiester covalent bonds between the ends of oligonucleotides, such as phosphorothioate bonds, disulfide bonds, and the like.

As used herein, the term "nuclease" refers to a polypeptide capable of cleaving the phosphodiester bonds between the nucleotide subunits of nucleic acids; the term "endonuclease" refers to a polypeptide capable of cleaving the phosphodiester bond within a polynucleotide chain.

As used herein, the terms "nucleic acid", "nucleic acid molecule" or "polynucleotide" are used herein interchangeably. They refer to a polymer of deoxyribonucleotides or ribonucleotides in either single- or double-stranded form, and unless otherwise stated, encompass known analogs of natural nucleotides that can function in a similar manner as naturally occurring nucleotides. The terms encompass nucleic acid-like structures with synthetic backbones, as well as amplification products. DNAs and RNAs are both polynucleotides. The polymer may include natural nucleosides (i.e., adenosine, thymidine, guanosine, cytidine, uridine, deoxyadenosine, deoxythymidine, deoxyguanosine, and deoxycytidine), nucleoside analogs (e.g., 2-aminoadenosine, 2-thiothymidine, inosine, pyrrolo-pyrimidine, 3-methyl adenosine, C5-propynylcytidine, C5-propynyluridine, C5-bromouridine, C5-fluorouridine, C5-iodouridine, C5-methylcytidine, 7-deazaadenosine, 7-deazaguanosine, 8-oxoadenosine, 8-oxoguanosine, O(6)-methylguanine, and 2-thiocytidine), chemically modified bases, biologically modified bases (e.g., methylated bases), intercalated bases, modified sugars (e.g., 2'-fluororibose, ribose, 2'-deoxyribose, arabinose, and hexose), or modified phosphate groups (e.g., phosphorothioates and 5'-N-phosphoramidite linkages).

As used herein, the term "oligonucleotide" refers to a string of nucleotides or analogues thereof. Oligonucleotides may be obtained by a number of methods including, for example, chemical synthesis, restriction enzyme digestion or PCR. As will be appreciated by one skilled in the art, the length of an oligonucleotide (i.e., the number of nucleotides) can vary widely, often depending on the intended function or use of the oligonucleotide. Generally, oligonucleotides comprise between about 5 and about 300 nucleotides, for example, between about 15 and about 200 nucleotides, between about 15 and about 100 nucleotides, or between about 15 and about 50 nucleotides. Throughout the specification, whenever an oligonucleotide is represented by a sequence of letters (chosen from the four base letters: A, C, G, and T, which denote adenosine, cytidine, guanosine, and thymidine, respectively), the nucleotides are presented in the 5' to 3' order from the left to the right. In certain embodiments, the sequence of an oligonucleotide includes one or more degenerate residues described herein.

As used herein, the term "polypeptide" generally has its art-recognized meaning of a polymer of amino acids. The term is also used to refer to specific functional classes of polypeptides, such as, for example, nucleases, antibodies, etc.

As used herein, the term "target site," refers to a nucleic acid sequence that defines a portion of a nucleic acid to which a binding molecule will bind, provided sufficient conditions for binding exist. In some embodiments, a target site is a nucleic acid sequence to which a nuclease described herein binds and/or that is cleaved by such nuclease. In some embodiments, a target site is a nucleic acid sequence to which a guide RNA described herein binds. A target site may be single-stranded or double-stranded. In the context of nucleases that dimerize, for example, nucleases comprising a FokI DNA cleavage domain, a target site typically comprises a left-half site (bound by one monomer of the nuclease), a right-half site (bound by the second monomer of the nuclease), and a spacer sequence between the half sites in which the cut is made. In some embodiments, the left-half site and/or the right-half site is between 10-18 nucleotides long. In some embodiments, either or both half-sites are shorter or longer. In some embodiments, the left and right half sites comprise different nucleic acid sequences. In the context of zinc finger nucleases, target sites may, in some embodiments, comprise two half-sites that are each 6-18 bp long flanking a non-specified spacer region that is 4-8 bp long. In the context of TALENs, target sites may, in some embodiments, comprise two half-sites sites that are each 10-23 bp long flanking a non-specified spacer region that is 10-30 bp long. In the context of RNA-guided (e.g., RNA-programmable) nucleases, a target site typically comprises a nucleotide sequence that is complementary to a guide RNA of the RNA-programmable nuclease, and a protospacer adjacent motif (PAM) at the 3' end or 5' end adjacent to the guide RNA-complementary sequence. For the RNA-guided nuclease Cas9, the target site may be, in some embodiments, 16-24 base pairs plus a 3-6 base pair PAM (e.g., NNN, wherein N represents any nucleotide). Exemplary target sites for RNA-guided nucleases, such as Cas9, are known to those of skill in the art and include, without limitation, NNG, NGN, NAG, and NGG, wherein N represents any nucleotide. In addition, Cas9 nucleases from different species (e.g., *S. thermophilus* instead of *S. pyogenes*) recognizes a PAM that comprises the sequence NGGNG. Additional PAM sequences are known, including, but not limited to NNA-GAAW and NAAR (see, e.g., Esvelt and Wang, Molecular Systems Biology, 9:641 (2013), the entire contents of which are incorporated herein by reference). For example, the target site of an RNA-guided nuclease, such as, e.g., Cas9, may comprise the structure [Nz]-[PAM], where each N is, independently, any nucleotide, and z is an integer between 1 and 50. In some embodiments, z is at least 2, at least 3, at least 4, at least 5, at least 6, at least 7, at least 8, at least 9, at least 10, at least 11, at least 12, at least 13, at least 14, at least 15, at least 16, at least 17, at least 18, at least 19, at least 20, at least 25, at least 30, at least 35, at least 40, at least 45, or at least 50. In some embodiments, z is 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50. In some embodiments, Z is 20.

As used herein, the term "variant" refers to an entity that shows significant structural identity with a reference entity but differs structurally from the reference entity in the presence or level of one or more chemical moieties as compared with the reference entity. In many embodiments, a variant also differs functionally from its reference entity. In general, whether a particular entity is properly considered to be a "variant" of a reference entity is based on its degree of structural identity with the reference entity. As will be appreciated by those skilled in the art, any biological or chemical reference entity has certain characteristic structural elements. A variant, by definition, is a distinct chemical entity that shares one or more such characteristic structural elements. To give but a few examples, a polypeptide may have a characteristic sequence element comprising a plurality of amino acids having designated positions relative to one another in linear or three-dimensional space and/or contributing to a particular biological function; a nucleic acid may have a characteristic sequence element comprised of a plurality of nucleotide residues having designated positions relative to on another in linear or three-dimensional space. For example, a variant polypeptide may differ from a reference polypeptide as a result of one or more differences in amino acid sequence and/or one or more differences in chemical moieties (e.g., carbohydrates, lipids, etc.) covalently attached to the polypeptide backbone. In some embodiments, a variant polypeptide shows an overall sequence identity with a reference polypeptide (e.g., a nuclease described herein) that is at least 60%, 65%, 70%, 75%, 80%, 85%, 86%, 87%, 88%, 89%, 90%, 91%, 92%, 93%, 94%, 95%, 96%, 97%, or 99%. Alternatively or additionally, in some embodiments, a variant polypeptide does not share at least one characteristic sequence element with a reference polypeptide. In some embodiments, the reference polypeptide has one or more biological activities. In some embodiments, a variant polypeptide shares one or more of the biological activities of the reference polypeptide, e.g., nuclease activity. In some embodiments, a variant polypeptide lacks one or more of the biological activities of the reference polypeptide. In some embodiments, a variant polypeptide shows a reduced level of one or more biological activities (e.g., nuclease activity) as compared with the reference polypeptide. In some embodiments, a polypeptide of interest is considered to be a "variant" of a parent or reference polypeptide if the polypeptide of interest has an amino acid sequence that is identical to that of the parent but for a small number of sequence alterations at particular positions. Typically, fewer than 20%, 15%, 10%, 9%, 8%, 7%, 6%, 5%, 4%, 3%, 2% of the residues in the variant are substituted as compared with the parent. In some embodiments, a variant has 10, 9, 8, 7, 6, 5, 4, 3, 2, or 1 substituted residue as compared with a parent. Often, a variant has a very small number (e.g., fewer than 5, 4, 3, 2, or 1) number of substituted functional residues (i.e., residues that participate in a particular biological activity). Furthermore, a variant typically has not more than 5, 4, 3, 2, or 1 additions or deletions, and often has no additions or deletions, as compared with the parent. Moreover, any additions or deletions are typically fewer than about 25, about 20, about 19, about 18, about 17, about 16, about 15, about 14, about 13, about 10, about 9, about 8, about 7, about 6, and commonly are fewer than about 5, about 4, about 3, or about 2 residues. In some embodiments, the parent or reference polypeptide is one found in nature.

DETAILED DESCRIPTION OF CERTAIN EMBODIMENTS

The present disclosure provides, among other things, systems and methods for assessing cleavage profiles of nucleases using artificial targets, nucleic acid templates, and libraries of variant nucleic acid templates.

Some existing screening methods for evaluating potential off-target sites are limited to evaluating genomic DNA and require whole-genome sequencing, which is costly and difficult to use. Some methods use a catalytically inactive nuclease to assess binding at various sites, which therefore does not allow a true assessment of actual cleavage at those sites. Some methods rely on an enrichment step, such as a step that enriches for cleaved targets, which may complicate or prevent the quantitative assessment of relative cleavage frequencies at various off-target sites.

In addition, existing screening methods typically only assess whether a given off-target site is cleaved at all, and give no indication as to the extent of cleavage at the off-target site. Presently disclosed methods circumvent one or more of the afore-mentioned problems. Thus, the present disclosure provides, at least in part, a high-throughput method to measure off-target cleavage events and/or rates. In some embodiments, an off-target profile may be used to inform gRNA or protein (e.g., targeted nuclease) selection in order to minimize potential off-target cleavage.

Methods

Assessing Cleavage of Target Sites by Nucleases

In one aspect, the present disclosure provides methods of assessing cleavage of nucleic acid sequences (e.g., putative or candidate target sites) by one or more nucleases. In certain embodiments, provided methods allow not only assessment of whether a nucleic acid sequence (e.g., a putative or candidate target site) is cleaved by a nuclease, but also provides analysis of the extent to which a given target site is cleaved. For example, in certain embodiments, whether and/or the extent to which a putative or candidate target site is cleaved is assessed by detecting cleaved and/or uncleaved nucleic acid templates. In some embodiments, assessing both cleaved and uncleaved nucleic acid templates allows for determination of the relative abundances of cleaved and uncleaved nucleic acid templates with a given candidate target site, and, in some such embodiments, the relative rates and/or frequencies with which such templates are cleaved.

In some embodiments, methods of the disclosure generally comprise producing or providing a library of nucleic acid templates that comprise a candidate target site (e.g., degenerate target sites) for a nuclease (e.g., Cas9) and a control target site for a control nuclease (e.g., EcoRV). An exemplary, nonlimiting method is schematically depicted in FIG. 1A, and not all features depicted in FIG. 1A are present and/or used in all systems and/or all methods of the disclosure. In the method depicted in FIG. 1A, the nucleic acid templates include a control target site for EcoRV, which is 5' of a degenerate target site for Cas9. The library is contacted with the nuclease and subjected to conditions that allow cleavage by the nuclease, e.g., at or near one or more candidate target sites. As depicted in FIG. 1A, cleavage by the nuclease results in a cleaved nucleic acid template that lacks the control target site and at least a portion of the degenerate target site. Thus, contacting the library with the nuclease results in a first composition (e.g., a first cleavage composition) that includes at least one cleaved nucleic acid template (e.g., a first plurality of cleaved nucleic acid templates) having a cleaved end and lacking both the control target site and at least a portion of the degenerate target site. The first composition also includes at least one uncleaved nucleic acid template (i.e., a nucleic acid template not cleaved by the nuclease, and which includes both the control target site and the degenerate target site). Upon contacting the first composition (e.g., including at least one cleaved nucleic acid template (i.e., cleaved by the nuclease) and at least one uncleaved nucleic acid template) with the control nuclease, the control target site (present on uncleaved nucleic acid template) is cleaved by the control nuclease, resulting in a second composition. Such second composition includes (i) at least a first cleaved nucleic acid template cleaved by the nuclease (and lacking the control target site and at least a portion of the degenerate target site) and (ii) at least a second cleaved nucleic acid template cleaved by the control nuclease (i.e., which was not cut by the initial nuclease), and which includes the degenerate target site.

In some embodiments, the first and/or second cleaved nucleic acid templates can be detected, and the presence of one or both can be used to assess whether (and, in some embodiments, the extent to which) the nuclease cleaves a degenerate target site. In some embodiments, detection is performed using an oligonucleotide capture probe described herein. For example, an oligonucleotide capture probe can be ligated to the cleaved ends of the first and second cleaved nucleic acid templates, e.g., to produce ligation products. In some embodiments, such ligation products include (i) at least one ligation product that includes the oligonucleotide capture probe and a portion of the nucleic acid template lacking the control target site and lacking at least a portion of the degenerate target site (e.g., "Cas9 Cut" in FIG. 1A), and (ii) at least one ligation product that includes the oligonucleotide capture probe and a portion of the nucleic acid template that includes the degenerate target site and that lacks the control target site (e.g., "Cas9 uncut" in FIG. 1A). Exemplary ligation products are depicted at the bottom of FIG. 1A. In some embodiments, the oligonucleotide capture probe includes a first detection sequence (e.g., a first sequencing adapter, e.g., "P5" depicted in FIG. 1A) and the nucleic acid template includes a second detection sequence (e.g., a second sequencing adapter, e.g., "P7" depicted in FIG. 1A). As depicted in FIG. 1A, in some embodiments, the first and second sequencing adapters can be used to sequence the different ligation products.

In some embodiments, as shown in FIG. 1A, each nucleic acid template includes and is associated with a unique molecular identifier ("UMI") described herein. In some embodiments, as shown in FIG. 1A, the oligonucleotide capture probe includes a randomized barcode ("BC") described herein. In some embodiments, a cut rate for a nuclease can be calculated by: (1) associating each UMI with a target site variant described herein (e.g., using just uncut (i.e., long) reads (e.g., detection of "Cas9 Uncut Read" in FIG. 1A); (2) collapsing reads by BC to avoid PCR bias; and (3) for each UMI, calculating a cut rate from short reads (e.g., detection of "Cas9 Cut Read" in FIG. 1A) over total reads. In some embodiments, for a plurality of target site variants, cut rate is calculated as the overage over its UMIs (e.g., filtered by BC read count).

In some embodiments, the method involves:
(a) incubating a plurality of nucleic acid templates with a first nuclease to obtain a first cleavage composition,
  (i) wherein the plurality of nucleic acid templates comprises a candidate target site for the first nuclease and a control target site for a control nuclease;
  (ii) wherein the plurality of nucleic acid templates are incubated with the first nuclease under conditions favorable for cleavage by the first nuclease, and
  (iii) wherein the first cleavage composition comprises one or both of:
    a first plurality of cleaved nucleic acid templates comprising a cleaved end and lacking the control target site and lacking at least a portion of the candidate target site, and
    a first plurality of uncleaved nucleic acid templates;
(b) incubating the first cleavage composition with the control nuclease under conditions to allow cleavage of the first plurality of uncleaved nucleic acid templates by the control nuclease, thereby obtaining a second cleavage composition comprising one or both of:
  (i) the first plurality of cleaved nucleic acid templates, and
  (ii) a second plurality of cleaved nucleic acid templates comprising a cleaved end and comprising the candidate target site but lacking the control target site; and
(c) ligating the cleaved ends of the second cleavage composition with an oligonucleotide capture probe to obtain a first plurality of ligation products comprising the capture probe and lacking at least a portion of the candidate target site, and a second plurality of ligation products comprising the capture probe and the candidate target site.

In some embodiments, cleavage of target sites is assessed using a library of variant nucleic acid templates. In some embodiments, each variant nucleic acid template comprises a variant of a candidate target site and, optionally, a unique molecular identifier (UMI; as further described herein) associated with the variant.

In some embodiments, each nucleic acid template further comprises a detection sequence (as further described herein), with the unique molecular identifier situated between the variant of the candidate target site and the second detection sequence. Thus, upon incubating the library with the nuclease and the control nuclease, followed by ligation with an oligonucleotide capture probe as described above, first and second pluralities of ligation products are generated that comprise a detection sequence and unique molecular identifier.

In some embodiments, one or more unique molecular identifiers is detected, e.g., one or more unique identifiers in the first and/or second pluralities of ligation products. For example, in some instances, one or more unique identifiers associated with a variant nucleic acid template is identified based on detection of the one or more unique identifiers in the first and/or second pluralities of ligation products. In some embodiments, an abundance of the first plurality of ligation products is determined. In some embodiments, an abundance of the second plurality of ligation products is determined, as described herein.

For example, in some embodiments, provided are methods involving steps of:

(a) incubating a library of variant nucleic acid templates with a first nuclease to obtain a first cleavage composition,
  (i) wherein each nucleic acid template comprises, in order from 5' to 3' or 3' to 5':
    a control target site for a control nuclease,
    a variant target site for the first nuclease,
    a unique molecular identifier associated with the variant target site, and
    a first detection sequence,
  (ii) wherein the library is incubated with the first nuclease under conditions favorable for cleavage by the first nuclease, and
  (iii) wherein the first cleavage composition comprises one or both of:
    a first plurality of cleaved nucleic acid templates comprising a cleaved end, lacking the control target site, and lacking at least a portion of the candidate target site, and
    a first plurality of uncleaved nucleic acid templates;
(b) incubating the first cleavage composition with the control nuclease under conditions to allow cleavage of the first plurality of uncleaved nucleic acid templates by the control nuclease, thereby obtaining a second cleavage composition comprising one or both of:
  (i) the first plurality of cleaved nucleic acid templates, and
  (ii) a second plurality of cleaved nucleic acid templates comprising a cleaved end and comprising the candidate target site but lacking the control target site;
(c) ligating the cleaved ends of the second cleavage composition with an oligonucleotide capture probe comprising a second detection sequence to obtain:
  (i) a first plurality of ligation products comprising the capture probe and lacking at least a portion of the candidate target site, and
  (ii) a second plurality of ligation products comprising the capture probe and the candidate target site; and
(d) determining relative abundance of at least one unique molecular identifier associated with a first ligation product and/or a second ligation product.

In some embodiments, cleavage of a nucleic acid template by a nuclease generates a cleaved end with an overhang, a so-called "cohesive" or "sticky end". In some such embodiments, methods comprise a step of blunting an overhang to generate a blunt cleaved end. Such a step can be performed, for example, any time after the step of incubating the plurality of nucleic acid templates or library of variant nucleic acid templates with the nuclease and before the step of ligating the cleaved ends of a cleavage composition with an oligonucleotide capture probe.

Methods of blunting 5' or 3' overhangs are known in the art. For example, a 5' overhang can blunted by filling in using a 5' to 3' DNA polymerase (such as T4 DNA polymerase or DNA polymerase I) or a fragment thereof (such as the Klenow fragment of DNA polymerase I). As another example, a 5' overhang can be blunted using a 5' to 3' exonuclease (such as Mung Bean nuclease) or a fragment thereof. As another example, a 3' overhang can be blunted using a 3' to 5' exonuclease or a fragment thereof.

Assessing PAM Sites

In some embodiments, the nuclease whose profile is being assessed is a nuclease that requires a matching protospacer-adjacent motif (PAM) adjacent to the target site for cleavage to occur. For example, many RNA-guided endonucleases, such as CRISPR-associated nucleases, require the presence of a matching PAM to cleave.

In some embodiments, an appropriate PAM site(s) for a particular nuclease requiring a PAM can be determined. In some embodiments, a particular RNA-guided endonuclease is incubated with a library of variant nucleic acid templates, in which each variant nucleic acid template comprises a fixed target site for the nuclease, and a variant of a PAM adjacent to and 3' to the fixed target site. In some embodiments, each nucleic acid template further comprises a detection sequence that is either 3' to the variant of the PAM or 5' to the fixed target site.

In some embodiments, the incubation produces a first cleavage composition that includes a first plurality of cleaved nucleic acid templates, where each cleaved nucleic acid template comprises (i) a cleaved end; (ii) a variant of a PAM, and wherein each cleaved nucleic acid template lacks at least a portion of the target site. Upon ligation of the cleaved ends with an oligonucleotide capture probe, a first plurality of ligation products comprising (i) the capture probe, (ii) a variant of the PAM; (iii) the first detection sequence, and lacking at least a portion of the target site.

Each nucleic acid template may or may not include a unique molecular identifier. As the PAM itself is not cleaved, a unique molecular identifier may or may not be used to recover the identity of a PAM that is compatible with cleavage.

For example, in some embodiments, provided are methods involving steps of: (a) incubating a library of variant nucleic acid templates with an RNA-guided endonuclease to obtain a first cleavage composition, (i) wherein each nucleic acid template comprises: a first target site for the RNA-guided endonuclease, a variant of a protospacer-adjacent motif (PAM) adjacent to and 3' to the first target site, and a detection sequence (ii) wherein the library is incubated with the RNA-guided endonuclease under conditions favorable for cleavage by the RNA-guided endonuclease, (iii) wherein the first cleavage composition comprises a first plurality of cleaved nucleic acid templates, each cleaved nucleic acid template comprising a cleaved end, comprising a variant of a PAM, and lacking at least a portion of the first target site; and (b) ligating the cleaved ends of the first cleavage composition with an oligonucleotide capture probe comprising a second detection sequence to obtain a first plurality of ligation products comprising the capture probe, comprising a variant of the PAM, comprising the first detection sequence, and lacking at least a portion of the target site.

In some embodiments, a control nuclease is used to cleave variant nucleic acid templates that are not cleaved by the nuclease being assessed. For example, in some embodiments, provided are methods involving steps of: (a) incubating a library of variant nucleic acid templates with an RNA-guided endonuclease to obtain a first cleavage composition, (i) wherein each nucleic acid template comprises, in order from 5' to 3' or 3' to 5': a control target site for a control nuclease, a first target site for the RNA-guided endonuclease and a variant of a protospacer-adjacent motif adjacent to and 3' to the first target site, and a first detection sequence, (ii) wherein the library is incubated with the RNA-guided endonuclease under conditions favorable for cleavage by the RNA-guided endonuclease, (iii) wherein the first cleavage composition comprises a first plurality of cleaved nucleic acid templates, each cleaved nucleic acid template comprising a cleaved end, comprising a variant of a PAM, and lacking at least a portion of the first target site;

and a first plurality of uncleaved nucleic acid templates; (b) incubating the first cleavage composition with the control nuclease under conditions to allow cleavage of the first plurality of uncleaved nucleic acid templates by the control nuclease, thereby obtaining a second cleavage composition comprising one or both of: (i) the first plurality of cleaved nucleic acid templates, and (ii) a second plurality of cleaved nucleic acid templates comprising a cleaved end and comprising the target site but lacking the control target site; (c) ligating the cleaved ends of the second cleavage composition with an oligonucleotide capture probe comprising a second detection sequence to obtain (i) a first plurality of ligation products comprising the capture probe, a variant of the PAM, the first detection sequence, and lacking at least a portion of the target site; and (ii) a second plurality of ligation products comprising the capture probe, a variant of the PAM, the first detection sequence, the target site, and lacking at least a portion of the control target site.

Nucleic Acid Templates

In some embodiments, methods of the present disclosure involve nucleic acid templates. In some embodiments, nucleic acid templates are modular, comprising one or more of the following nucleotide sequence components: a target site (or candidate target site) for a nuclease described herein; a control target site for a control nuclease described herein; a unique molecular identifier described herein; and a detection sequence described herein. Nucleic acid templates are not limited to any particular order of such components (i.e., 5' to 3' of a nucleic acid), and the disclosure is not limited to particular exemplary nucleic acid templates described herein. Production of nucleic acid templates for use in methods of disclosure are within the skill of those in the art.

In some embodiments, a nucleic acid template comprises (i) a control target site for a control nuclease, and (ii) a candidate target site for a nuclease whose cleavage profile is being assayed.

In some embodiments, a nucleic acid template further comprises a detection sequence situated, e.g., on the side of the candidate target site that is distal to the control target site (such that the candidate target site is between the control target site and the detection sequence).

In some embodiments, for example, in which a method of the disclosure involves more than one variant nucleic acid template, a nucleic acid template further comprises one or more unique molecular identifiers that is associated with the variant.

For example, in some embodiments, a nucleic acid template includes, in order from 5' to 3' or from 3' to 5': (i) a control target site for a control nuclease, (ii) a variant target site for a nuclease, (iii) a unique molecular identifier associated with the variant target site, and (iv) a detection sequence.

In some embodiments, a nucleic acid template further comprises a protospacer adjacent motif (PAM), e.g., adjacent to and 3' to the candidate target site for the first nuclease or the variant target site for the first nuclease.

In some embodiments, a nucleic acid template comprises, (i) a target site for nuclease (the nuclease whose cleavage profile is being assayed), (ii) a PAM adjacent and 3' to the target site, and (iii) a detection sequence situated either 5' to the target site or 3' to the PAM.

In some embodiments, a nucleic acid template comprises one or more spacer sequences, e.g., one or more spacer sequences between, 5' to, or 3' to, one or more of the components described herein. Such spacer sequences may, for example, serve to insulate components, provide sites to which amplification and/or sequencing primers can bind, and/or bring the total size of a nucleic acid template to a desirable size.

Detection Sequences

Detection sequences, as used herein, refer to sequence elements that may be present on a nucleic acid template and that facilitate recovery and/or detection of nucleic acids, or nucleic acid fragments, containing them. In some embodiments, one or more detection sequences facilitate or mediate capture by an oligonucleotide array and/or facilitate or mediate sequencing, e.g., sequencing of ligation products described herein.

In some embodiments, detection sequences facilitate amplification and/or sequencing. In some embodiments, detection sequences comprise one or more sequences that can be recognized by amplification and/or sequencing primers.

For example, in some embodiments, detection sequences comprise a sequence adapter for use in a sequencing method. In some embodiments, such sequence adapters comprise an amplification primer binding site and a sequencing primer binding site. In some embodiments, such sequence adapters comprising a primer binding site that serves as both an amplification and sequencing primer binding site. In some embodiments, the amplification primer binding site overlaps with the sequencing primer binding site.

In some embodiments, the amplification primer binding site is used for long-range amplification.

In some embodiments, sequence adapters further comprise a marker sequence that marks one end of the adapter.

In some embodiments, sequence adapters further comprise a barcode sequence.

Detection sequences that can be used in the methods described herein are known in the art. For example, sequencing adapters (e.g., MiSeq adapters) (available from Illumina) can be used as detection sequences.

Unique Molecular Identifiers

In some embodiments, a nucleic acid template can include a unique molecular identifiers (abbreviated as "UMIs" herein). UMIs refer to sequences that can be used to retrieve information about a nucleic acid template, a variant nucleic acid template, or a portion thereof. For example, in methods of the disclosure involving multiple nucleic acid templates each containing a variant target site for the nuclease, each UMI may be associated with a particular variant target site, which itself may be destroyed by cleavage by a nuclease.

When a UMI is present on a nucleic acid template containing a detection sequence, it is generally positioned within the nucleic acid template such that, after cleavage by the nuclease and/or control nuclease, the UMI is present and intact on the fragment containing the detection sequence. For example, in some embodiments, the UMI is positioned between a candidate target site and a detection sequence. In some such embodiments, detection of the detection sequence can be used to identify a particular UMI and, e.g., to identify the target site associated with the particular UMI.

In some embodiments, the UMI is a randomly generated sequence.

The size of the UMI in various embodiments may vary. If a library is used, the size of the library and/or the particular protocols and reagents used to generate the library may influence the size of the UMI. For example, in some embodiments, the UMI is n nucleotides long, where 4' is larger than the number of variants in the library. In some embodiments, n is much larger than it needs to be to cover the number of variants in the library.

In some embodiments, the UMI is between eight and 20 nucleotides in length, for example, between 10 and 16 nucleotides in length, such as 10, 11, 12, 13, 14, 15, and 16 nucleotides in length. The production and use of UMIs in various contexts are known in the art.

Oligonucleotide Capture Probes

In some embodiments described herein, oligonucleotide capture probes are used to bind to and/or ligate nucleic acid templates or cleavage products obtained from nucleic acid templates. In some embodiments, an oligonucleotide capture probe comprises a detection sequence described herein. In some embodiments, an oligonucleotide capture probe comprises a detection sequence at or near one terminal end. In some embodiments, an oligonucleotide capture probe comprises a detection sequence at or near one terminal end, which is opposite a "capture end" distal to the terminal end comprising a detection sequence. The capture end of the oligonucleotide probe may interact with a nucleic acid fragment intended to be captured. For example, in some embodiments, the oligonucleotide capture probe is ligated to another nucleic acid at or near the capture end.

In some embodiments, oligonucleotide capture probes are double-stranded. In some such embodiments, oligonucleotide capture probes comprise at least one blunt end that serves as the capture end. In some embodiments, the at least one blunt end comprises a 5' phosphate.

In some embodiments, oligonucleotide capture probes are double stranded and comprise an overhang, e.g., a 5' or a 3' overhang at the capture end. In some embodiments, the overhang is at least partially complementary to the overhang that results from cleavage from a nuclease whose cleavage profile is being assayed.

In some embodiments, an oligonucleotide capture probe comprises one or more additional sequences, such as one or more random barcode. In some embodiments, random barcodes are not associated with any particular sequence and may be used, e.g., for quality control purposes. For example, in analyzing ligation products comprising an oligonucleotide capture probe comprising a random barcode, the random barcode can be used to assess amplification bias of a particular ligation product. The over- or under representation of a given random barcode among amplification products may indicate amplification bias. In some embodiments, data associated with such biased amplification products is excluded.

Suitable sizes for the random barcode may vary depending on the embodiment. By way of non-limiting example, in some embodiments, the random barcode is 2, 3, 4, 5, 6, 7, 8, 9, 10, 11, or 12 nucleotides in length.

In some embodiments, an oligonucleotide capture probe comprises one or more Hamming codes, i.e., an error-correcting barcodes. Hamming codes are sequences that can be used, for example, to identify a particular sample when samples are multiplexed. In some embodiments, there are collectively a defined number of possible Hamming codes, such as, by way of non-limiting example, up to 2, 3, 4, 5, 6, 7, 8, 9, 10, 11, 12, 13, 14, 15, 16, 17, 18, 19, or 20 possible Hamming codes.

In some embodiments, in a method as described herein, a plurality of oligonucleotide capture probes each comprising a random barcode, a Hamming code, or both is ligated to cleaved ends of a cleavage composition. In some embodiments in which the plurality of oligonucleotide capture probes comprise a random barcode, the distribution of randomized barcodes present in the first and/or second plurality of ligation products is analyzed for each variant nucleic acid template.

In some embodiments, oligonucleotide capture probes comprise both a detection sequence and a random barcode. In some embodiments, oligonucleotide capture probes comprise a detection sequence, a Hamming code, and a random barcode.

In some embodiments, an oligonucleotide capture probe is any suitable length to enable ligation to a cleavage product described herein, and optionally identification using a detection sequence described herein. In some embodiments, an oligonucleotide capture probe is about 25, 50, 75, 100, 125, 150, 175, 200, 225, 250, 275, 300, or more, nucleotides in length.

Libraries of Variant Nucleic Acid Templates

In some embodiments, libraries of variant nucleic acid templates are used in the presently disclosed methods. Generally, variant nucleic acid templates comprise a variant portion and a non-variant portion.

In some embodiments, libraries are "barcoded" in that each variant is associated with a unique molecular identifier (UMI), which can be used to retrieve information about the variant portion of the nucleic acid template. For example, if the nucleic acid templates in a library vary in the target site for the nuclease, each UMI be can associated with a particular variant target site, which may be destroyed by cleavage during analysis of a nuclease's cleavage profile.

In some embodiments, provided are libraries of variant nucleic acid templates, each nucleic acid template includes, in order from 5' to 3' or 3' to 5':
(i) a control target site for a control nuclease, (ii) a variant of a candidate target site for a first nuclease, (iii) a unique molecular identifier associated with the variant, and (iv) a detection sequence.

For example, the above-mentioned libraries can be used in methods of assessing possible cleavage activity at candidate target sites.

In some embodiments, libraries are not barcoded. For example, in some methods described herein, the variant portion of the nucleic acid template would remain intact throughout any method of assessing nuclease cleavage profiles, so no barcode is needed.

In some embodiments, the nuclease whose profile is being assessed requires a matching protospacer-adjacent motif (PAM) adjacent to the target site for cleavage to occur. For example, many RNA-guided endonucleases, such as CRISPR-associated nucleases, require the presence of a matching PAM to cleave.

In some embodiments, libraries of potential PAM sites are used, e.g., in methods to determine the correct PAM sequence(s) for a given nuclease. For example, libraries used in these methods may comprise of variant nucleic acid templates, each comprising: a fixed target site for an RNA-guided endonuclease, a variant of a protospacer-adjacent motif adjacent to and 3' to the fixed target site, and a detection sequence that is either 3' to the variant of the PAM or 5' to the fixed target site. As the PAM itself is not cleaved, no barcode is required to recover the identity of a PAM that is compatible with cleavage.

In some embodiments, variant nucleic acid templates further comprise a control target site (for a control nuclease) that is located on the side of the fixed target site and PAM that is distal to the detection sequence (i.e., either 5' to the target site if the detection sequence is 3' to the variant of the PAM, or 3' to the variant of the PAM if the detection sequence is 5' to the fixed target site).

In some embodiments, libraries comprise degenerate sequences at the variant portion of the nucleic acid template (e.g., the target site and/or the PAM, if present). In some embodiments, libraries are fully degenerate in the variant portion of the nucleic acid template.

By "fully degenerate," it is meant that the degenerate sequence includes all possible nucleotides or nucleotide sequences at the variant portion of the nucleic acid template.

Generally, "all possible nucleotides" refers to the four standard nucleotides for the appropriate nucleic acid. For deoxyribonucleic acids, the four standard deoxyribonucleotides are deoxyadenylate, deoxyguanylate, deoxythmyidylate, and deoxycytidylate. For ribonucleic acids, the four standard ribonucleotides are adenylate, guanylate, uridylate, and cytidylate. In some embodiments, non-standard nucleotides are used in addition to or instead of standard nucleotides; thus the number of possible nucleotides at a given position may be more than four.

In some embodiments in which the variant portion of the nucleic acid template is fully degenerate, at any given position within the variant portion, there is an approximately equal probability of the nucleotide being any one of the (typically four) possible nucleotides.

In some embodiments in which the variant portion of the nucleic acid template is fully degenerate, at any given position within the variant portion, there is not an approximately equal probability of the nucleotide being any one of the (typically four) possible nucleotides. In some embodiments, the fully degenerate sequence is biased toward a given sequence. For example, in some embodiments in which the variant portion is a variant of a known wild-type or canonical sequence, the fully degenerate sequence is biased toward that wild-type or canonical sequence.

In some embodiments, libraries comprise less than fully degenerate sequences at the portion of the nucleic acid template that varies. For example, in some embodiments, the candidate target site is sufficiently long that a fully degenerate library may contain too many variants to allow a practical and/or meaningful analysis. In some embodiments, the library that is used in methods of the invention is bottlenecked from a larger library (such as a library that comprises fully degenerate sequences at the variant portion of the nucleic acid template).

The bottlenecked library can contain a number of variants that can be practically analyzed in possible downstream steps, e.g., deep sequencing, while still being large enough to ensure adequate coverage of possible candidate target sites. For example, in some embodiments, bottlenecked libraries contain on the order of approximately $10^3$, $10^4$, $10^5$, $10^6$ or $10^7$ variants. In some embodiments, bottlenecked libraries contain on the order of approximately $10^5$ variants, e.g., $10^5$, $2\times10^5$, $3\times10^5$, $4\times10^5$, $5\times10^5$, $6\times10^5$, $7\times10^5$, $8\times10^5$, or $9\times10^5$.

In some embodiments, bottlenecking is performed by diluting a sample of the bottlenecked library and taking a portion of the diluted sample as the bottlenecked library.

In some embodiments, bottlenecking reduces the total number of nucleic acid templates, but maintains substantially the same proportion of unique nucleic acid templates present in the original library. In some embodiments, the complexity of the library is limited and/or sequence variant species are not equally represented within the library.

In some embodiments, libraries used in presently disclosed methods are synthesized according to any suitable method known in the art (see, e.g., http://blog.allelebiotech.com/tag/degenerate-oligos/). In some embodiments, sequence information is determined using methods described herein, and sequence information is supplied to a commercial vendor for production of a library based on supplied specifications. Commercial vendors are known in the art, e.g., Integrated DNA Technologies (Coralville, Iowa). Alternatively or additionally, the library may be obtained from a mutagenesis method.

In some embodiments, the library is obtained by a random mutagenesis method. In some embodiments, the library is obtained by a comprehensive mutagenesis method, e.g., a method that randomly targets a polynucleotide throughout an entire pre-defined target region for mutagenesis.

In some embodiments, the library is obtained by a targeted mutagenesis method, e.g., by mutagenizing the intended variant portion of the nucleic acid template.

In some embodiments, the library is or is obtained from plasmid library. In some embodiments, plasmids in a library are circular. In some such embodiments, circular plasmids are linearized before use in methods of the present disclosure.

Nucleases

Methods of the present disclosure are suitable for assessing the cleavage profiles of a variety of nucleases, including both well-known nucleases and less characterized nucleases. Generally, the nuclease is site-specific in that it is known or expected to cleave only at a specific sequence or set of sequences, referred to herein as the nuclease's "target site".

In methods presently disclosed herein, incubation step(s) with the nuclease are generally carried under out under conditions favorable for the cleavage by the nuclease. That is, even though a given candidate target site or variant target site might not actually be cleaved by the nuclease, the incubation conditions are such that the nuclease would have cleaved at least a significant portion (e.g., at least 10%, at least 20%, at least 30%, at least 40%, at least 50%, at least 60%, at least 70%, at least 80%, at least 90%, or at least 95%) of templates containing its known target site. For known and generally well-characterized nucleases, such conditions are generally known in the art and/or can easily be discovered or optimized. For newly discovered nucleases, such conditions can generally be approximated using information about related nucleases that are better characterized (e.g., homologs and orthologs).

In some embodiments, the nuclease is an endonuclease. In some embodiments, the nuclease is a site-specific endonuclease (e.g., a restriction endonuclease, a meganuclease, a transcription activator-like effector nucleases (TALEN), a zinc finger nuclease, etc.). In some embodiments, the site specificity of a site-specific nuclease is conferred by an accessory molecule. For example, the CRISPR-associated (Cas) nucleases are guided to specific sites by "guide RNAs" or gRNAs as described herein. In some embodiments, the nuclease is an RNA-guided nuclease. In some embodiments, the nuclease is a CRISPR-associated nuclease.

In some embodiments, the nuclease is a homolog or an ortholog of a previously known nuclease, for example, a newly discovered homolog or ortholog.

RNA-Guided Nucleases

RNA-guided nucleases according to the present disclosure include, but are not limited to, naturally-occurring Class 2 CRISPR nucleases such as Cas9, and Cpf1, as well as other nucleases derived or obtained therefrom. In functional terms, RNA-guided nucleases are defined as those nucleases that: (a) interact with (e.g., complex with) a gRNA; and (b) together with the gRNA, associate with, and optionally cleave or modify, a target region of a DNA that includes (i) a sequence complementary to the targeting domain of the gRNA and, optionally, (ii) an additional sequence referred to as a "protospacer adjacent motif," or "PAM," which is described in greater detail below. As the following examples will illustrate, RNA-guided nucleases can be defined, in broad terms, by their PAM specificity and cleavage activity, even though variations may exist between individual RNA-guided nucleases that share the same PAM specificity or cleavage activity. Skilled artisans will appreciate that some aspects of the present disclosure relate to systems, methods and compositions that can be implemented using any suitable RNA-guided nuclease having a certain PAM specificity and/or cleavage activity. For this reason, unless otherwise specified, the term RNA-guided nuclease should be understood as a generic term, and not limited to any particular type (e.g., Cas9 vs. Cpf1), species (e.g., S. pyogenes vs. S. aureus) or variation (e.g., full-length vs. truncated or split; naturally-occurring PAM specificity vs. engineered PAM specificity, etc.) of RNA-guided nuclease.

The PAM sequence takes its name from its sequential relationship to the "protospacer" sequence that is complementary to gRNA targeting domains (or "spacers"). Together with protospacer sequences, PAM sequences define target regions or sequences for specific RNA-guided nuclease/gRNA combinations.

Various RNA-guided nucleases may require different sequential relationships between PAMs and protospacers. In general, Cas9 s recognize PAM sequences that are 3' of the protospacer as visualized relative to the top or complementary strand:

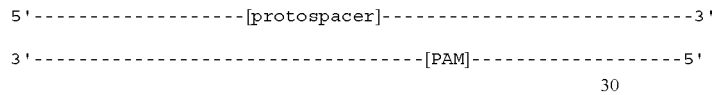

Cpf1, on the other hand, generally recognizes PAM sequences that are 5' of the protospacer:

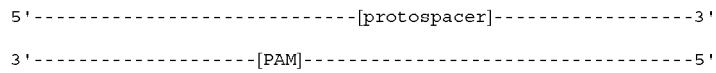

In addition to recognizing specific sequential orientations of PAMs and protospacers, RNA-guided nucleases can also recognize specific PAM sequences. S. aureus Cas9, for instance, recognizes a PAM sequence of NNGRRT or NNGRRV, wherein the N residues are immediately 3' of the region recognized by the gRNA targeting domain. S. pyogenes Cas9 recognizes NGG PAM sequences. And F. novicida Cpf1 recognizes a TTN PAM sequence. PAM sequences have been identified for a variety of RNA-guided nucleases, and a strategy for identifying novel PAM sequences has been described by Shmakov et al., 2015, Molecular Cell 60, 385-397, Nov. 5, 2015. It should also be noted that engineered RNA-guided nucleases can have PAM specificities that differ from the PAM specificities of reference molecules (for instance, in the case of an engineered RNA-guided nuclease, the reference molecule may be the naturally occurring variant from which the RNA-guided nuclease is derived, or the naturally occurring variant having the greatest amino acid sequence homology to the engineered RNA-guided nuclease).

In addition to their PAM specificity, RNA-guided nucleases can be characterized by their DNA cleavage activity: naturally-occurring RNA-guided nucleases typically form DSBs in target nucleic acids, but engineered variants have been produced that generate only SSBs (discussed above) Ran & Hsu, et al., Cell 154(6), 1380-1389, Sep. 12, 2013 ("Ran"), incorporated by reference herein), or that that do not cut at all.

Cas9

Crystal structures have been determined for S. pyogenes Cas9 (Jinek et al., Science 343(6176), 1247997, 2014 ("Jinek 2014"), and for S. aureus Cas9 in complex with a unimolecular guide RNA and a target DNA (Nishimasu 2014; Anders et al., Nature. 2014 Sep. 25; 513(7519):569-73 ("Anders 2014"); and Nishimasu 2015).

A naturally occurring Cas9 protein comprises two lobes: a recognition (REC) lobe and a nuclease (NUC) lobe; each of which comprise particular structural and/or functional domains. The REC lobe comprises an arginine-rich bridge helix (BH) domain, and at least one REC domain (e.g., a REC1 domain and, optionally, a REC2 domain). The REC lobe does not share structural similarity with other known proteins, indicating that it is a unique functional domain. While not wishing to be bound by any theory, mutational analyses suggest specific functional roles for the BH and REC domains: the BH domain appears to play a role in gRNA:DNA recognition, while the REC domain is thought to interact with the repeat:anti-repeat duplex of the gRNA and to mediate the formation of the Cas9/gRNA complex.

The NUC lobe comprises a RuvC domain, an HNH domain, and a PAM-interacting (PI) domain. The RuvC domain shares structural similarity to retroviral integrase superfamily members and cleaves the non-complementary (i.e., bottom) strand of the target nucleic acid. It may be formed from two or more split RuvC motifs (such as RuvC I, RuvCII, and RuvCIII in S. pyogenes and S. aureus). The HNH domain, meanwhile, is structurally similar to HNN endonuclease motifs, and cleaves the complementary (i.e., top) strand of the target nucleic acid. The PI domain, as its name suggests, contributes to PAM specificity.

While certain functions of Cas9 are linked to (but not necessarily fully determined by) the specific domains set forth above, these and other functions may be mediated or influenced by other Cas9 domains, or by multiple domains on either lobe. For instance, in S. pyogenes Cas9, as described in Nishimasu 2014, the repeat:antirepeat duplex of the gRNA falls into a groove between the REC and NUC lobes, and nucleotides in the duplex interact with amino acids in the BH, PI, and REC domains. Some nucleotides in the first stem loop structure also interact with amino acids in multiple domains (PI, BH and REC1), as do some nucleotides in the second and third stem loops (RuvC and PI domains).

Cpf1

The crystal structure of Acidaminococcus sp. Cpf1 in complex with crRNA and a double-stranded (ds) DNA target including a TTTN PAM sequence has been solved by Yamano et al. (Cell. 2016 May 5; 165(4): 949-962 ("Yamano"), incorporated by reference herein). Cpf1, like Cas9, has two lobes: a REC (recognition) lobe, and a NUC (nuclease) lobe. The REC lobe includes REC1 and REC2 domains, which lack similarity to any known protein structures. The NUC lobe, meanwhile, includes three RuvC domains (RuvC-I, -II and -III) and a BH domain. However, in contrast to Cas9, the Cpf1 REC lobe lacks an HNH domain, and includes other domains that also lack similarity to known protein structures: a structurally unique PI domain, three Wedge (WED) domains (WED-I, -II and -III), and a nuclease (Nuc) domain.

While Cas9 and Cpf1 share similarities in structure and function, it should be appreciated that certain Cpf1 activities are mediated by structural domains that are not analogous to any Cas9 domains. For instance, cleavage of the complementary strand of the target DNA appears to be mediated by the Nuc domain, which differs sequentially and spatially from the HNH domain of Cas9. Additionally, the non-targeting portion of Cpf1 gRNA (the handle) adopts a pseudoknot structure, rather than a stem loop structure formed by the repeat:antirepeat duplex in Cas9 gRNAs.

Nucleic Acids Encoding RNA-Guided Nucleases

Nucleic acids encoding RNA-guided nucleases, e.g., Cas9, Cpf1 or functional fragments thereof, are provided herein. Exemplary nucleic acids encoding RNA-guided nucleases have been described previously (see, e.g., Cong et al., Science. 2013 Feb. 15; 339(6121):819-23 ("Cong 2013"); Wang et al., PLoS One. 2013 Dec. 31; 8(12):e85650 ("Wang 2013"); Mali 2013; Jinek 2012).

In some cases, a nucleic acid encoding an RNA-guided nuclease can be a synthetic nucleic acid sequence. For example, the synthetic nucleic acid molecule can be chemically modified. In certain embodiments, an mRNA encoding an RNA-guided nuclease will have one or more (e.g., all) of the following properties: it can be capped; polyadenylated; and substituted with 5-methylcytidine and/or pseudouridine.

Synthetic nucleic acid sequences can also be codon optimized, e.g., at least one non-common codon or less-common codon has been replaced by a common codon. For example, the synthetic nucleic acid can direct the synthesis of an optimized messenger mRNA, e.g., optimized for expression in a mammalian expression system, e.g., described herein. Examples of codon optimized Cas9 coding sequences are presented in WO 2016/073990 ("Cotta-Ramusino").

In addition, or alternatively, a nucleic acid encoding an RNA-guided nuclease may comprise a nuclear localization sequence (NLS). Nuclear localization sequences are known in the art.

Guide RNA (gRNA) Molecules

The terms "guide RNA" and "gRNA" refer to any nucleic acid that promotes the specific association (or "targeting") of an RNA-guided nuclease such as a Cas9 or a Cpf1 to a target sequence such as a genomic or episomal sequence in a cell. gRNAs can be unimolecular (comprising a single RNA molecule, and referred to alternatively as chimeric), or modular (comprising more than one, and typically two, separate RNA molecules, such as a crRNA and a tracrRNA, which are usually associated with one another, for instance by duplexing). gRNAs and their component parts are described throughout the literature, for instance in Briner et al. (Molecular Cell 56(2), 333-339, Oct. 23, 2014 ("Briner"), which is incorporated by reference), and in Cotta-Ramusino.

In bacteria and archea, type II CRISPR systems generally comprise an RNA-guided nuclease protein such as Cas9, a CRISPR RNA (crRNA) that includes a 5' region that is complementary to a foreign sequence, and a trans-activating crRNA (tracrRNA) that includes a 5' region that is complementary to, and forms a duplex with, a 3' region of the crRNA. While not intending to be bound by any theory, it is thought that this duplex facilitates the formation of—and is necessary for the activity of—the Cas9/gRNA complex. As type II CRISPR systems were adapted for use in gene editing, it was discovered that the crRNA and tracrRNA could be joined into a single unimolecular or chimeric guide RNA, in one non-limiting example, by means of a four nucleotide (e.g., GAAA) "tetraloop" or "linker" sequence bridging complementary regions of the crRNA (at its 3' end) and the tracrRNA (at its 5' end). (Mali et al. Science. 2013 Feb. 15; 339(6121): 823-826 ("Mali 2013"); Jiang et al. Nat Biotechnol. 2013 March; 31(3): 233-239 ("Jiang"); and Jinek et al., 2012 Science August 17; 337(6096): 816-821 ("Jinek 2012"), all of which are incorporated by reference herein.)

Guide RNAs, whether unimolecular or modular, include a "targeting domain" that is fully or partially complementary to a target domain within a target sequence, such as a DNA sequence in the genome of a cell where editing is desired. Targeting domains are referred to by various names in the literature, including without limitation "guide sequences" (Hsu et al., Nat Biotechnol. 2013 September; 31(9): 827-832, ("Hsu"), incorporated by reference herein), "complementarity regions" (Cotta-Ramusino), "spacers" (Briner) and generically as "crRNAs" (Jiang). Irrespective of the names they are given, targeting domains are typically 10-30 nucleotides in length, and in certain embodiments are 16-24 nucleotides in length (for instance, 16, 17, 18, 19, 20, 21, 22, 23 or 24 nucleotides in length), and are at or near the 5' terminus of in the case of a Cas9 gRNA, and at or near the 3' terminus in the case of a Cpf1 gRNA.

In addition to the targeting domains, gRNAs typically (but not necessarily, as discussed below) include a plurality of domains that may influence the formation or activity of gRNA/Cas9 complexes. For instance, as mentioned above, the duplexed structure formed by first and secondary complementarity domains of a gRNA (also referred to as a repeat:anti-repeat duplex) interacts with the recognition (REC) lobe of Cas9 and can mediate the formation of Cas9/gRNA complexes. (Nishimasu et al., Cell 156, 935-949, Feb. 27, 2014 ("Nishimasu 2014") and Nishimasu et al., Cell 162, 1113-1126, Aug. 27, 2015 ("Nishimasu 2015"), both incorporated by reference herein). It should be noted that the first and/or second complementarity domains may contain one or more poly-A tracts, which can be recognized by RNA polymerases as a termination signal. The sequence of the first and second complementarity domains are, therefore, optionally modified to eliminate these tracts and promote the complete in vitro transcription of gRNAs, for instance through the use of A-G swaps as described in Briner, or A-U swaps. These and other similar modifications to the first and second complementarity domains are within the scope of the present disclosure.

Along with the first and second complementarity domains, Cas9 gRNAs typically include two or more additional duplexed regions that are involved in nuclease activity in vivo but not necessarily in vitro. (Nishimasu 2015). A first stem-loop one near the 3' portion of the second complementarity domain is referred to variously as the "proximal domain," (Cotta-Ramusino) "stem loop 1" (Nishimasu 2014 and 2015) and the "nexus" (Briner). One or more additional stem loop structures are generally present near the 3' end of the gRNA, with the number varying by species: S. pyogenes gRNAs typically include two 3' stem loops (for a total of four stem loop structures including the repeat:anti-repeat duplex), while S. aureus and other species have only one (for a total of three stem loop structures). A description of conserved stem loop structures (and gRNA structures more generally) organized by species is provided in Briner.

While the foregoing description has focused on gRNAs for use with Cas9, it should be appreciated that other RNA-guided nucleases have been (or may in the future be) discovered or invented which utilize gRNAs that differ in some ways from those described to this point. For instance, Cpf1 ("CRISPR from Prevotella and Franciscella 1") is a recently discovered RNA-guided nuclease that does not require a tracrRNA to function. (Zetsche et al., 2015, Cell 163, 759-771 Oct. 22, 2015 ("Zetsche I"), incorporated by reference herein). A gRNA for use in a Cpf1 genome editing system generally includes a targeting domain and a complementarity domain (alternately referred to as a "handle"). It should also be noted that, in gRNAs for use with Cpf1, the targeting domain is usually present at or near the 3' end, rather than the 5' end as described above in connection with Cas9 gRNAs (the handle is at or near the 5' end of a Cpf1 gRNA).

Those of skill in the art will appreciate, however, that although structural differences may exist between gRNAs from different prokaryotic species, or between Cpf1 and Cas9 gRNAs, the principles by which gRNAs operate are generally consistent. Because of this consistency of operation, gRNAs can be defined, in broad terms, by their targeting domain sequences, and skilled artisans will appreciate that a given targeting domain sequence can be incorporated in any suitable gRNA, including a unimolecular or chimeric gRNA, or a gRNA that includes one or more chemical modifications and/or sequential modifications (substitutions, additional nucleotides, truncations, etc.). Thus, for economy of presentation in this disclosure, gRNAs may be described solely in terms of their targeting domain sequences.

More generally, skilled artisans will appreciate that some aspects of the present disclosure relate to systems, methods and compositions that can be implemented using multiple RNA-guided nucleases. For this reason, unless otherwise specified, the term gRNA should be understood to encompass any suitable gRNA that can be used with any RNA-guided nuclease, and not only those gRNAs that are compatible with a particular species of Cas9 or Cpf1. By way of illustration, the term gRNA can, in certain embodiments, include a gRNA for use with any RNA-guided nuclease occurring in a Class 2 CRISPR system, such as a type II or type V or CRISPR system, or an RNA-guided nuclease derived or adapted therefrom.

Control Nucleases

The control nuclease can be any of a variety of known nucleases. Generally, the control nuclease is a site-specific nuclease whose target site is known.

In methods presently disclosed herein, incubation step(s) with the control nuclease are generally carried under out under conditions that allow the control nuclease to cleave at its target site. Incubation conditions are generally such that the control nuclease will cleave at least a significant portion (e.g., at least 10%, at least 20%, at least 30%, at least 40%, at least 50%, at least 60%, at least 70%, at least 80%, at least 90%, or at least 95%) of templates containing its target site. Such conditions are generally known in the art, and, for commercially available nucleases, are typically included with the manufacturers' instructions.

In some embodiments, the control nuclease is a restriction enzyme. In such embodiments, the control target site is the restriction site for the restriction enzyme.

In some embodiments, cleavage by the control nuclease generates a blunt end. In some such embodiments, the blunt end comprises a 5' phosphate.

Non-limiting examples of restriction enzymes that cleave to generate a blunt end include AfeI, AluI, BasAI, BstUI, BstZ17I, DraI, EcoRV, FspI, HaeIII/PhoI, HpaI, HincII, MscI, MspA1I, NaeI, NruI, PmeI, PmlI, PvuII, RsaI, ScaI, SfoI, SmaI, SnaBI, SspI, StuI, and SwaI.

In some embodiments, cleavage by the control nuclease generates an overhang, for example, a 5' or 3' overhang.

Ligating

Some embodiments of presently disclosed methods comprise a step of ligating nucleic acid sequences, e.g., cleaved ends of a nucleic acid template with an oligonucleotide capture probe or a mixture thereof. In some embodiments, the step of ligating is accomplished using a ligase enzyme that acts on nucleic acids, e.g., a DNA and/or RNA ligase. A variety of such ligases are known in the art, many of which are commercially available.

Examples of ligases that may be used in various embodiments of the presently disclosed methods include, but are not limited to, T4 DNA ligase, T3 DNA ligase, T7 DNA ligase, and $E.$ $coli$ ligase.

The type of ligase chosen may depend on the type of cleaved ends present in the cleavage composition and/or the capture end of oligonucleotide capture probe.

For example, if the cleaved ends in the cleavage composition comprise blunt ends, or comprise cleaved ends that are blunted before ligation (e.g., during an additional step of blunting, as described herein), a ligase suitable for ligating blunt ends may be chosen.

For example, if the cleaved ends in the cleavage composition comprise overhangs ("sticky ends") that will not be blunted before ligation (e.g., during an additional step of blunting, as described herein), a ligase suitable for ligating sticky ends may be chosen.

Some ligases work well for both blunt ends and ends with overhangs, and any of these ligases may be used in methods of the present disclosure.

Furthermore, any combination of two or more ligases may also be used during a ligating step.

Analysis of Ligation Products

In some embodiments, a plurality of ligation products (e.g., the first and/or second plurality of ligation products) is analyzed. In some embodiments, the plurality of ligation products is amplified. In some embodiments in which the plurality of ligation products comprises one or more detection sequences, amplification primers that recognize one or more of the detection sequences are used.

In some such embodiments, amplification products are analyzed.

For example, in some embodiments, methods further comprise a step of determining the levels of the first and second pluralities of ligation products. The levels that are determined can be absolute and/or relative.

In some embodiments, methods further comprise a step of calculating a relative abundance of the first and second pluralities of ligation products. For example, an approximate percentage of cleaved or uncleaved templates can be calculated, and/or an approximate ratio of cleaved to uncleaved templates can be calculated.

The analysis may comprise nucleic acid sequencing of the ligation product and/or amplification product thereof. As a non-limiting example, next generation (also known as high throughput sequencing) can be performed.

In some embodiments, deep sequencing is performed, meaning that each nucleotide is read several times during the sequencing process, for example at a depth of greater than at least 7, at least 10, at least 15, at least 20, or ever greater, wherein depth (D) is calculated as $$D = N \times L / G \qquad \text{(Equation 1)},$$

wherein N is the number of reads, L is the length of the original genome, and G is length of the polynucleotide being sequenced.

In some embodiments, Sanger sequencing is used to analyze at least some of the ligation products and/or amplification products thereof.

Modeling Systems

The disclosure also provides methods of producing model networks, e.g., neural network models, using information obtained from analysis of cleavage of a library of candidate target sites for a given guide RNA. For example, a library described herein can include variant nucleic acid templates that each comprises a control target site for a control nuclease and a variant target site for the guide RNA, and such library can be used in a method of the disclosure to determine relative abundance of a first ligation product and/or a second ligation product described herein, to obtain an assessment of off-target cleavage by such guide RNA.

Figure 14:
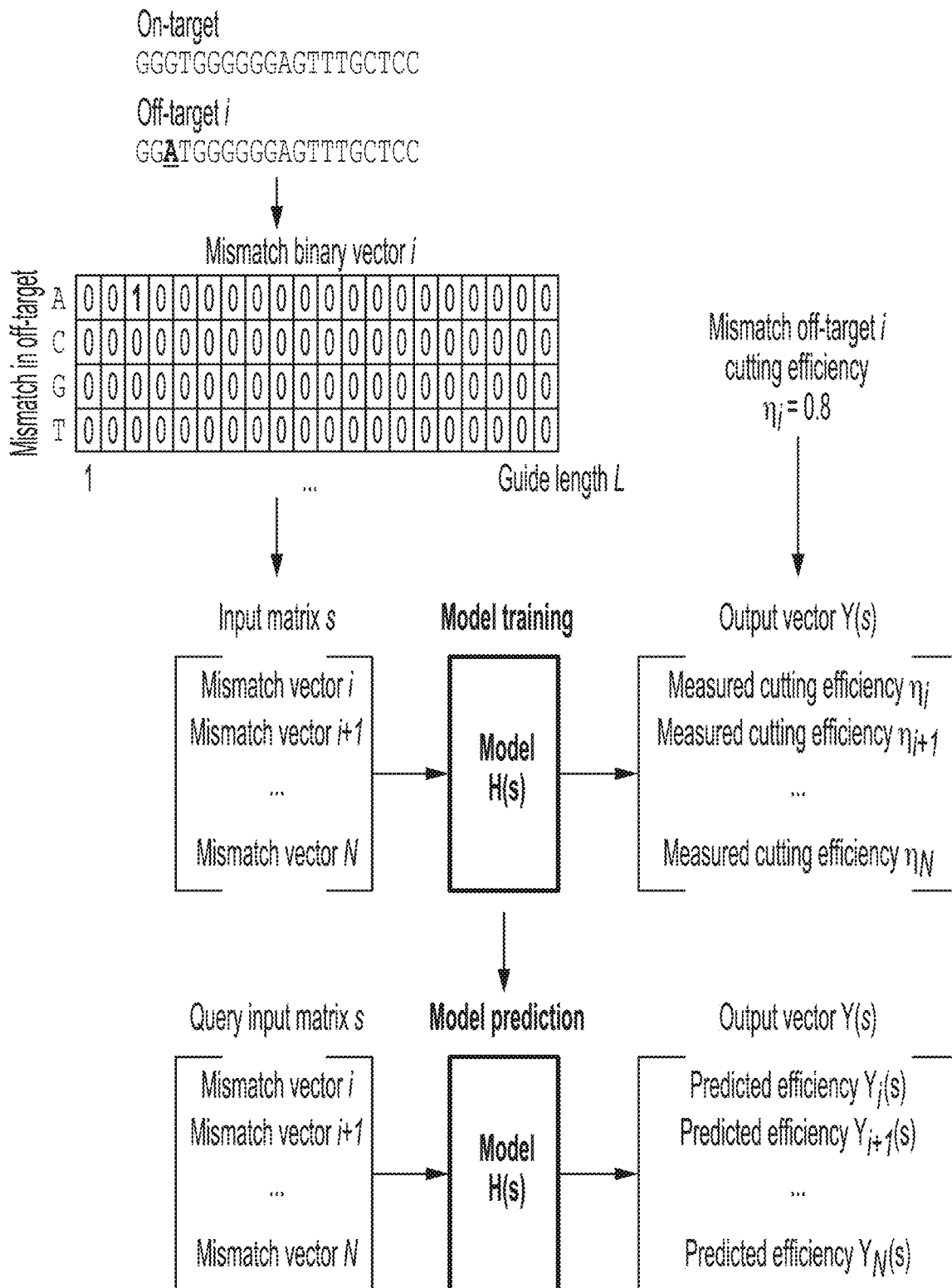
FIG. 14 depicts a schematic of an exemplary neural network modeling process (SEQ ID NOS 36-37, respectively, in order of appearance).

An exemplary method is depicted in FIG. 14. Mismatches of the target to the guide can be reformatted as a 4 by L (guide length) matrix with 1's representing mismatches to A, C, G, or T (in rows 1-4 respectively) and 0's representing matched bases. A matrix can then be created consisting of each mismatch string in the obtained cleavage data (e.g., from a BLT assessment). This matrix can be input into a suitable algorithm, such as Matlab Neural Network toolbox, with a vector of associated cutting efficiencies Ili as expected output.

At least some of the processes described herein to predict guide-specific cleavage specificity including, but not limited to, neural network modeling, may be implemented using one or more computer systems comprising hardware or a combination of hardware and software. For example, computer systems may include various controllers and/or processing devices located at various points to control operation of automated elements. A central computer may coordinate operation among the various controllers or processing devices. The central computer, controllers, and processing devices may execute various software routines to implement control and coordination of the various automated elements.

The example process can be implemented, at least in part, using one or more computer program products, e.g., one or more computer program tangibly embodied in one or more information carriers, such as one or more non-transitory machine-readable media, for execution by, or to control the operation of, one or more data processing apparatus, e.g., a programmable processor, a computer, multiple computers, and/or programmable logic components.

A computer program can be written in any form of programming language, including compiled or interpreted languages, and it can be deployed in any form, including as a stand-alone program or as a module, component, subroutine, or other unit suitable for use in a computing environment. A computer program can be deployed to be executed on one computer or on multiple computers at one site or distributed across multiple sites and interconnected by a network.

Actions associated with implementing all or part of the example process can be performed by one or more programmable processors executing one or more computer programs to perform the functions described herein. All or part of the example process can be implemented using special purpose logic circuitry, e.g., an FPGA (field programmable gate array) and/or an ASIC (application-specific integrated circuit).

Processors suitable for the execution of a computer program include, by way of example, both general and special purpose microprocessors, and any one or more processors of any kind of digital computer. Generally, a processor will receive instructions and data from a read-only storage area or a random access storage area or both. Elements of a computer (including a server) include one or more processors for executing instructions and one or more storage area devices for storing instructions and data. Generally, a computer will also include, or be operatively coupled to receive data from, or transfer data to, or both, one or more machine-readable storage media, such as mass storage devices for storing data, e.g., magnetic, magneto-optical disks, or optical disks. Machine-readable storage media suitable for embodying computer program instructions and data include all forms of non-volatile storage area, including by way of example, semiconductor storage area devices, e.g., EPROM, EEPROM, and flash storage area devices; magnetic disks, e.g., internal hard disks or removable disks; magneto-optical disks; and CD-ROM and DVD-ROM disks.

All publications, patent applications, patents, and other references mentioned herein are incorporated by reference in their entirety. In addition, the materials, methods, and examples are illustrative only and not intended to be limiting. Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described herein.

The disclosure is further illustrated by the following examples. The examples are provided for illustrative purposes only. They are not to be construed as limiting the scope or content of the disclosure in any way.

EXAMPLES

Example 1

Assessment of Guide-Intrinsic Determinants of Cas9 Specificity

The present Example describes generation and analysis of barcoded library of DNA templates ("BLT") containing candidate target sites for Cas9.

Methods

Library Synthesis: ssDNA template was ordered through Integrated DNA Technologies (IDT), with 10% programmed degeneracy at each base of the wildtype (WT) target. At any given base position within a synthesized template library, 90% of template target contained the WT base, with the remaining 10% of templates containing any of the other three bases. Constant sequences 5' of the target included an EcoRV cut site and a priming site for template library preparation. Constant sequences 3' of the target included a PAM, a randomized UMI for target identification (LIMIT), and a P7 priming site. (Table 1)

TABLE 1

| Template Sequences | Sequence |
| --- | --- |
| Upstream (Primer$_T$, EcoRV) | GCCTGGACTCAA*CCGGACC CGGG*GATATC*TG* (SEQ ID NO: 1) |
| Target Site (23-mer + endogenous PAM) | Guide specific |

TABLE 1-continued

| Template Sequences | Sequence |
|---|---|
| Downstream (UMI$_T$, P7-Adaptor) | GC*NNNNNNNNNNNN*<br>TGACAGATCGGAAGAGC<br>ACACGTCTGAACTCCAG<br>TCACGCTGCTATCTCGT<br>ATGCCGTCTTCTGCTTG<br>(SEQ ID NO: 2) |

Library bottlenecking: Template libraries obtained from IDT were brought to 100 µM in low-TE (10 mM Tris-HCL, 0.1 mM EDTA, pH 8.0) and then serially diluted 1000-fold in 10× increments. Concentrations of each dilution were determined with a Qubit ssDNA Assay Kit (Qubit Q10212) and diluted to 250,000 copies/µL. Libraries were PCR-amplified with approximately 62,500 template copies per reaction across 8 technical replicates, or 500,000 templates total. All PCR reactions were prepared with 25 µL 2×NEB-Next Ultra II DNA Library Prep Kit (NEB: E7645S), and 0.5 µM of P7-Adaptor and Primer$_T$ primers. Reactions were run at 95° C. for 1 min, 27 cycles of 94° C. for 30 s, 60° C. for 30 s, and 72° C. for 30 s, with a final extension at 72° C. for 7 min. PCR product was concentrated with Zymo DNA Clean & Concentrator kit (Zymo: D4004) to facilitate downstream reaction preparation.

RNP Preparation: Component parts for two-part synthetics, including both the crRNA and tracrRNA, were obtained as RNA from IDT (Table 2).

TABLE 2

| Two-Part synthetic guides | Sequence |
|---|---|
| Direct Repeat | RNA Spacer +<br>GUUUUAGUACUCUGUAAUUUU<br>(SEQ ID NO: 3) |
| Scaffold | AAAAUUACAGAAUCUACUAAA<br>ACAAGGCAAAAUGCCGUGUUU<br>AUCUCGUCAACUUGUUGGCGA<br>GAUUUU (SEQ ID NO: 4) |

Guide-RNA annealing reactions were prepared with 7.5 µL of both 100 µM crRNA and 100 µM tracrRNA, 3 µL 10× Annealing Buffer (100 mM Tris-HCL, 500 mM NaCl, 10 mM EDTA), and 12 µL nuclease-free (NF) water. Reactions were annealed at 90° C. for 5 min and a 2% ramp to 25° C. Final complexed guide-RNA concentration was 25 µM. *S. aureus* Cas9 was obtained from Aldevron with a 6×C-terminal His-tag (SEQ ID NO: 38) and at a stock concentration of 50 µM. Protein was stored at −80° C. until used.

All RNP was complexed using freshly prepared two-part synthetics. Complexation reactions were prepared with 4 µL *S. aureus* Cas9, 2 µL 10×H300 buffer (100 mM Hepes, 3M NaCl, pH 7.5), 8.8 µL two-part synthetics, and 5.2 µL NF water. Reaction components were combined in the order listed. The complexation reaction was left to incubate at room temperate for 15 min, then immediately used in cutting assays. Final RNP concentration was 10 µM.

Cutting Reactions: Desired ratios of *S. aureus* Cas9 RNP:dsDNA template dictated reaction set-up and was context dependent, ranging from 1:1 to 10:1. All cutting reactions were prepared to a final volume of 10 µL, with constant addition of 1 µL 10×H300 and 2 µL 10 mM MgCl$_2$. A cutting reaction typically contained final concentrations of 2.5 nM *S. aureus* Cas9 RNP and 0.5 nM dsDNA template for a final RNP:template of 5:1. Cutting reactions run in the presence of human gDNA contained gDNA at a final concentration of 750 ng/µL. Reactions were run at 37° C. for either 30 min or 16 hr.

Samples were moved into the EcoRV digest immediately following completion of Cas9 cutting reaction. To the 10 µL reaction was added 10 µL 10×CutSmart (NEB), 5 µL EcoRV-HF (NEB), and 75 µL NF water. EcoRV digest proceeded at 37° C. for 30 min. Digested product was concentrated with Zymo DNA Clean & Concentrator kit (Zymo: D4004) and eluted in 10 µL.

Probe Preparation and Ligation: Probes were obtained as ssDNA molecules from IDT (Table 3). Constant sequences included a 5' P5 Illumina adaptor, a nucleotide stagger ranging from 1-8 bp, two discrete 6 bp anchoring sequences, a fully randomized barcode for multiplexed sequencing reactions, a probe UMI (UMI$_P$) to control for PCR bias and identify unique ligation events, and a constant 3' anchoring sequence to facilitate probe amplification.

TABLE 3

| Probe No. | Start (P5-Adaptor) | Stagger | Anchor 1 | Barcode | Anchor 2 | UMI$_P$ | End (Primer$_P$) | SEQ ID NO: |
|---|---|---|---|---|---|---|---|---|
| 1 | AATGATACGGCGAC<br>CACCGAGATCTACA<br>CTCTTTCCCTACAC<br>GACGCTCTTCCGAT<br>CT | GCGG<br>AAGC | CGATCT | CACATAC<br>GCACTAC<br>G | TACG<br>AC | NNN<br>NNN | TTACCGAAGATA<br>GCAGCCTAGTGG<br>AACC | 5 |
| 2 | AATGATACGGCGAC<br>CACCGAGATCTACA<br>CTCTTTCCCTACAC<br>GACGCTCTTCCGAT<br>CT | GCGG<br>AAG | CGATCT | CCTATAC<br>CCGAATC<br>T | TACG<br>AC | NNN<br>NNN | TTACCGAAGATA<br>GCAGCCTAGTGG<br>AACC | 6 |
| 3 | AATGATACGGCGAC<br>CACCGAGATCTACA<br>CTCTTTCCCTACAC<br>GACGCTCTTCCGAT<br>CT | GCGG<br>AA | CGATCT | TATACAA<br>TTCGCAG<br>C | TACG<br>AC | NNN<br>NNN | TTACCGAAGATA<br>GCAGCCTAGTGG<br>AACC | 7 |

TABLE 3-continued

| Probe No. | Start (P5-Adaptor) | Stagger | Anchor 1 | Barcode | Anchor 2 | UMI$_P$ | End (Primer$_P$) | SEQ ID NO: |
|---|---|---|---|---|---|---|---|---|
| 4 | AATGATACGGCGAC CACCGAGATCTACA CTCTTTCCCTACAC GACGCTCTTCCGAT CT | GCGG A | CGATCT | CCGGAGT AGGTCCT C | TACG AC | NNN NNN | TTACCGAAGATA GCAGCCTAGTGG AACC | 8 |
| 5 | AATGATACGGCGAC CACCGAGATCTACA CTCTTTCCCTACAC GACGCTCTTCCGAT CT | GCGG | CGATCT | ATTGCAA GGGCCCT T | TACG AC | NNN NNN | TTACCGAAGATA GCAGCCTAGTGG AACC | 9 |
| 6 | AATGATACGGCGAC CACCGAGATCTACA CTCTTTCCCTACAC GACGCTCTTCCGAT CT | GCG | CGATCT | TCCCGTC GTCCACA A | TACG AC | NNN NNN | TTACCGAAGATA GCAGCCTAGTGG AACC | 10 |
| 7 | AATGATACGGCGAC CACCGAGATCTACA CTCTTTCCCTACAC GACGCTCTTCCGAT CT | GC | CGATCT | TGCGTGA CAAGCTC T | TACG AC | NNN NNN | TTACCGAAGATA GCAGCCTAGTGG AACC | 11 |
| 8 | AATGATACGGCGAC CACCGAGATCTACA CTCTTTCCCTACAC GACGCTCTTCCGAT CT | G | CGATCT | GCGCAGT CTTTCTG C | TACG AC | NNN NNN | TTACCGAAGATA GCAGCCTAGTGG AACC | 12 |

Probes were PCR amplified prior to use. All PCR reactions were prepared with 25 µL 2×NEBNext Ultra II DNA Library Prep Kit (NEB: E7645S), 0.5 µM of both P5-Adaptor and PrimerP primers, and 0.18 µL 100 µM probe. Reactions were run at 95° C. for 1 min, 20 cycles of 94° C. for 30 s, 60° C. for 30 s, and 72° C. for 30 s, with a final extension at 72° C. for 7 min. PCR product was concentrated with Zymo DNA Clean & Concentrator kit (Zymo: D4004) and normalized to 30 ng/µL.

All ligation reactions were prepared using 5 µL of digested template library, 3 µL of 30 ng/µL probe, 1 µL 10×T4 Ligase buffer, and 1 µL high concentration T4 Ligase (NEB: M0202M). Ligation reactions proceeded at room temperature for 1 hr.

Library Sequencing Preparation and Q.C.: Following probe ligation, template libraries were PCR amplified for sequencing on the Illumina Miseq platform. All library amplification reactions were prepared using 25 µL 2×NEBNext Ultra II DNA Library Prep Kit (NEB: E76455), 0.5 µM of both P5-Adaptor and P7-Adaptor primers, and 2 µL of ligated DNA template. All PCR reactions were prepared in triplicate and pooled post-PCR for increased yield. Reactions were run at 95° C. for 1 min, 14 cycles of 94° C. for 30 s, 60° C. for 30 s, and 72° C. for 30 s, with a final extension at 72° C. for 7 min. Pooled samples were run on 1% E-Gel Pre-Cast Agarose gels (Invitrogen). To ensure equivalent read distribution between samples, relative band intensities were used to determine library pooling.

Once pooled, the library was run on a 1% E-Gel Pre-Cast Agarose gels (Invitrogen). The region between 200-350 bp was excised. DNA was recovered using the Zymoclean™ Gel DNA Recovery Kit (Zymo Research: D4001T) and eluted in 20 µL. Concentration of the final library was determined using Qubit™ dsDNA HS assay kit (Invitrogen: Q32851).

For Miseq loading, a 10 pM library dilution was prepared, including the addition of 10% PhiX library spike-in to maintain cluster diversity. Miseq Reagent Kit v2 was used for data collection, with 150 bp single reads used for data analysis.

Data Analysis: Fastq files were parsed and demutiplexed according to probe barcode. Constant template and probe sequences, including probe UMI$_P$, PAM, and template UMI$_T$, were extracted. Mean read quality across these sequences, instead of the entire read, was determined. Any read with a mean read quality below Q20 was discarded.

After filtering on quality, reads were collapsed into 'observations,' or any read that shares the same UMI$_T$, UMI$_P$, cut/uncut status, and probe stagger length. Targets were filtered by requiring at least three unique observations of a given uncut template-UMI$_T$ combination, as UMI$_T$ was used to identify target sequences cleaved by Cas9. To avoid biasing against targets with high cleavage efficiency, naïve libraries were spiked-in to aid in target validation. Remaining observations were then grouped across samples by guide, PAM, and UMI$_T$, and were used to calculate cut fraction.

Individual template biochemical testing: Cleavage efficiency was measured by a dose-response of RNP against 2 nM DNA substrate for 1 hour at 37° C. RNP was added and mixed with DNA substrate using a Biomek FX$^p$ liquid handler. Activity was quenched by addition of Proteinase K followed by RNase If (NEB). Fraction of cleaved substrate was measured using the Fragment Analyzer automated CE system (AATI). Analysis was performed with GraphPad Prism using four parameter dose-response.

Guide-specific neural network modeling: Mismatches of the target to the guide were reformatted as a 4 by 21 matrix with 1's representing mismatches to A, C, G, or T (in rows 1-4 respectively) and 0's representing matched bases (as shown in FIG. 14). This matrix was reformatted again to a single binary string (1 by 84). A matrix was then created consisting of each mismatch string in the BLT data. This matrix was inputted into the Matlab Neural Network toolbox with a vector of associated cutting efficiencies $\eta_i$ as expected output. 10 neurons were used with the Lavenberg-Marquardt training algorithm. Models were trained on 70% of inputted data, with 15% reserved for validation and 15% reserved as untrained data. All possible genomic off-targets of up to 6 mismatches to a given target were input as binary strings and processed through the generated neural network model to create the distribution shown in FIG. 7B.

Ni-Bead Extraction: A Ni-NTA Magnetic Agarose Bead extraction kit (Qiagen) was used to analyze the template content and cut status of Cas9-bound dsDNA. Cas9 cutting reactions were prepared with 33 nM dsDNA template and 330 nM S. aureus Cas9 RNP (10:1 RNP:dsDNA template). Cutting reactions were run for 30 min at 37° C.

Immediately following completion of the S. aureus Cas9 cutting reaction, 1 µL 0.5% Tween20 (Sigma Aldritch) was added to prevent precipitation of the reaction's high protein content upon bead addition. 10 µL of Ni-NTA magnetic bead suspension was then added to the reaction. The reaction was mixed by pipette and incubated at room temperature for 1 hr to allow sufficient time for protein-bead binding. The sample was placed on a magnetic rack for 1 min followed by aspiration of supernatant. Two 30 s washes with 1×H300 (10 mM Hepes, 300 mM NaCl, pH 7.5) were performed while on the magnetic rack. After removal from the magnetic rack, the pellet was resuspended in 30 µM NaCl and eluted at room temperature for 5 min. Following elution, the sample was separated for 1 min on the magnetic rack. Supernatant was collected, concentrated with Zymo DNA Clean & Concentrator kit (Zymo: D4004), and eluted in 10 µL NF water. Samples were immediately carried into EcoRV digest steps described above.

The following spacers and target sites were used:

| Guide | RNA Spacer | SEQ ID NO: | Target Site (23-mer) | PAM | SEQ ID NO: |
|---|---|---|---|---|---|
| Guide 1 | GGCCUCCCCAA AGCCUGGCCA | 13 | CAGGCCTCCCCA AAGCCTGGCCA | GGG AGT | 19 |
| Guide 2 | GGGUGAGUGAG UGUGUGCGUG | 14 | CCTGGCCAGGCT TTGGGGAGGCC | GGG AGT | 20 |
| Guide 3 | GAAUAGUUUGU UCUGGGUAC | 15 | GGAGAATAGTTT GTTCTGGGTAC | AGG GGT | 21 |
| Guide 4 | GAGAAAGGGAU GGGCACUUA | 16 | TAAGAGAAAGGG ATGGGCACTTA | ATG AGT | 22 |
| Guide 5 | GAUGCAGAACU AGUGUAGAC | 17 | TAAGATGCAGAA CTAGTGTAGAC | AGG AGT | 23 |
| Guide 6 | GAGUAUCUCCU GUUUGGCA | 18 | TGTTGAGTATCT CCTGTTTGGCA | CAG AGT | 24 |

Results

Figure 1B:
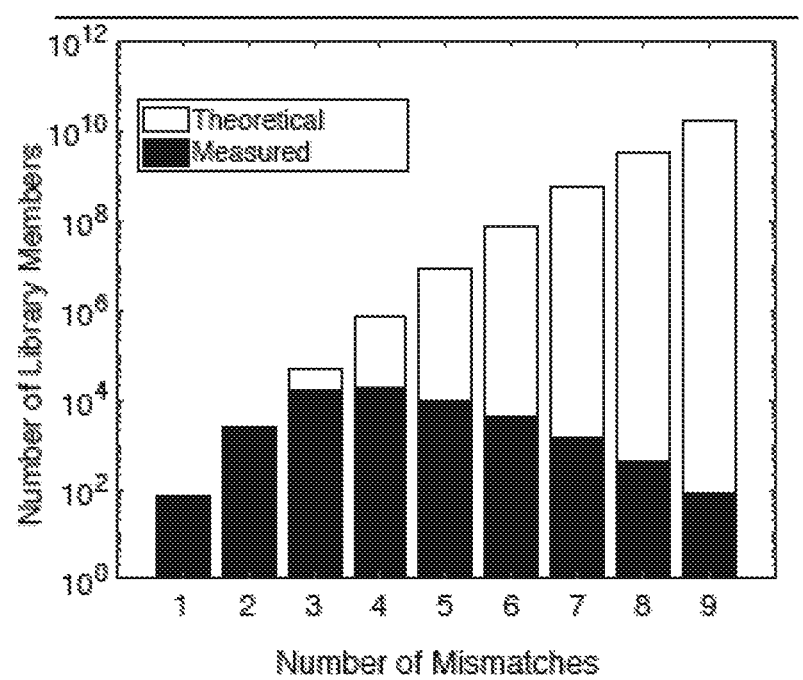
FIG. 1B depicts a graph showing theoretical and measured numbers of mismatches (x-axis) relative to library size (number of members, y-axis).

Barcoded Libraries of Targets Assessed Cleavage Efficiencies at a Wide Range of Mismatches To evaluate large numbers of off-targets to a guide in vitro, a screening strategy was created using a barcoded library of targets (FIG. 1A). For each gRNA of interest, a template synthetic dsDNA library was generated with a constant PAM and a degenerate target site for that gRNA with a 10% chance of random mismatch incorporation at each position relative to a given Cas9 guide (providing 3 median mutations per target, FIG. 1B). In order to quantitate uncleaved library members, an EcoRV site was included within the construct. After digestion with Cas9 ribonucleoprotein (RNP), the remaining uncut library members were cleaved with EcoRV. Cleavage events exposed a 5' phosphate, enabling ligation of molecules to a dsDNA for subsequent PCR amplification and sequencing. These ligated products were then amplified by PCR to create a sequencing library. The library was split between long (243 bp) reads and short (218 bp) reads corresponding to ligation events at the EcoRV site or the Cas9 site, respectively.

Counting the long and short reads provided a measure of the Cas9-cut fraction associated with a certain target sequence (Equation 2).

Equation 2. For a given target i:

$$\eta_i = \left(\frac{\sum Cleaved_i}{\sum Observations_i}\right)\left(\frac{\sum Observations_{on\text{-}target}}{\sum Cleaved_{on\text{-}target}}\right)$$

where $\eta$ represents normalized cutting efficiency to the on-target cleavage rate.

Figure 1C:
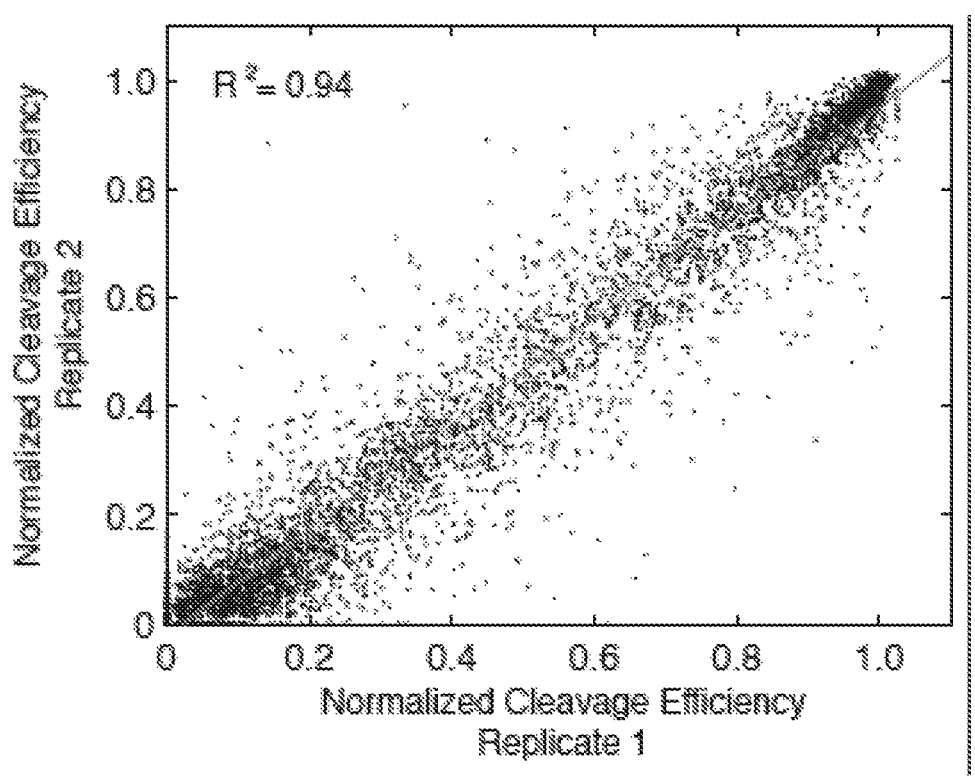
FIG. 1C depicts a plot comparing cutting efficiency across experiments.

The measure of cutting efficiency was highly reproducible across experiments (FIG. 1C), with $R^2=0.94$ in the overall data set and reaching $R^2=0.98$ by filtering by at least 50 reads analyzed per target.

Figure 2A:
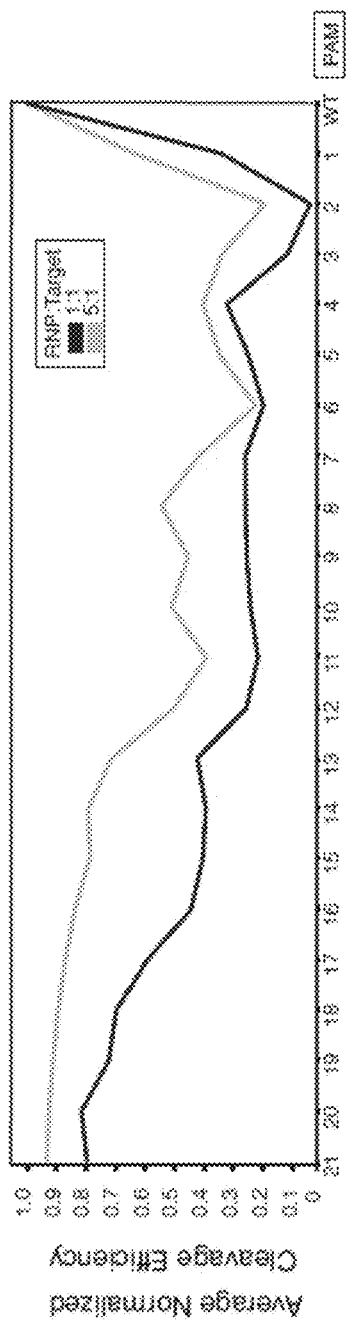
FIG. 2A depicts a plot showing normalized cleavage efficiency (y-axis; expressed as a number with 1.0 representing wild type) as a function of single mismatches by position (number of nucleotides away) from a PAM (x-axis) at two different ratios of RNP:target.
Figure 2B:
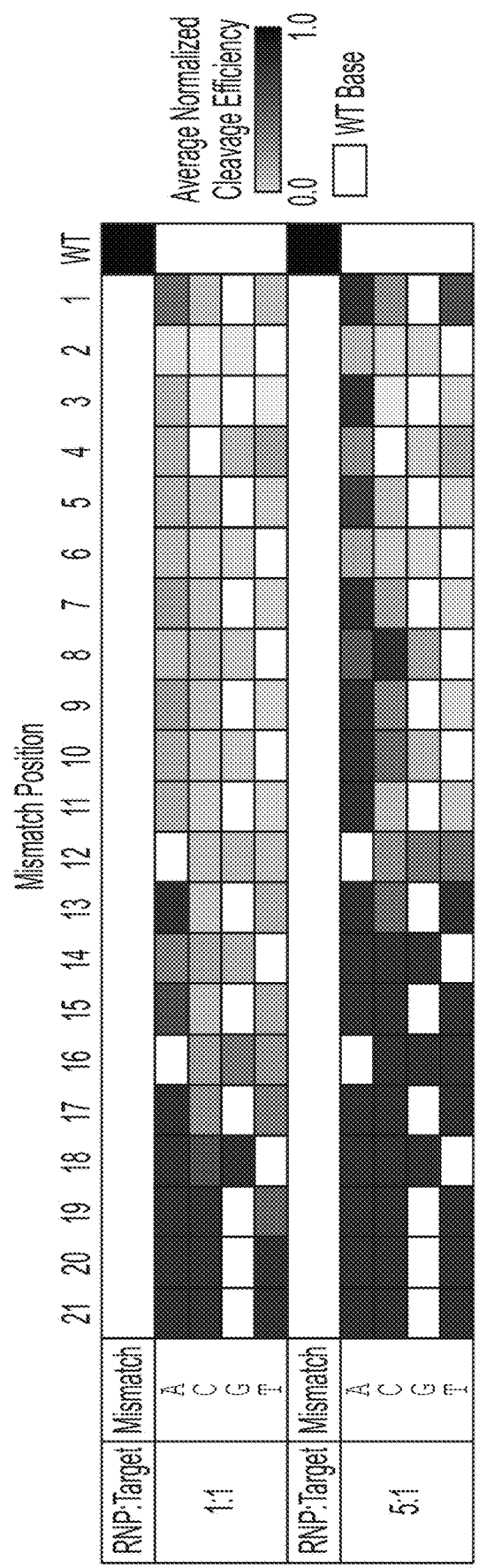
FIG. 2B depicts a plot showing quantitation at two different ratios of RNP:target of single mismatches by position (number of nucleotides away) from a PAM and by nucleotide (A, G, T, C) indicating normalized cleavage efficiency in each box (where a white box represents a wild-type nucleotide and cleavage efficiency of other nucleotides at the same position is represented by a normalized gradient where black represents 1.0).
Figures 1, 2C:
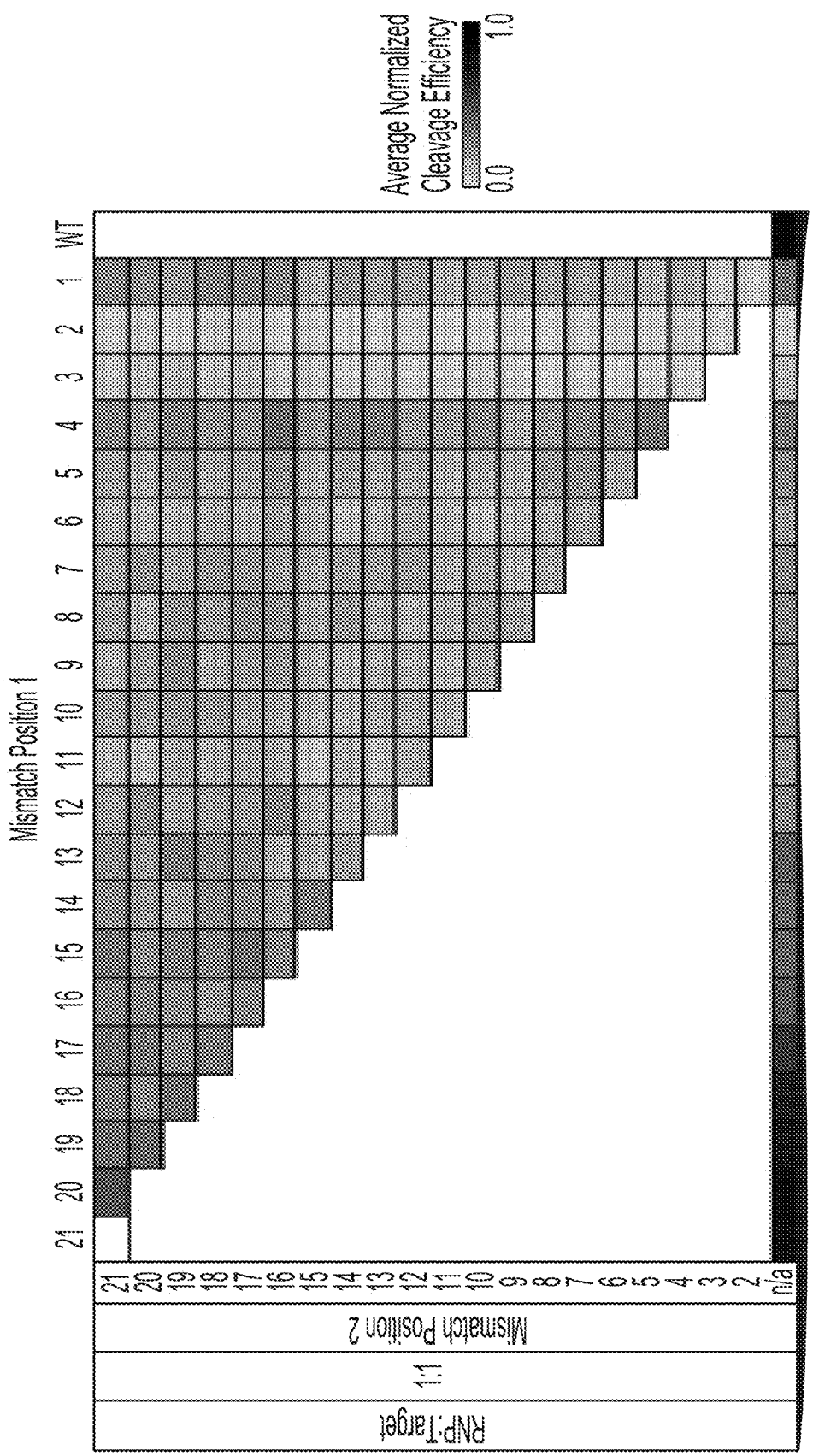
FIG. 2C depicts quantitation of double mismatches by position from PAM and nucleotide, at two different ratios of RNP:target.
Figures 2, 2C:
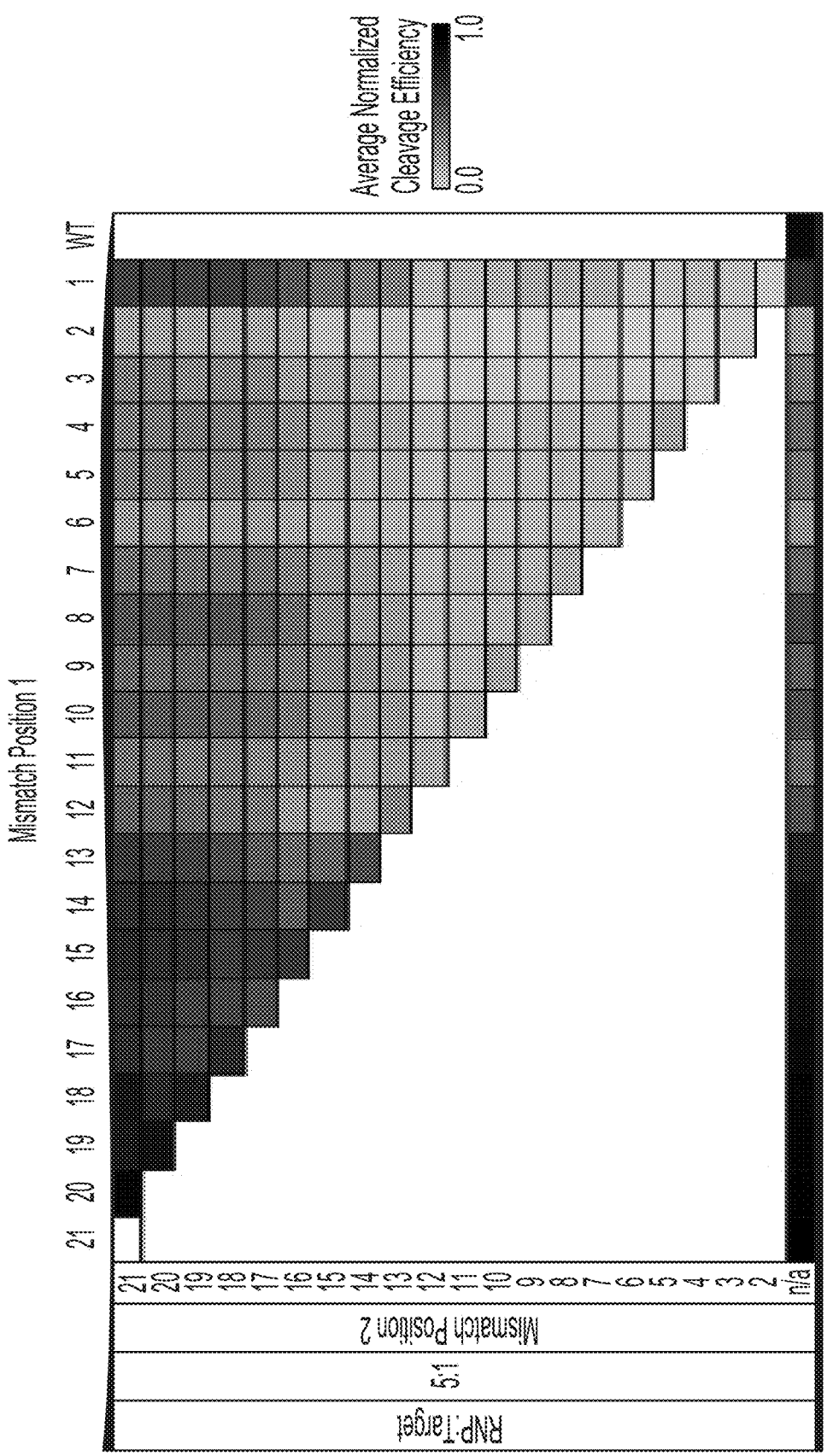
Figure 3A:
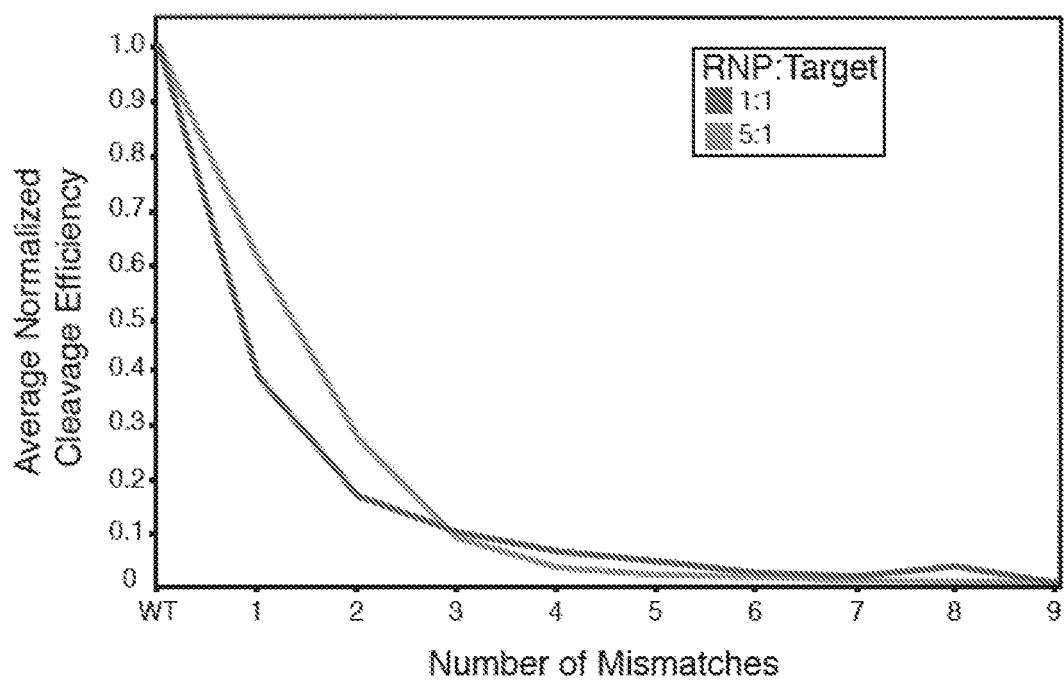
FIG. 3A depicts a plot showing normalized Cas9 activity (y-axis) as a function of number of mismatches (x-axis) at two different ratios of RNP:target. Increasing numbers of mismatches and reduced dose tend to decrease cleavage efficiency.

The BLT approach was also applied to a known promiscuous gRNA (Guide 2). FIG. 2A-2C shows the results of the quantitation for single mismatches (FIG. 2A, FIG. 2B) and double mismatched (FIG. 2C) on the gRNA. The highly diverse libraries allowed for evaluation of higher-order mismatches as well, showing intuitive reduction in Cas9 activity on average as mismatches accumulate (FIG. 3A).

In addition, the importance of a seed region was evidenced by drastically reduced cleavage efficiency in the presence of a single PAM-proximal mismatch. Increasingly PAM-distal mismatches showed a commensurate reduction in the effect observed on cleavage efficiency (FIG. 2A).

Figure 3B:
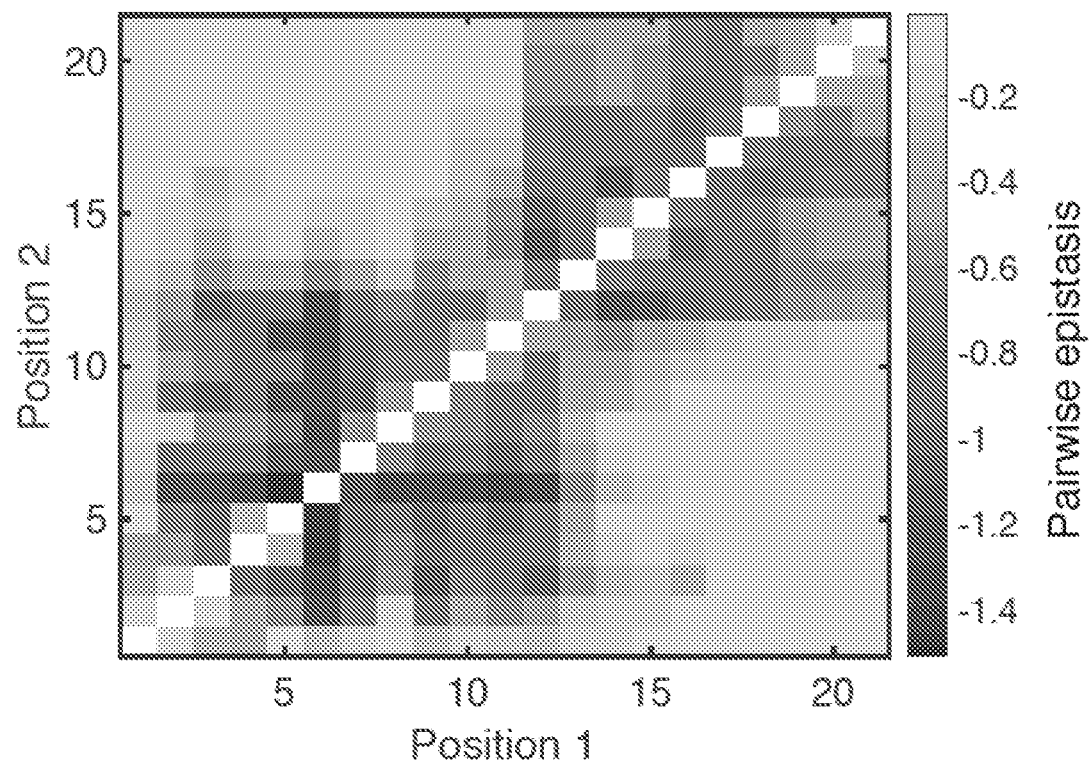
FIG. 3B depicts quantitation of pairwise epistasis when comparing two positions within a particular guide RNA. Strong epistatic effects between two mutations relative to Guide 2 appear to be localized to either within bases 2-12 or within bases 12-21 of the target, indicated by dark gray clusters. However, one mutation from either region has little epistatic effect, indicated by the two light gray clusters.

This method also allowed assessment of the effect of mismatch type on Cas9 cleavage efficiency. For example, mismatched adenines were generally better tolerated in Guide 2 off-targets than any other mismatch type, regardless of PAM proximity (FIG. 2B). Results reliably showed cleavage at select off-targets with greater number of mismatches. Where alternate screens may have difficulty controlling library diversity to adequately analyze more mismatched targets, BLT methodologies of the disclosure are able to accurately measure efficiencies on these members. Combinations of mismatches often showed complex behavior reflecting epistatic interactions, making simple additive models of cleavage of higher order mismatches difficult (FIG. 2C, FIG. 3B). Epistasis between off-target mutations was highly position-dependent (see Equation 5). For example, two mutations within the first 10 bases of the target or the second 10 bases of the target reduced activity more than expected from the individual mutations, but one mutation each from the two halves of the guide tended not to interact epi statically (FIG. 3B).

$$\epsilon_{ab} = \log\frac{\eta_{ab}}{(\eta_a)(\eta_b)} \qquad \text{Equation 5}$$

Where $\in_{ab}$ represents pairwise epistasis between the cleavage efficiency of an off-target with two mutations a and b relative to the on-target.

BLT methods also allowed assessment of effects of stoichiometry of target substrate and RNP complex and cleavage time on cleavage. While increased cutting was observed as RNP dose increased, similar relative profiles of cleavage were observed by number of mismatches or position (FIGS. 2A-2C). Likewise, increasing time of cutting from 30 minutes to 16 hours showed an increase in efficiency but overall similar profiles.

Figure 4A:
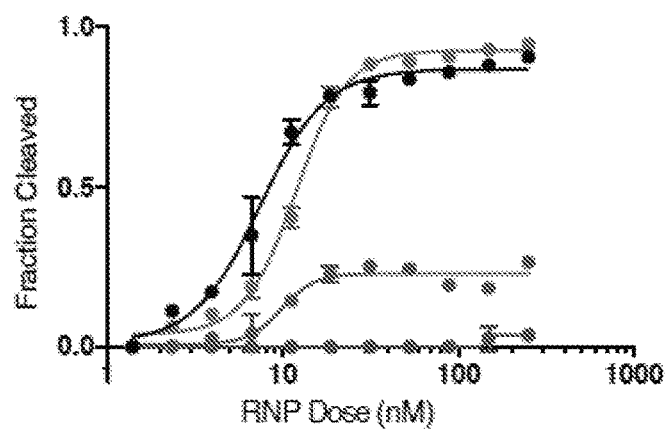
FIGS. 4A and 4B depict testing of exemplary off-targets with different empirically determined efficiencies and measured cutting efficiencies (y-axis) at increasing concentrations of RNP (x-axis).
Figure 4B:
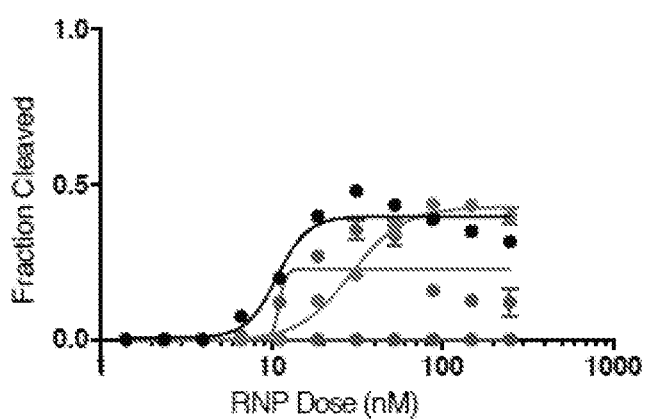

In order to further validate the BLT output, individual off-targets were tested with "high" "medium" or "low" efficiencies of cutting as reported by our analysis in libraries (FIGS. 4A and 4B). These off-targets and an on-target were exposed to increasing doses of Cas9 RNP. Individual in vitro tests verified that the rank order of maximum cutting efficiencies was similar to BLT library output. Biochemical testing confirmed that editing of each target plateaued in cleavage efficiency at increasing dose, indicating an intrinsic editing ceiling for each guide-target pair.

Randomized Libraries Indicated that Mismatch Tolerance was Guide-Specific

Figure 5:
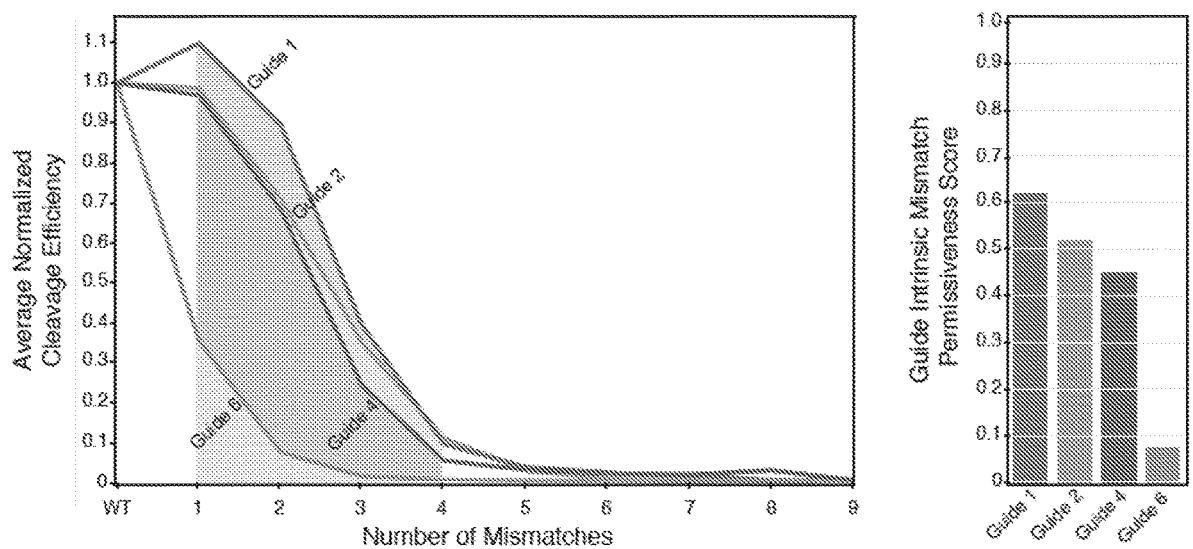
FIG. 5 depicts quantitation of cutting efficiencies for several exemplary guide RNAs with increasing numbers of mismatches (left panel), and depicts a guide-intrinsic mismatch permissiveness score (right panel) for the same exemplary guide RNAs.

Multiple guides were evaluated using BLT (FIG. 5, FIG. 6). These guides included some guides designed to have lower mismatch coverage in the genome as well as known promiscuous guides useful for studying off-target behavior. The use of unbiased sampling of randomized off-targets allowed an evaluation of the effects of guide choice upon off-target cleavage in a genome-independent experiment.

Measuring the average decrease in cutting activity of six guides at random mismatches to their respective targets showed that guides had distinct promiscuities (FIG. 5), implying a sequence-intrinsic (rather than purely position-specific) basis for Cas9-guide promiscuity. A measure of this propensity was calculated by integrating the cleavage efficiency at random targets over increasing numbers of mismatches, generating a Guide-Intrinsic Mismatch Permissiveness (GIMP) score (Equation 3, FIG. 5, FIGS. 6A-6C).

$$GIMP_i = \frac{\int_j^k (\bar{\eta}_i(N))}{k-j}$$ Equation 3

In this study, GIMP score measurements were maintained as measured for mismatches N between j=1 and k=4

Large GIMP scores indicated greater intrinsic promiscuity, while lower scores implied greater specificity. The GIMP metric allowed for a large dynamic range, with GIMP measured scores from $GIMP_{Guide\ 6}$=0.082 to $GIMP_{Guide}$=0.62. Without being bound by theory, it is believed that this score represents the intrinsic tendency of a guide-Cas9 complex to cleave at any target. This score may reflect a combination of multiple factors, including potential ensembles of misfolded RNPs, PAM-proximal DNA-RNA interactions in the folded RNP complex, the propensity of the RNP to transition to its active conformation, and the R-loop complex unwinding the bound DNA with helicase-like activity.

Figure 6A:
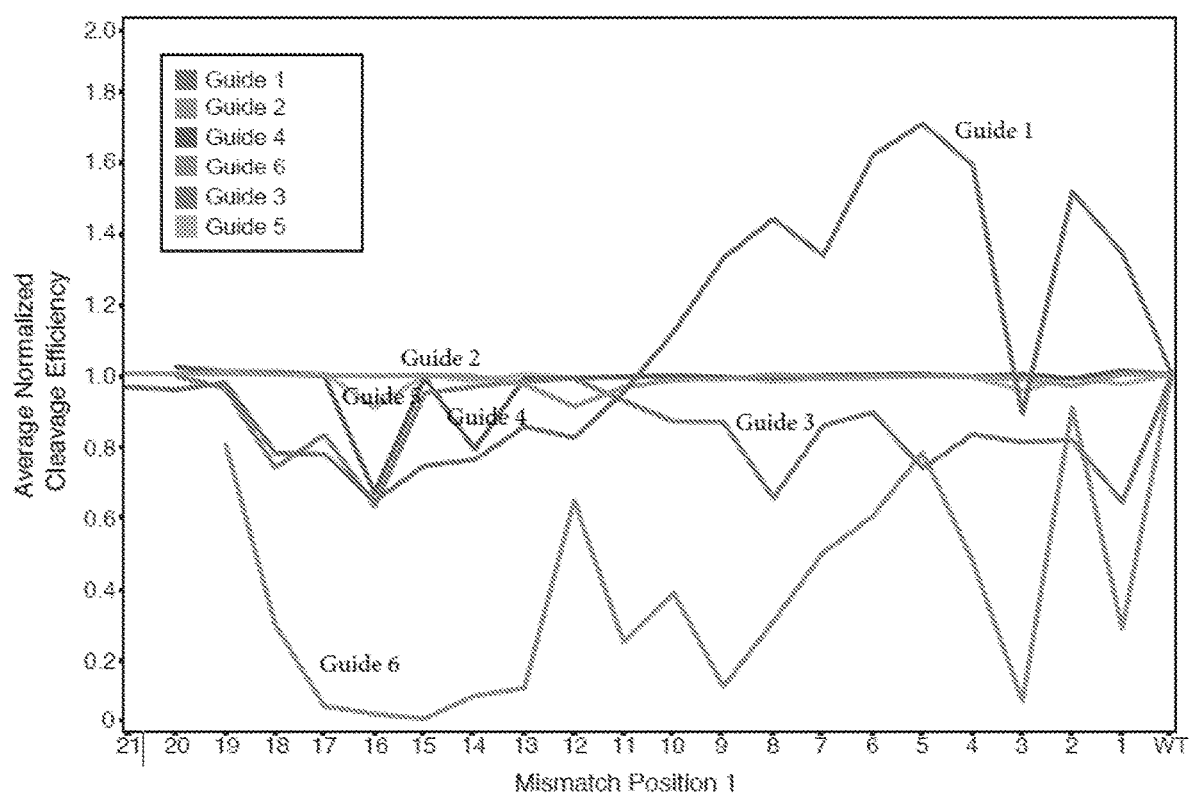
FIGS. 6A-6C show results of evaluation of multiple exemplary guides using BLT and measures of cleavage efficiency by mismatch (6A), guide intrinsic mismatch permissiveness (6B), and on target cleavage efficiency (x-axis) versus GIMP score (y-axis) (6C).
Figure 6B:
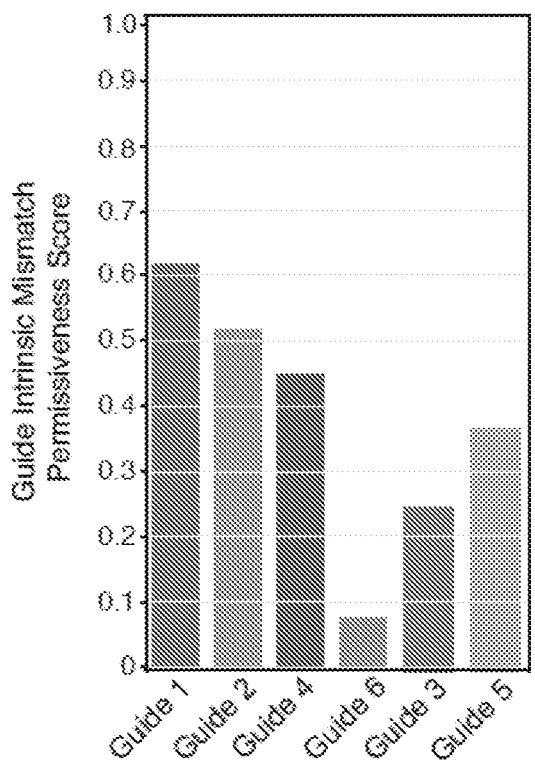
Figure 6C:
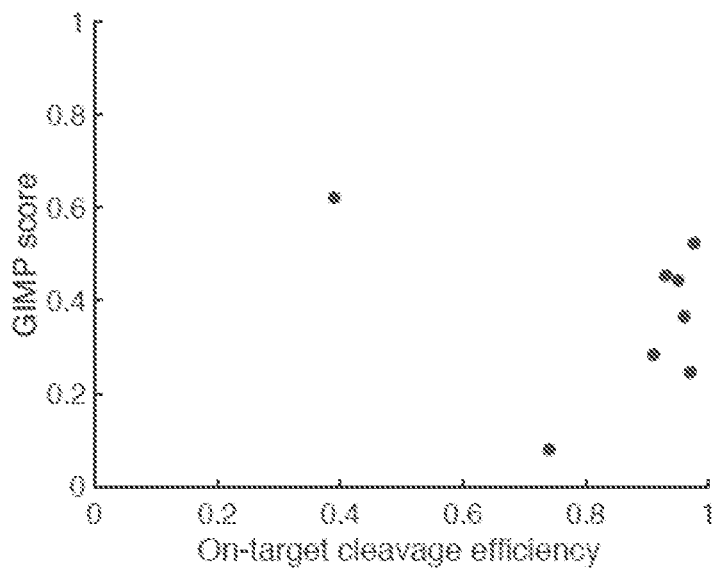

Guides not only varied in activity by numbers of mismatches, but also by effect of mismatch position (FIG. 5, FIG. 6A), supporting sequence-dependent effects of mismatch cleavage. For example, mutations in the seed region of Guide 2 and Guide 1 showed less impact than seed mutations of Guides 3-6 (FIGS. 6A-6C). Individual biochemical testing of off-targets using Guide 1 further verified library results (FIG. 4B). Rank ordering between GIMP scores held consistent at differing doses of Cas9 RNP and was not correlated with on-target cutting efficiency (FIG. 6C). This result validated that GIMP scoring was not an artifact of differential cutting efficiency. The lowest GIMP score resulted from a 19 mer guide (Guide 6), indicating a length-dependent contribution to specificity.

These results indicate that GIMP score can be used to add guide sequence-specific considerations into Cas9 RNP design. Guide 1 and Guide 2 have both high frequency of similar genomic sequences and a high GIMP score, suggesting they have a higher intrinsic propensity to cleave at a larger suite of off-target sites. Choosing a guide with low GIMP score and low numbers of similar genomic sequences may decrease overall risk of off-target cleavage.

Guide-Specific Modeling

Figure 7A:
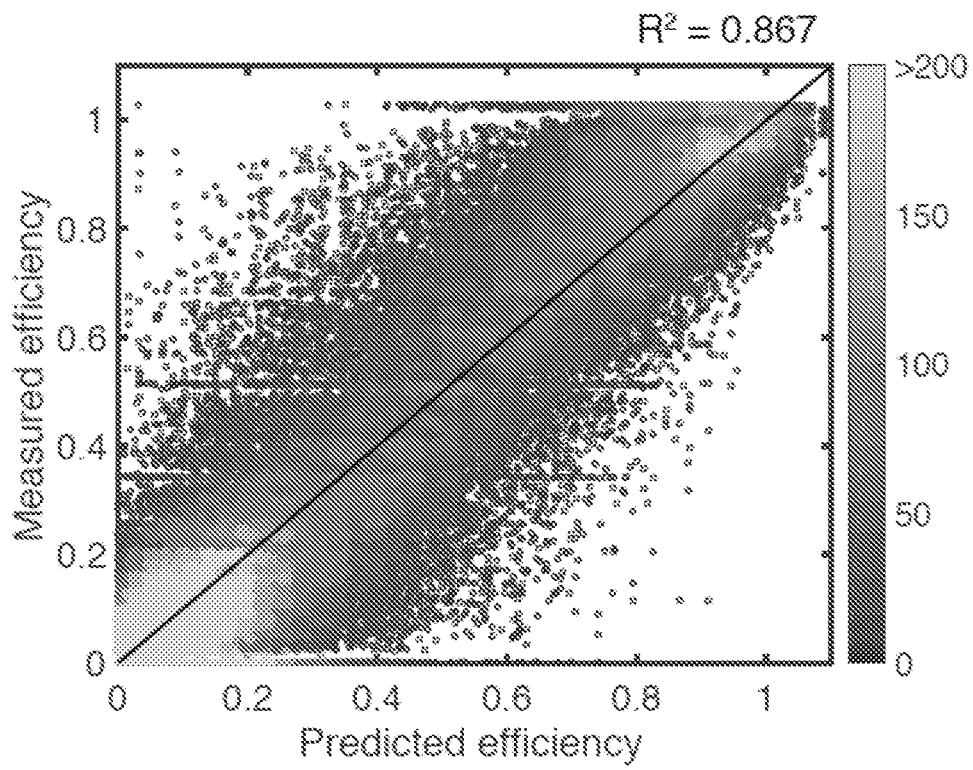
FIG. 7A shows data from a neural network model showing measured and predicted cutting efficiency for Guide 2 RNP.

Models were created for off-target binding that were tailored to specific guide-Cas9 RNP complexes. BLT analysis with randomized targets provided rich data sets for quickly constructing models for a specific guide-protein complex. Methods accurately captured targets with high numbers of mismatches, avoiding overreliance on the effects of single mismatches, which were not usually additive (FIG. 3B). A neural network training algorithm was applied to generate six unique guide-specific models (FIG. 7A). Training used mismatch types and positions as input with normalized cutting efficiency $\eta_i$ as output. The trained models were used to predict cleavage efficiency.

Figure 8A:
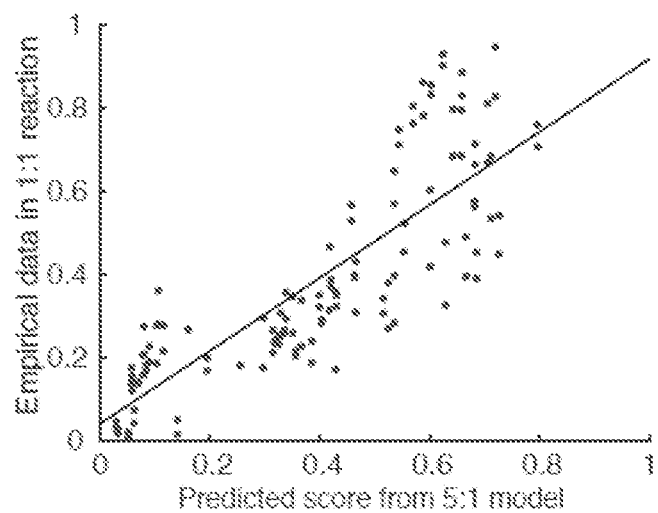
FIG. 8A shows data from a neural network model trained on data from the Guide 2 RNP at 5:1 RNP:target as applied to singly mismatched data from a reaction at 1:1 RNP:target. The predicted score is graphed against the reported cleavage efficiency for each target, with trend line indicated in black ($R^2=0.68$). Larger numbers of mismatches were not modeled due to lower efficiencies at lower doses reaching limits of detection due to poor sampling of the cleaved targets.
Figure 8B:
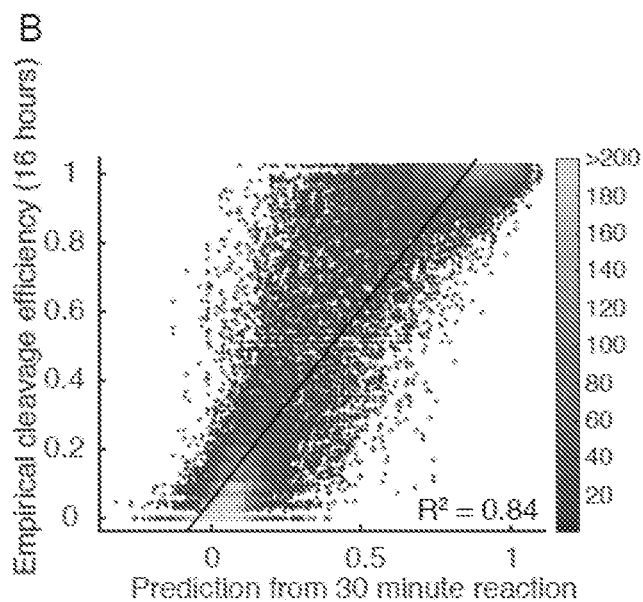
FIG. 8B shows data from a neural network model trained on data from the Guide 2 RNP with conditions of 330 nM RNP:33 nM target for 30 minutes as applied to the library from the 16-hour reaction. The predicted score is graphed against the reported cleavage efficiency for each target, with a trend line indicated in black ($R^2=0.84$). Color indicates density of points.
Figure 8C:
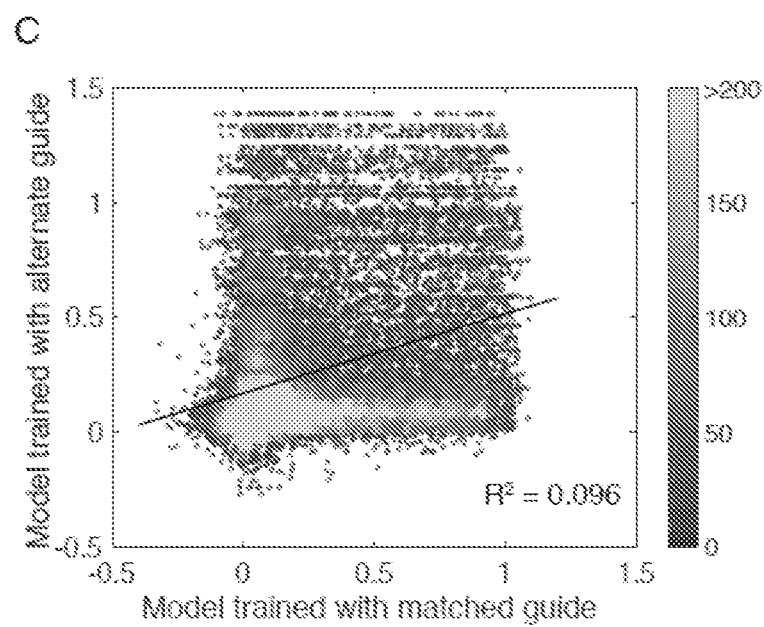
FIG. 8C shows data from a neural network model generated from Guide 3 graphed against the model generated by Guide 2 when applied to Guide 2 off-targets.
Figure 9A:
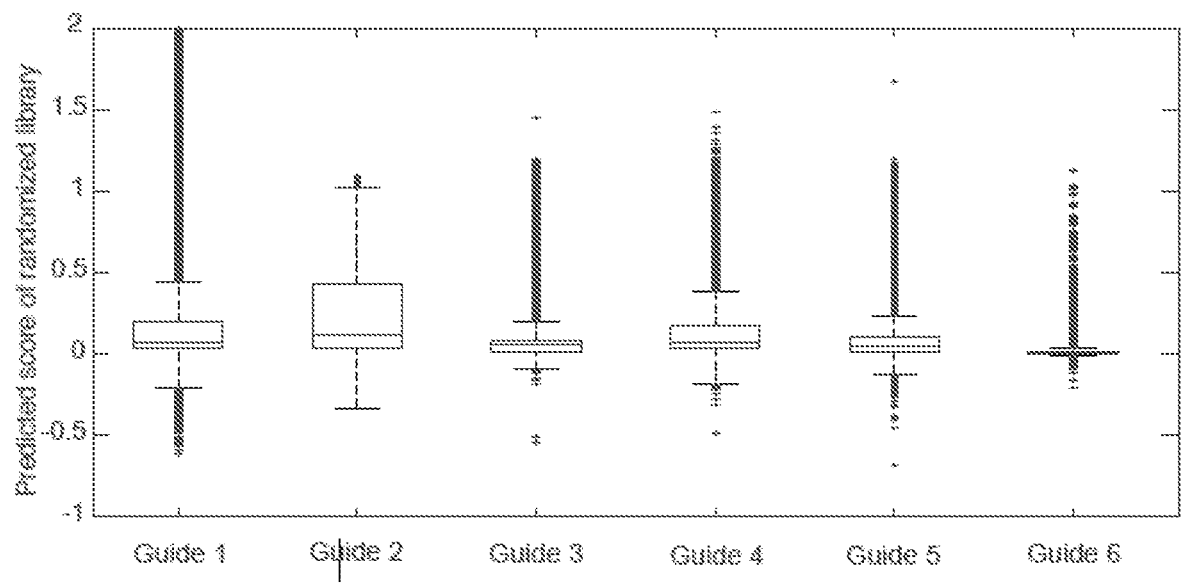
FIG. 9A demonstrates that neural network training scored randomized target DNA across guide models. Box plot distributions are shown for various guides surveyed.

Neural network training allowed for high predictive power on untrained data. For example, using BLT randomized off-targets of the Guide 2 RNP, neural network modeling explained $R^2$=0.87 of the data (FIG. 7A). Modeling performed best when trained on data from higher doses of Cas9 as these experiments produced a wider dynamic range of cutting efficiencies, but models also held predictive power on lower doses (FIG. 8A) and longer time points (FIG. 8B). Models were highly tailored to specific guides and showed very little correlation when applied to data sets from other guide complexes ($R^2$=0.096 when analyzing Guide 2 data with Guide 3 model, FIG. 8C). Distributions of predicted scores on randomized off-targets tended to be lower for guides with lower GIMP scores (FIG. 9A). As with the GIMP score, modeling showed highly guide-specific mismatch tolerability. This analysis implied that for complex off-targets, RNP-specific models offered improved prediction of nuclease cleavage activity.

Figure 7B:
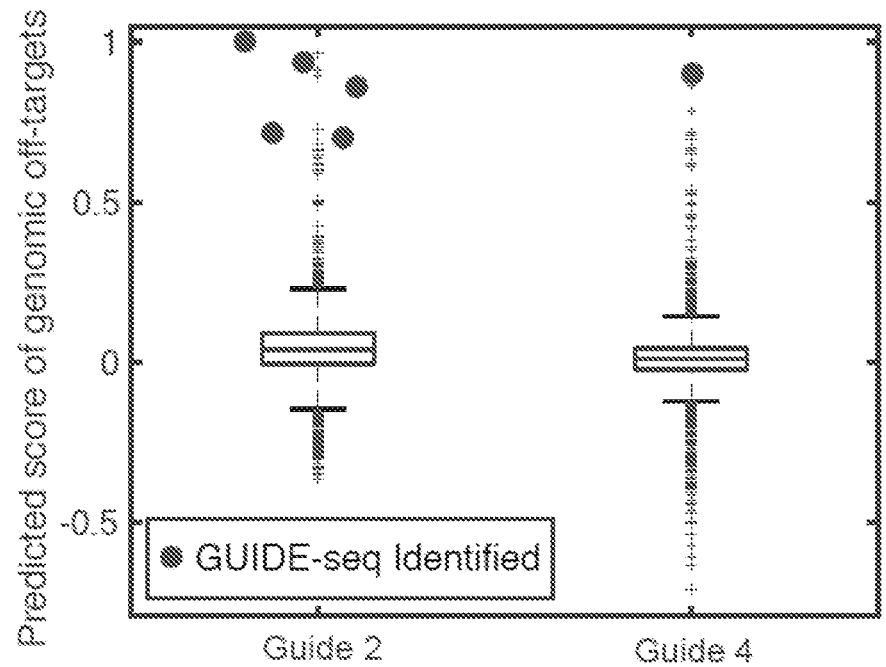
FIG. 7B shows putative genomic off-target cutting for two guides.
Figure 9B:
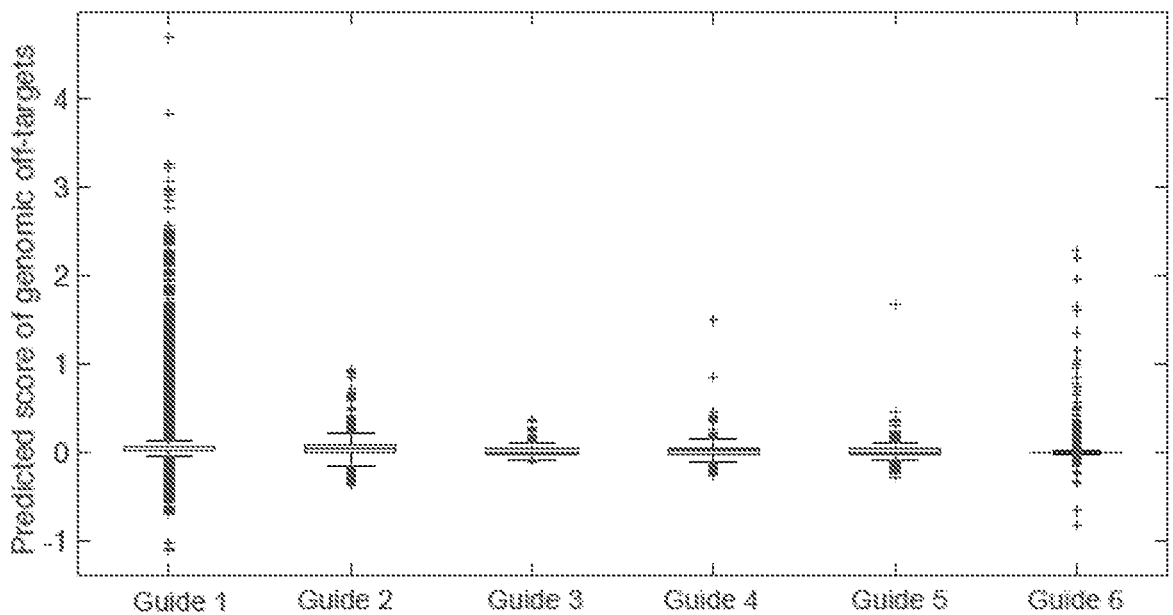
FIG. 9B depicts that neural network training scored putative genomic off-target DNA across guide models. Box plot distributions are shown for various guides surveyed on targets with up to six mismatches in the human genome.

The guide specific model was used to score putative genomic off-targets with up to six mismatches in the reference human genome (FIG. 7B, FIG. 9B). These scores were examined for GUIDE-seq identified off-targets for S. aureus Cas9 from highly promiscuous (high GIMP score) Guide 2 and more specific (low GIMP score) Guide 4. (FIG. 7B). The six sequences with multiple GUIDE-seq identified reads all scored within the top 0.5% (N=39/8564) of possible off-targets in the genome (N≤6 mismatches) for Guide 2. Importantly, the single identified GUIDE-seq off target for Guide 4 scored highest in predicted cleavage efficiency (N=1/3954). As a control, analysis of these off-targets with neural network models created from other guides did not typically show strong scoring, again indicating the ability to capture a nuclease-guide-intrinsic model with high fidelity.

Given this fidelity, improved modeling can be used in identifying off-targets, that may not be identified using GUIDE-seq or other methods, to test via targeted next-generation sequencing. For example, 2 off-targets for Guide 2 were identified, each with three mismatches, as likely to cut out of all 688 triply mismatched targets in the human reference genome. Targeted sequencing could be biased towards these highly scored sites and used to rank-order an extensive in silico list for greater focus on high-risk targets.

Figure 9C:
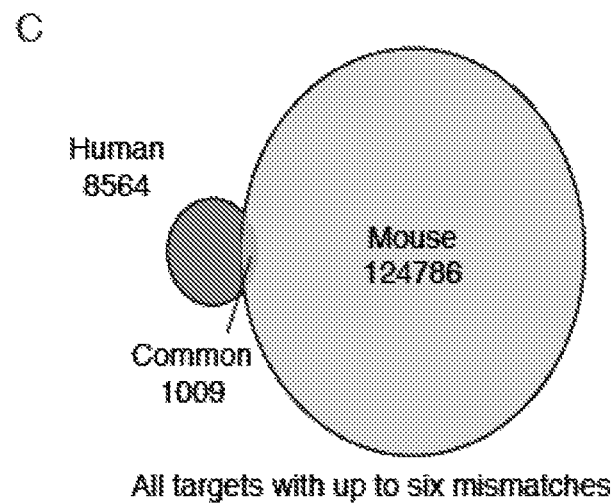
FIG. 9C is a Venn diagram of all off-targets with up to six mismatches in the human or mouse genome.
Figure 9D:
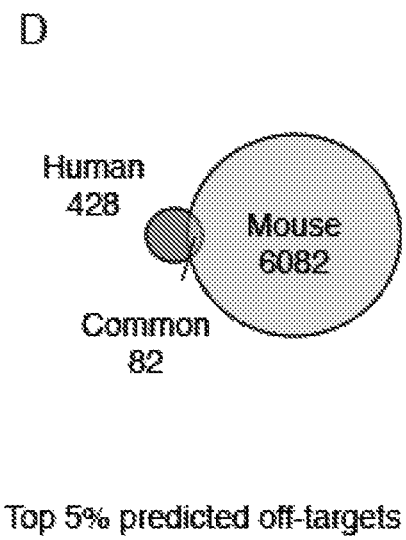
FIG. 9D is a Venn diagram of only the top 5% of predicted off-targets in human or mouse genomes.

Additionally, because modeling is genome-independent, disclosed methods can be used to predict high-risk off-targets across known genomes, chromatin states, or genomic variants. For example, 428 off-targets scored in the top 5% of predicted Guide 2 sites in the human genome. When the model was applied to the mouse genome, the top 5% of sites included 6,082 off-targets (with 82 common to both, FIG. 9C-9D). In contrast, screening all possible off-targets with up to six mismatches unique to the mouse would require analyzing 124,786 sites.

Cleavage Efficiencies of Targets Bound to Cas9 Quantitated Cutting Probabilities Upon RNP Complexing As shown in FIG. 4, plateaus were observed in cleavage efficiencies of on- and off-targets. Understanding the ability of Cas9 to bind without cutting a target could explain these plateaus and could be used to assess gRNA-intrinsic editing limitations in cells. BLT was thus used to distinguish and control factors contributing to Cas9 cleavage from those contributing to Cas9 binding.

Figure 10A:
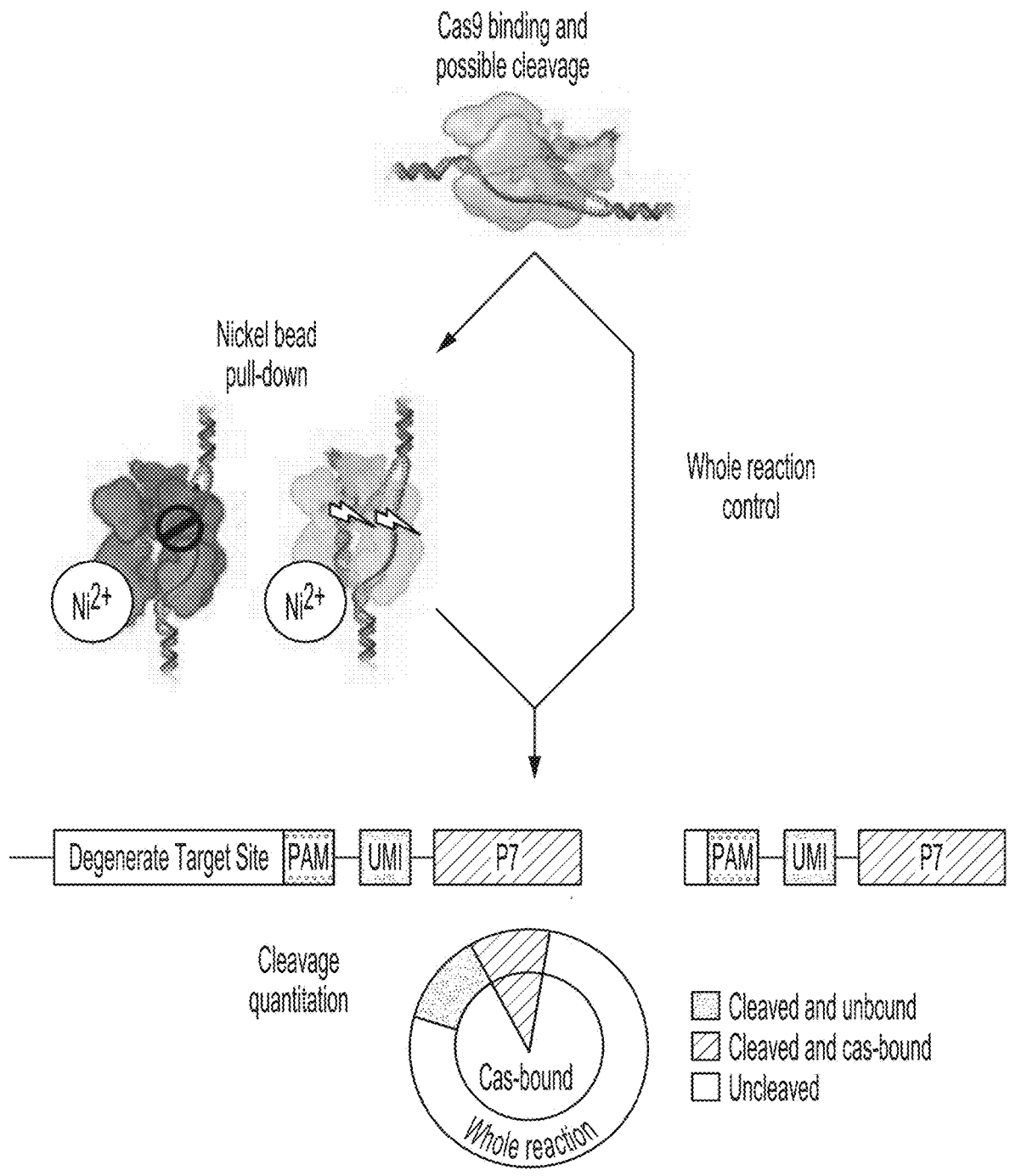
FIG. 10A is a schematic depicting an exemplary BLT-based method of assessing cleaved and unbound, cleaved and Cas-bound, or uncleaved target sequences.

Using a bead pull-down followed by BLT analysis on both the captured fraction of targets bound to Cas9 and a whole-reaction control (containing both bound targets and free targets in reaction), the probability of Cas9 cleavage after binding was measured ($P_{cut}$, Equation 4, FIG. 10A). $P_{cut}$ values approaching 1 suggest Cas9 cleaved successfully once bound. $P_{cut}$ values approaching 0 suggest cleavage did not occur once bound.

$$P_{cut,i} = \frac{\sum Cleaved_i \text{ bound to } cas9}{\sum Molecules_i \text{ bound to } cas9} \quad \text{Equation 4}$$

Figure 10B:
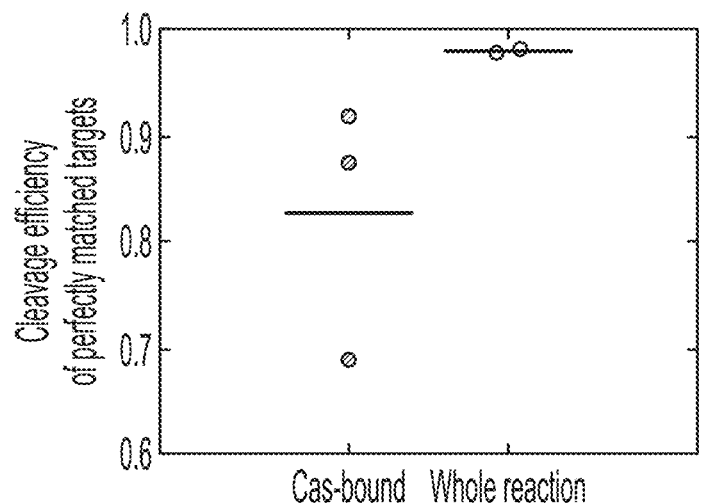
FIG. 10B depicts cleavage efficiency of Guide 2 RNP.

FIG. 10B demonstrates that 1.9% of the on-target population in the whole reaction was uncleaved by the Guide 2 RNP (N=7822/419201 observations total), but in the Cas9-bound fraction 17.7% of the on-target remains uncleaved (N=62587/353065 observations total). Therefore, $P_{cut,Guide2}=0.823$ on the on-target molecule. $P_{cut}$ values may also be guide-specific as testing on Guide 6, a 19 mer with a very low GIMP score, revealed that 73% of on-target molecules in the whole population remained uncleaved (N=162692/221824), while 99.8% of on-target molecules remained uncleaved when Cas-bound (N=337626/336904, $P_{cut,Guide6}=0.002$). Low on-target $P_{cut}$ may contribute to the greater inherent specificity of this guide.

Figure 10C:
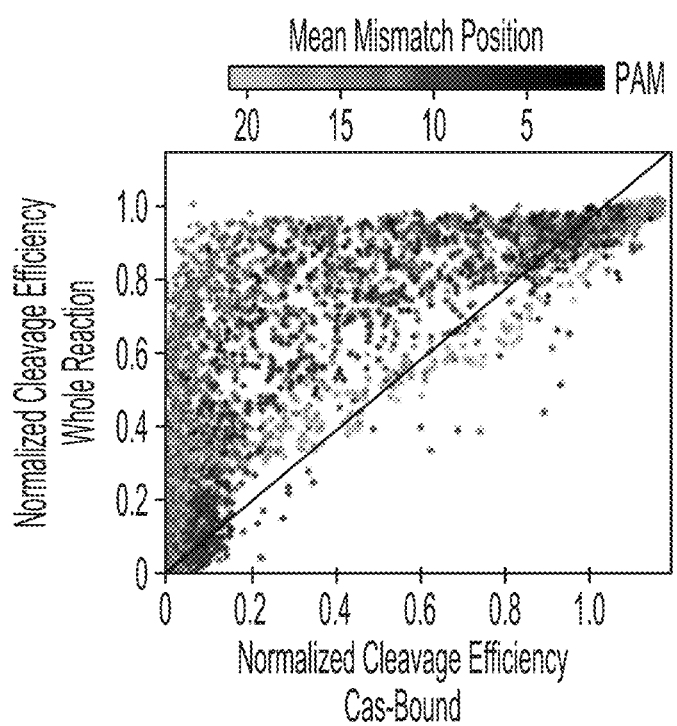
FIG. 10C depicts cutting efficiency of Cas-bound and whole reaction for PAM mismatches.
Figure 11A:
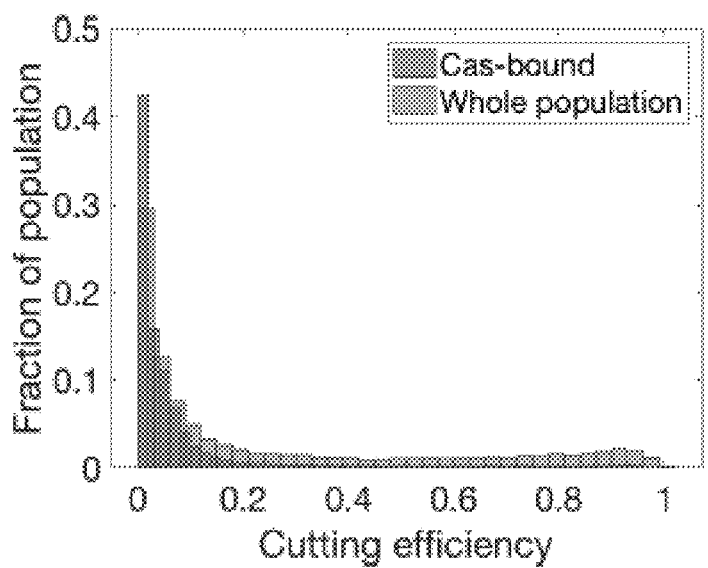
FIG. 11A depicts probability density functions of cleavage efficiency of Cas-bound and whole reaction controls. The histogram of Cas-bound cleavage efficiency is shown in blue while the whole population is shown in orange.
Figure 11B:
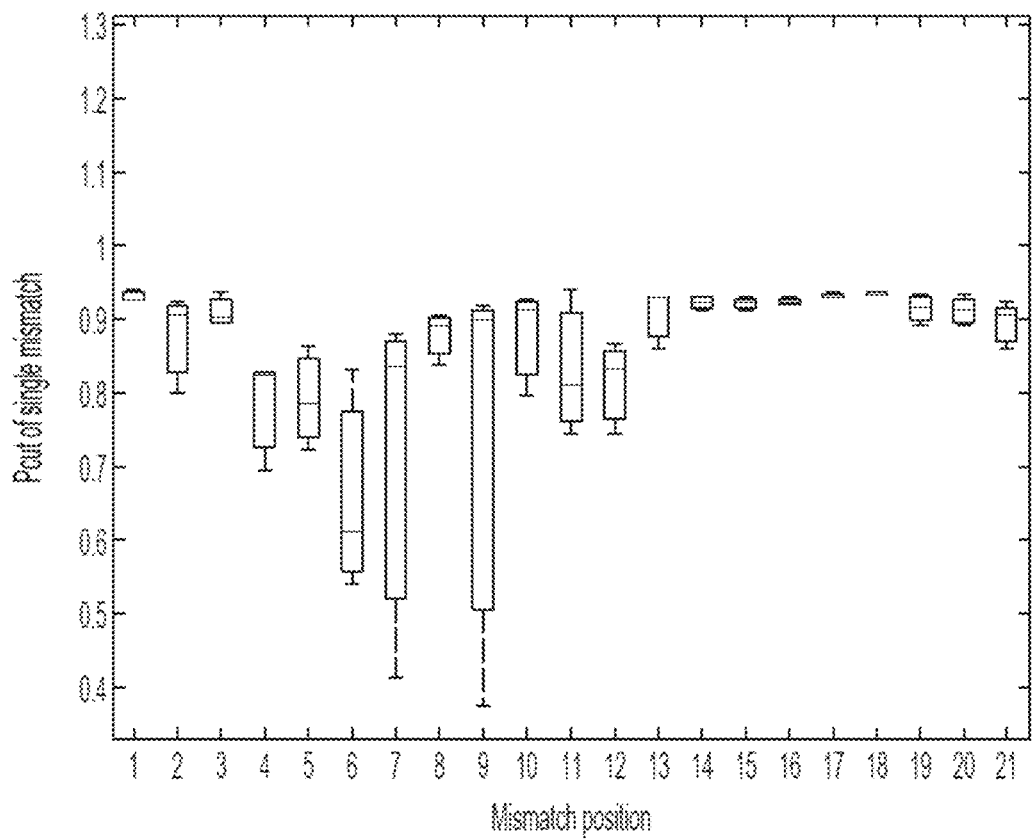
FIG. 11B depicts a boxplot of $P_{cut}$ of single mismatches along the Guide 2 target. Reactions were run at 330 nM RNP:33 nM target for 30 minutes.
Figure 11C:
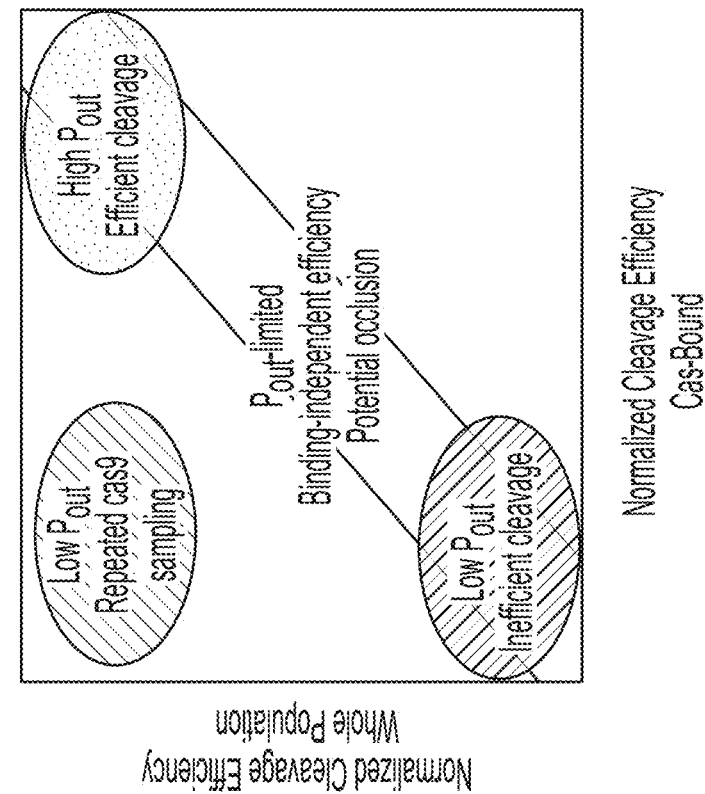
FIG. 11C (left panel) depicts efficiency of cutting in bound and unbound states, and a schematic of results shown in FIG. 11C (right panel).
Figure 11C:
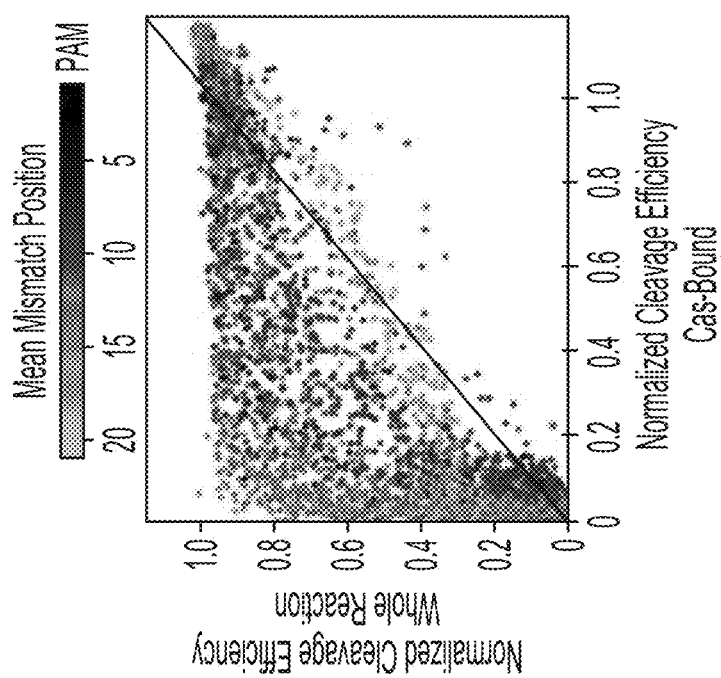

The BLT method extended $P_{cut}$ analysis to off-targets, shown in FIG. 10C. The large majority of mismatched targets showed decreased cutting in Cas9-bound libraries compared to the whole reaction control (FIG. 11A). Unlike previous methods, this approach allowed examination of the position and mismatch base dependence of $P_{cut}$. $P_{cut}$ had a strong position dependence (FIG. 10C, FIG. 11B), with populations of Cas-bound targets that contained several PAM-distal mismatches showing greater parity with their whole population counterparts when compared to targets with more PAM-proximal mismatches (FIG. 11C). Without being bound by theory, this suggests that accumulating PAM-distal mismatches interfered with cleavage activation, but did not interfere as strongly with binding (see, e.g., Sternberg et al., Nature 507:62-67 (2014)).

Figure 12:
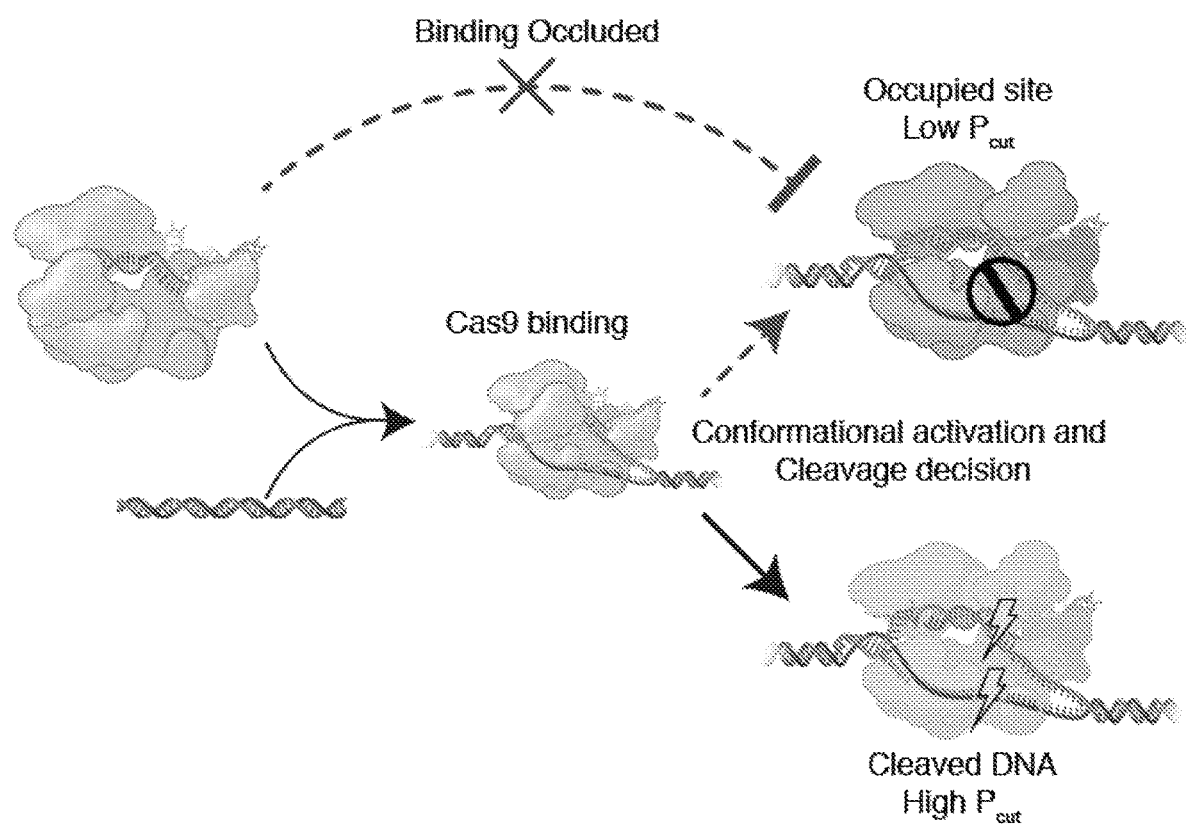
FIG. 12 is a schematic of a model of Cas9 binding and cleavage.

The greater efficiency of cleavage in the whole reaction relative to the Cas-bound fraction may imply that Cas9 RNPs can repeatedly sample targets, possibly by incomplete conformational activation during Cas9 interrogation. In this model, targets experiencing interrogation have an opportunity for Cas9 cleavage given by $P_{cut}$ of that target-RNP complex. However, a population of Cas9 RNP may remain in a bound, non-functional state on these targets if its $P_{cut}$ is low (FIG. 12). In this scenario, a failed cleavage attempt would trap a Cas9 molecule in a bound and inactive conformation, precluding additional cleavage attempts by free Cas9 (FIG. 12). Slow dissociation maintains inactive Cas9 on a given site, and this occlusion could explain plateaus in cleavage efficiency: a probabilistic fraction of bound Cas9 successfully cut, but an alternate population remains bound and prevents repeated cutting attempts despite increasing reaction times or RNP dose.

Example 2

Schematic for a Method of Evaluating Protospacer-Adjacent Motifs of RNA-Guided Nucleases The present Example illustrates a schematic for evaluating and/or determining the PAM sequence for an RNA-guided nuclease.

A library of DNA templates is constructed in a similar manner as that described in Example 1, except that the library is not barcoded, and the DNA templates in the library have a constant target site region and a fully degenerate PAM sequence of 7 nucleotides. No control target site (such as an EcoRV site for use with an EcoRV control nuclease) is required. A barcode is not used because the PAM site is expected to remain intact (and available for identification by sequencing) after cleavage at the target site by the RNA-guided nuclease being evaluated.

Figure 13:
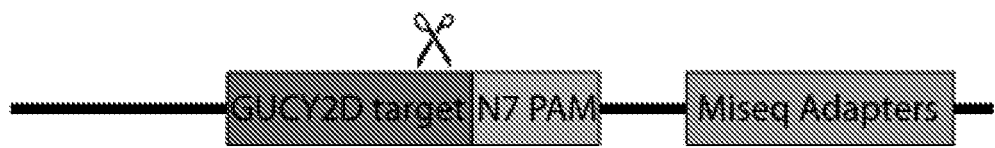
FIG. 13 depicts a schematic showing an exemplary nucleic acid template for evaluating a protospacer-adjacent motif, comprising in order from 5' to 3' or from 3' to 5': a fixed target site, a variable (degenerate) PAM adjacent to the target site, and a sequence adapter. See Example 2.

Thus, each DNA template in the library comprises, in order from 5' to 3' or from 3' to 5': a fixed target site, a variable (degenerate) PAM adjacent to the target site, and a sequence adapter. (See, e.g., FIG. 13)

The library containing a fully degenerate PAM is used directly (without bottlenecking). Samples are first incubated with the RNA-guided nuclease to allow cleavage by the RNA-guided nucleases of those DNA templates with a suitable PAM. Oligonucleotide capture probes having a blunt end and comprising a complementary sequence adapter are then added to the samples, along with T4 ligase. Ligation events are only expected to occur with DNA templates that had been cleaved by the RNA-guided endonucleases, which leave a free 5' phosphate and is required for ligation by T4 ligase.

Ligation products represent only those DNA templates with PAMs suitable for cleavage. These ligation products are then amplified using amplification primers that recognize the sequence adapters, and amplification products are sequenced to determine the identity of PAM site(s) that are compatible with cleavage by the RNA-guided endonuclease.

EQUIVALENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

The invention claimed is:

1. A method of assessing cleavage of a target cleavage site of a plurality of variant nucleic acid templates by a CRISPR associated DNA endonuclease, wherein each of the plurality of variant nucleic acid templates comprises degenerate sequences in its candidate target site for the CRISPR associated DNA endonuclease, the method comprising the steps of:

(a) obtaining a first cleavage composition by incubating a plurality of variant nucleic acid templates with a CRISPR associated DNA endonuclease and a plurality of guide RNAs under conditions favorable for cleavage of at least one variant nucleic acid template of the plurality of variant nucleic acid templates by the CRISPR associated DNA endonuclease in complexes formed by the CRISPR associated DNA endonuclease and at least one guide RNA from the plurality of guide RNAs, (i) wherein each variant nucleic acid template of the plurality of nucleic acid templates comprises:

(A) a candidate target site for the CRISPR associated DNA endonuclease, wherein the candidate target site for the CRISPR associated DNA endonuclease is degenerate target sites comprising the degenerate nucleotide sequences, (B) a protospacer adjacent motif (PAM) site situated adjacent to the candidate target site, and (C) a restriction enzyme target site; and (ii) wherein the first cleavage composition comprises:

a first plurality of cleaved variant nucleic acid templates, wherein each of the cleaved variant nucleic acid templates comprises a cleaved end generated by the CRISPR associated DNA endonuclease and the degenerate target sites uncleaved by the CRISPR associated DNA endonuclease but lacks the restriction enzyme target site, and a first plurality of uncleaved variant nucleic acid templates, wherein each of the uncleaved variant nucleic acid templates comprises the restriction enzyme target site and the degenerate target sites that are not capable of cleaving by the CRISPR associated DNA endonuclease but lacks the cleaved end generated by the CRISPR associated DNA endonuclease;

(b) incubating the first cleavage composition with the restriction enzyme under conditions to allow cleavage of the first plurality of uncleaved variant nucleic acid templates by the restriction enzyme, thereby obtaining a second cleavage composition comprising:
  (i) the first plurality of cleaved variant nucleic acid templates, and
  (ii) a second plurality of cleaved variant nucleic acid templates comprising a cleaved end generated by the restriction enzyme and the degenerate target sites that are not capable of cleaving by the CRISPR associated DNA endonuclease but lacking the restriction enzyme target site and the cleaved end generated by the CRISPR associated DNA endonuclease; and
(c) ligating the second cleavage composition with one or more oligonucleotide capture probes and obtaining:
  (i) a first plurality of ligation products comprising the one or more oligonucleotide capture probes and the first plurality of cleaved variant nucleic acid templates, and
  (ii) a second plurality of ligation products comprising the one or more oligonucleotide capture probes and the second plurality of cleaved variant nucleic acid templates; and
(d) detecting presence of the first plurality of ligation products and the second plurality of ligation products, thereby assessing the cleavage of the target cleavage site of the plurality of variant nucleic acid templates by the CRISPR associated DNA endonuclease.

2. The method of claim 1, further comprising a step for determining the levels of the first plurality of ligation products and the second plurality of ligation products.

3. The method of claim 1, wherein the one or more oligonucleotide capture probes comprise at least one detection sequence.

4. The method of claim 1, further comprising a step for determining a relative abundance of the first plurality of ligation products to the second plurality of ligation products.

5. The method of claim 1, wherein the CRISPR associated DNA endonuclease is Cas9.

6. The method of claim 1, wherein each of the variant nucleic acid templates comprises (D) a unique molecular identifier associated with each of the variant nucleic acid templates.

7. The method of claim 6, wherein
each of the variant nucleic acid templates further comprises a detection sequence,
the unique molecular identifier is situated between the candidate target site and the detection sequence,
the first plurality of ligation products further comprises the detection sequence and the unique molecular identifier, and
the second plurality of ligation products further comprises the detection sequence and the unique molecular identifier.

8. The method of claim 6, further comprising a step for detecting the unique molecular identifier in a ligation product from the first plurality of ligation products.

9. The method of claim 8, further comprising determining relative abundance of the first plurality of ligation products.

10. The method of claim 9, further comprising a step for identifying a variant nucleic acid template of the plurality of variant nucleic acid templates.

11. The method of claim 1, further comprising a step for amplifying the first plurality of ligation products and the second plurality of ligation products.

12. The method of claim 11, wherein
each of the plurality of variant nucleic acid templates further comprises a detection sequence, and
the amplifying step comprises performing an amplification reaction using amplification primers that recognize the detection sequence.

13. The method of claim 1, wherein each of the capture probes comprises at least one detection sequence and a randomized barcode sequence.

14. The method of claim 13, further comprising a step for analyzing the target sequence of the CRISPR associated DNA endonuclease, analyzing the distribution of the randomized barcode sequence present in the first plurality of ligation products and/or analyzing the distribution of the randomized barcode sequence present in the second plurality of ligation products.

15. The method of claim 1, wherein each of the variant nucleic acid templates further comprises a unique molecular identifier associated with the candidate target site for the CRISPR associated DNA endonuclease, and a first detection sequence and comprises in order from its 5' to its 3' or its 3' to its 5': the restriction enzyme target site, the candidate target site for the CRISPR associate DNA endonuclease, the protospacer adjacent motif (PAM) site situated adjacent to the candidate target site, the unique molecular identifier associated with the candidate target site, and the first detection sequence.

16. The method of claim 15, further comprising a step for identifying a variant nucleic acid template of the plurality of variant nucleic acid templates.

17. A method of assessing RNA guided cleavage of a target cleavage site of a plurality of variant nucleic acid templates by a CRISPR-associated DNA endonuclease, wherein each of the plurality of variant nucleic acid templates comprises degenerate sequences in its candidate target site for the CRISPR associated DNA endonuclease, the method comprising the steps of:
  (a) obtaining a first cleavage composition by incubating a plurality of variant nucleic acid templates with a CRISPR associated DNA endonuclease and a guide RNA under conditions favorable for cleavage of a variant nucleic acid template of the plurality of variant nucleic acid templates by the CRISPR associated DNA endonuclease in complexes formed by the CRISPR associated DNA endonuclease and the guide RNA,
    (i) wherein each of the plurality of variant nucleic acid templates comprises:
      (A) a candidate target site for the CRISPR associated DNA endonuclease, wherein the candidate target site for the CRISPR associated DNA endonuclease is degenerate target sites comprising the degenerate nucleotide sequences,
      (B) a protospacer adjacent motif (PAM) site situated adjacent to the candidate target site, and
      (C) a restriction enzyme target site; and
    (ii) wherein the first cleavage composition comprises:
      a first plurality of cleaved variant nucleic acid templates, wherein each of the cleaved variant nucleic acid templates comprises a cleaved end generated by the CRISPR associated DNA endonuclease and the degenerate target sites uncleaved by the CRISPR associated DNA endonuclease but lacks the restriction enzyme target site, and
      a first plurality of uncleaved variant nucleic acid templates, wherein each of the uncleaved variant nucleic acid templates comprises the restriction enzyme target site and the degenerate target sites that are not capable of cleaving by the CRISPR associated DNA endonuclease but lacks the cleaved end generated by the CRISPR associated DNA endonuclease;
(b) incubating the first cleavage composition with the restriction enzyme under conditions to allow cleavage of the first plurality of uncleaved variant nucleic acid templates by the restriction enzyme, thereby obtaining a second cleavage composition comprising:
  (i) the first plurality of cleaved variant nucleic acid templates, and
  (ii) a second plurality of cleaved variant nucleic acid templates comprising a cleaved end generated by the restriction enzyme and the degenerate target sites that are not capable of cleaving by the CRISPR associated DNA endonuclease but lacking the restriction enzyme target site and the cleaved end generated by the CRISPR associated DNA endonuclease;
(c) ligating the second cleavage composition with an oligonucleotide capture probe and obtaining:
  (i) a first plurality of ligation products comprising the oligonucleotide capture probe and the first plurality of cleaved variant nucleic acid templates, and
  (ii) a second plurality of ligation products comprising the oligonucleotide capture probe and the second plurality of cleaved variant nucleic acid templates; and
(d) detecting presence of the first plurality of ligation products and the second plurality of ligation products, thereby assessing the RNA guided cleavage of the target cleavage site of the plurality of variant nucleic acid templates by the CRISPR associated DNA endonuclease.

18. The method of claim 17, wherein the CRISPR associated DNA endonuclease is Cas9.

* * * * *

SEQUENCE LISTING

<160> NUMBER OF SEQ ID NOS: 38

<210> SEQ ID NO 1
<211> LENGTH: 31
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 1
gcctggactc aaccggaccc ggggatatct g                                      31

<210> SEQ ID NO 2
<211> LENGTH: 82
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (3)..(14)
<223> OTHER INFORMATION: a, c, t, g, unknown or other

<400> SEQUENCE: 2
gcnnnnnnnn nnnntgacag atcggaagag cacacgtctg aactccagtc acgctgctat        60
ctcgtatgcc gtcttctgct tg                                                82

<210> SEQ ID NO 3
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 3
guuuuaguac ucuguaauuu u                                                 21

<210> SEQ ID NO 4
<211> LENGTH: 69
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 4
aaaauuacag aaucuacuaa aacaaggcaa aaugccgugu uuaucucguc aacuuguugg        60
cgagauuuu                                                               69

<210> SEQ ID NO 5
<211> LENGTH: 127
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic probe"
<220> FEATURE:
<221> NAME/KEY: modified_base
<222> LOCATION: (94)..(99)
<223> OTHER INFORMATION: a, c, t, g, unknown or other

<400> SEQUENCE: 5
aatgatacgg cgaccaccga gatctacact ctttccctac acgacgctct tccgatctgc    60
ggaagccgat ctcacatacg cactacgtac gacnnnnnnt taccgaagat agcagcctag   120
tggaacc                                                             127

<210> SEQ ID NO 6
<211> LENGTH: 126
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic probe"
<220> FEATURE:
<221> NAME/KEY: modified_base
<222> LOCATION: (93)..(98)
<223> OTHER INFORMATION: a, c, t, g, unknown or other

<400> SEQUENCE: 6
aatgatacgg cgaccaccga gatctacact ctttccctac acgacgctct tccgatctgc    60
ggaagcgatc tcctataccc gaatcttacg acnnnnnntt accgaagata gcagcctagt   120
ggaacc                                                              126

<210> SEQ ID NO 7
<211> LENGTH: 125
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic probe"
<220> FEATURE:
<221> NAME/KEY: modified_base
<222> LOCATION: (92)..(97)
<223> OTHER INFORMATION: a, c, t, g, unknown or other

<400> SEQUENCE: 7
aatgatacgg cgaccaccga gatctacact ctttccctac acgacgctct tccgatctgc    60
ggaacgatct tatacaattc gcagctacga cnnnnnntta ccgaagatag cagcctagtg   120
gaacc                                                               125

<210> SEQ ID NO 8
<211> LENGTH: 124
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic probe"
<220> FEATURE:
<221> NAME/KEY: modified_base
<222> LOCATION: (91)..(96)
<223> OTHER INFORMATION: a, c, t, g, unknown or other

<400> SEQUENCE: 8
aatgatacgg cgaccaccga gatctacact ctttccctac acgacgctct tccgatctgc    60
ggacgatctc cggagtaggt cctctacgac nnnnnnttac cgaagatagc agcctagtgg   120
aacc                                                                124

<210> SEQ ID NO 9
<211> LENGTH: 123
<212> TYPE: DNA

```
<213> ORGANISM: Artificial Sequence
<220> FEATURE:
<221> NAME/KEY: source
<223> OTHER INFORMATION: /note="Description of Artificial Sequence:
      Synthetic probe"
<220> FEATURE:
<221> NAME/KEY: modified_base
<222> LOCATION: (90)..(95)
<223> OTHER INFORMATION: a, c, t, g, unknown or other

<400> SEQUENCE: 9
aatgatacgg cgaccaccga gatctacact ctttccctac acgacgctct tccgatctgc    60
ggcgatctat tgcaagggcc ctttacgacn nnnnnttacc gaagatagca gcctagtgga   120
acc                                                                 123

<210> SEQ ID NO 10
<211> LENGTH: 122
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic probe"
<220> FEATURE:
<221> NAME/KEY: modified_base
<222> LOCATION: (89)..(94)
<223> OTHER INFORMATION: a, c, t, g, unknown or other

<400> SEQUENCE: 10
aatgatacgg cgaccaccga gatctacact ctttccctac acgacgctct tccgatctgc    60
gcgatcttcc cgtcgtccac aatacgacnn nnnnttaccg aagatagcag cctagtggaa   120
cc                                                                  122

<210> SEQ ID NO 11
<211> LENGTH: 121
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic probe"
<220> FEATURE:
<221> NAME/KEY: modified_base
<222> LOCATION: (88)..(93)
<223> OTHER INFORMATION: a, c, t, g, unknown or other

<400> SEQUENCE: 11
aatgatacgg cgaccaccga gatctacact ctttccctac acgacgctct tccgatctgc    60
cgatcttgcg tgacaagctc ttacgacnnn nnnttaccga agatagcagc ctagtggaac   120
c                                                                   121

<210> SEQ ID NO 12
<211> LENGTH: 120
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic probe"
<220> FEATURE:
<221> NAME/KEY: modified_base
<222> LOCATION: (87)..(92)
<223> OTHER INFORMATION: a, c, t, g, unknown or other

<400> SEQUENCE: 12
aatgatacgg cgaccaccga gatctacact ctttccctac acgacgctct tccgatctgc    60
```

```
gatctgcgca gtctttctgc tacgacnnnn nnttaccgaa gatagcagcc tagtggaacc    120
```

<210> SEQ ID NO 13
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 13

```
ggccuccccca aagccuggcc a                                              21
```

<210> SEQ ID NO 14
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 14

```
ggguagaguga gugugugcgu g                                              21
```

<210> SEQ ID NO 15
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 15

```
gaauaguuug uucuggguac                                                 20
```

<210> SEQ ID NO 16
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 16

```
gagaaaggga ugggcacuua                                                 20
```

<210> SEQ ID NO 17
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 17

```
gaugcagaac uaguguagac                                                 20
```

<210> SEQ ID NO 18
<211> LENGTH: 19
<212> TYPE: RNA
<213> ORGANISM: Artificial Sequence
<220> FEATURE:

```
<221> NAME/KEY: source
<223> OTHER INFORMATION: /note="Description of Artificial Sequence:
      Synthetic oligonucleotide"

<400> SEQUENCE: 18
gaguaucucc uguuuggca                                                19

<210> SEQ ID NO 19
<211> LENGTH: 29
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 19
caggcctccc caaagcctgg ccagggagt                                     29

<210> SEQ ID NO 20
<211> LENGTH: 29
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 20
cctggccagg ctttggggag gccgggagt                                     29

<210> SEQ ID NO 21
<211> LENGTH: 29
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 21
ggagaatagt ttgttctggg tacaggggt                                     29

<210> SEQ ID NO 22
<211> LENGTH: 29
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 22
taagagaaag ggatgggcac ttaatgagt                                     29

<210> SEQ ID NO 23
<211> LENGTH: 29
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 23
taagatgcag aactagtgta gacaggagt                                     29
```

```
<210> SEQ ID NO 24
<211> LENGTH: 29
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 24
tgttgagtat ctcctgtttg gcacagagt                                      29

<210> SEQ ID NO 25
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 25
ggtctgtggg tgtgtgcatg                                                20

<210> SEQ ID NO 26
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 26
ggtgagtgag tgtgtacgtg                                                20

<210> SEQ ID NO 27
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 27
ggtgattgag tctgtgcgtg                                                20

<210> SEQ ID NO 28
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 28
gggtgagtga gtgtgtgcgt g                                              21

<210> SEQ ID NO 29
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
```

-continued

<400> SEQUENCE: 29
gggtaagtga gtgtgagcgt g  21

<210> SEQ ID NO 30
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 30
gggtgattga ttgtgtgcgt g  21

<210> SEQ ID NO 31
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 31
gggtgagtga gtgtgggcct g  21

<210> SEQ ID NO 32
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 32
ggcctcccca aagcctggcc a  21

<210> SEQ ID NO 33
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 33
gggctcccca aagcttggcc a  21

<210> SEQ ID NO 34
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 34
ggcttcctca aagcctggcc a  21

<210> SEQ ID NO 35
<211> LENGTH: 21
<212> TYPE: DNA
<213> ORGANISM: Artificial Sequence

```
<220> FEATURE:
<221> NAME/KEY: source
<223> OTHER INFORMATION: /note="Description of Artificial Sequence:
      Synthetic oligonucleotide"

<400> SEQUENCE: 35
ggcctgcgca aagcctggcc a                                              21

<210> SEQ ID NO 36
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 36
gggtgggggg agtttgctcc                                                20

<210> SEQ ID NO 37
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 37
ggatgggggg agtttgctcc                                                20

<210> SEQ ID NO 38
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic 6xHis tag"

<400> SEQUENCE: 38

His His His His His His
1               5
```